(12) United States Patent
Lo et al.

(10) Patent No.: US 10,837,061 B2
(45) Date of Patent: Nov. 17, 2020

(54) ENRICHMENT AND DETECTION OF NUCLEIC ACIDS WITH ULTRA-HIGH SENSITIVITY

(71) Applicants: The Regents of the University of California, Oakland, CA (US); Compliance Decisions, Inc., Irvine, CA (US)

(72) Inventors: Yu-Hwa Lo, San Diego, CA (US); Wen Qiao, Suzhou (CN); Tiantian Zhang, San Diego, CA (US); Ian Lian, Alhambra, CA (US); Tony Minghung Yen, Santa Clara, CA (US)

(73) Assignees: The Regents of the University of California, Oakland, CA (US); Compliance Decisions, Inc., Irvine, CA (US)

( * ) Notice: Subject to any disclaimer, the term of this patent is extended or adjusted under 35 U.S.C. 154(b) by 127 days.

(21) Appl. No.: 16/111,108

(22) Filed: Aug. 23, 2018

(65) Prior Publication Data
US 2019/0194751 A1    Jun. 27, 2019

Related U.S. Application Data

(62) Division of application No. 15/031,062, filed as application No. PCT/US2014/061639 on Oct. 21, 2014, now abandoned.
(Continued)

(51) Int. Cl.
*C12Q 1/68*    (2018.01)
*C12Q 1/6883*    (2018.01)
(Continued)

(52) U.S. Cl.
CPC ......... *C12Q 1/6883* (2013.01); *B01L 3/5085* (2013.01); *B01L 3/5088* (2013.01);
(Continued)

(58) Field of Classification Search
CPC ............... C12M 25/01; C12Q 1/6883; C12Q 2563/159; C12Q 2565/501; C12Q 1/6825;
(Continued)

(56) References Cited

U.S. PATENT DOCUMENTS

| 8,184,284 B2 | 5/2012 | Ebstein |
| 8,268,551 B2 | 9/2012 | Tong |

(Continued)

FOREIGN PATENT DOCUMENTS

| WO | 2011109440 A1 | 9/2011 |
| WO | 2013110146 A2 | 8/2013 |

(Continued)

OTHER PUBLICATIONS

Choi et al., "Cell interactiuon with three-dimensional sharp-tip namotopography", Biomaterials 28, 2007, pp. 1672-1679.
(Continued)

*Primary Examiner* — Betty J Forman
(74) *Attorney, Agent, or Firm* — Perkins Coie LLP

(57) ABSTRACT

Methods, systems, and devices are disclosed for enrichment and detection of molecules of a target biomarker. In one aspect, In one aspect, a biosensor device for enriching and detecting biomarker molecules include a substrate, and a microarray of hydrophilic islands disposed on the substrate. A sensing area on each of the microarray hydrophilic islands is structured to anchor bio-molecular probes of at least one type for detecting molecules of a target biomarker and to attract an array of nanodroplets of a biomarker solution that
(Continued)

includes the target biomarker molecules. A hydrophobic surface is disposed to surround the microarray of hydrophilic islands.

16 Claims, 34 Drawing Sheets

Specification includes a Sequence Listing.

Related U.S. Application Data

(60) Provisional application No. 61/893,532, filed on Oct. 21, 2013.

(51) Int. Cl.
*B01L 3/00* (2006.01)
*C12Q 1/6825* (2018.01)
*C12Q 1/6837* (2018.01)

(52) U.S. Cl.
CPC ......... *C12Q 1/6825* (2013.01); *C12Q 1/6837* (2013.01); *B01L 2300/0636* (2013.01); *B01L 2300/0819* (2013.01); *B01L 2300/0887* (2013.01); *B01L 2300/161* (2013.01); *B01L 2300/166* (2013.01); *C12Q 2600/178* (2013.01)

(58) Field of Classification Search
CPC ... C12Q 1/6837; B01L 3/5085; B01L 3/5088; B01L 2300/161
See application file for complete search history.

(56) References Cited

U.S. PATENT DOCUMENTS

| | | | |
|---|---|---|---|
| 2003/0096033 A1 | 5/2003 | Mattie et al. | |
| 2003/0138941 A1* | 7/2003 | Gong | B01L 3/5027 435/287.2 |
| 2003/0143571 A1 | 7/2003 | Sharp et al. | |
| 2003/0194709 A1* | 10/2003 | Yang | B01J 19/0046 506/43 |
| 2004/0022692 A1 | 2/2004 | Ermantraut et al. | |
| 2004/0258832 A1 | 12/2004 | Barklund et al. | |
| 2005/0003366 A1* | 1/2005 | Getts | C12Q 1/6837 435/6.11 |
| 2008/0153134 A1* | 6/2008 | Wiyatno | B01J 19/0046 435/91.2 |
| 2008/0254448 A1* | 10/2008 | Ginot | C12Q 1/6837 435/6.11 |
| 2008/0268440 A1 | 10/2008 | Liu et al. | |
| 2008/0314746 A1* | 12/2008 | Ishige | G01N 33/492 204/403.01 |
| 2009/0289213 A1 | 11/2009 | Pipper et al. | |
| 2011/0111984 A1 | 5/2011 | Nakatani et al. | |
| 2012/0135874 A1* | 5/2012 | Wang | C12Q 1/6844 506/9 |
| 2013/0194709 A1 | 8/2013 | Busca et al. | |
| 2014/0378339 A1 | 12/2014 | Lammertyn et al. | |
| 2015/0065390 A1 | 3/2015 | Bratkovski et al. | |
| 2016/0258020 A1 | 9/2016 | Lo et al. | |
| 2018/0264466 A1 | 9/2018 | Lo et al. | |

FOREIGN PATENT DOCUMENTS

| | | |
|---|---|---|
| WO | 2014052685 A2 | 4/2014 |
| WO | 2016112344 A1 | 7/2016 |

OTHER PUBLICATIONS

Hsu et al., "Fabrication and characteristics of black silicon for solar cell applications: An overview", Materials Science in Semiconductor Processing, 2004, pp. 2-17.

Kim, et al., "Size-controllable quartz nanoparticle for signal enhancement of DNA chip," Biosensors and Biolelectronics, 25:2085-2089, Sep. 16, 2010.

Qiao, W. et al., "Oil-Encapsulated Nanodroplet Array for Biomolecular Detection", Annals of Biomedical engineering, vol. 42, No. 9, 2014, pp. 1932-1941.

Tiwari, P. et al., "Functionalized Gold Nanoparticles and Their Biomedical Applications", Nanomaterials, 2001, vol. 1, pp. 31-63.

International Search Report and Written Opinion for PCT Application No. PCT/US2016/012736, dated Apr. 22, 2016, 11 pages.

International Search Report and Written Opinion of International Application No. PCT/US2014/061639; dated Feb. 5, 2015.

* cited by examiner

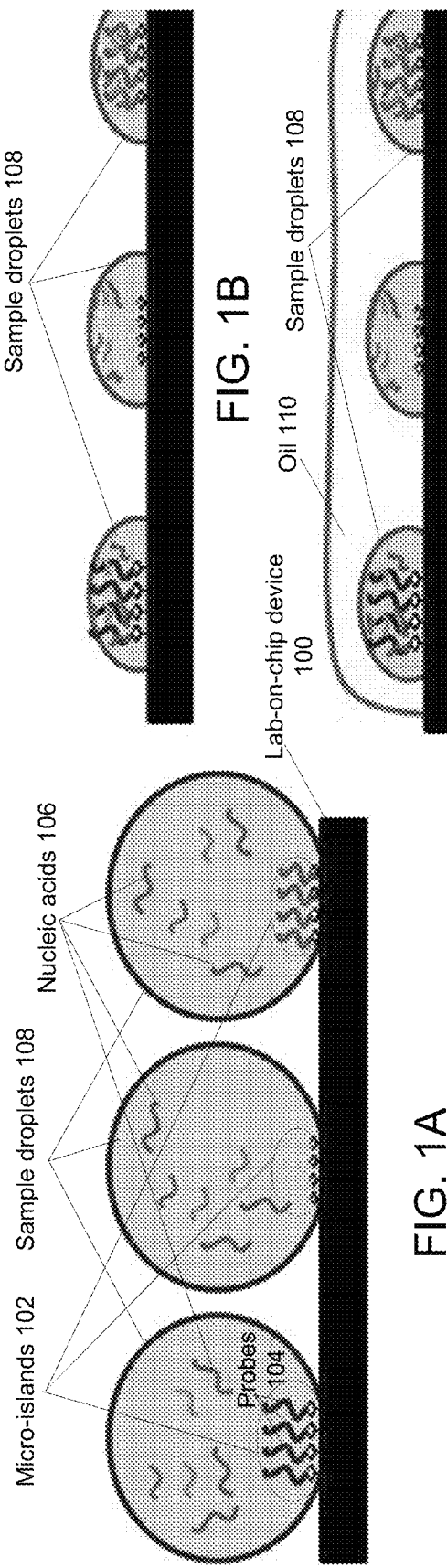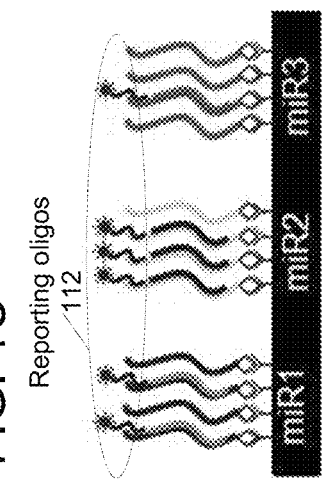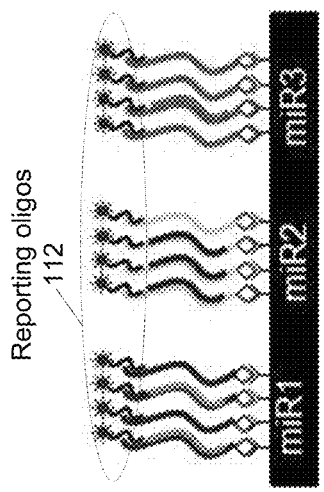

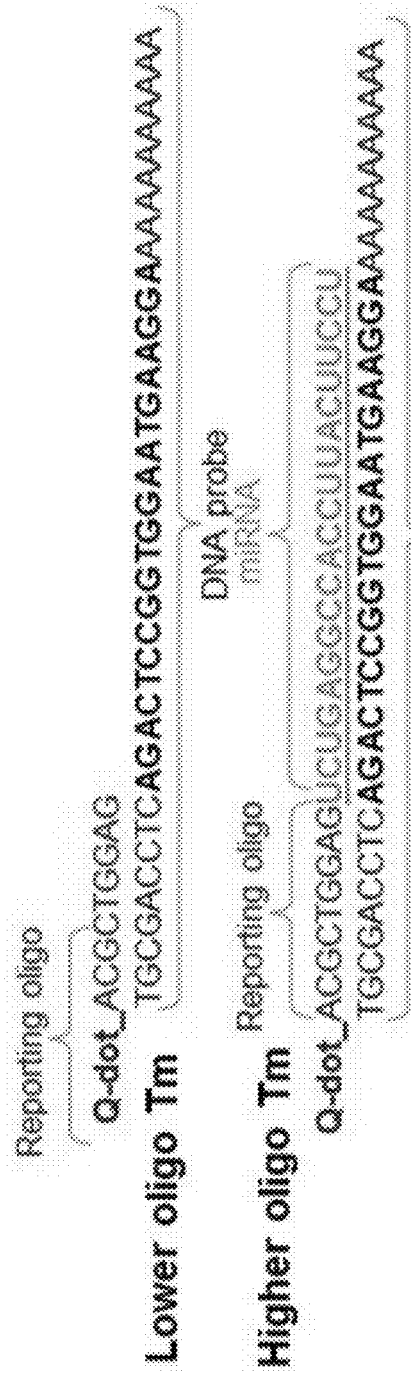
FIG. 21A
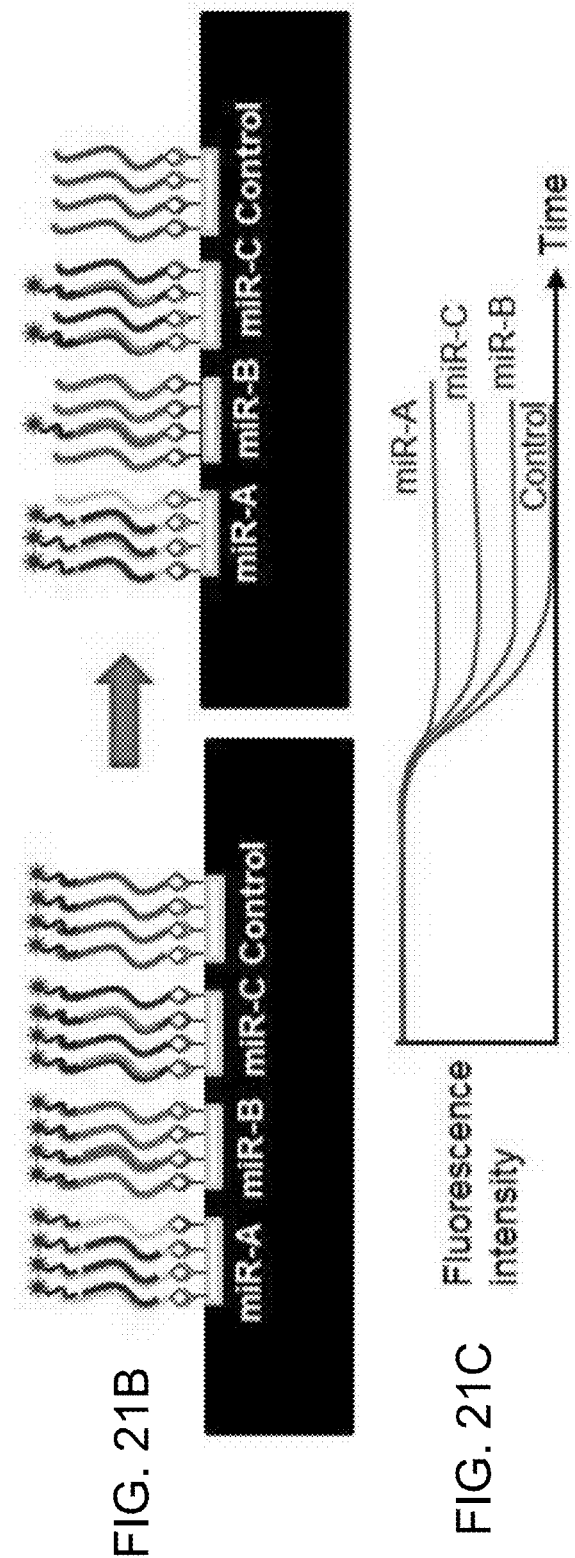
FIG. 21B
FIG. 21C

Teflon Mold-assisted enrichment from 1mL to 5 uL at 95 °C

Enrichment from 5uL to dry at 50 °C

ENRICHMENT AND DETECTION OF NUCLEIC ACIDS WITH ULTRA-HIGH SENSITIVITY

PRIORITY CLAIM AND RELATED PATENT APPLICATION

This patent document is a divisional application of U.S. patent application Ser. No. 15/031,062 entitled "ENRICHMENT AND DETECTION OF NUCLEIC ACIDS WITH ULTRA-HIGH SENSITIVITY" filed on Apr. 21, 2016, which is a 371 National Phase Application of PCT Application No. PCT/US2014/061639 entitled "ENRICHMENT AND DETECTION OF NUCLEIC ACIDS WITH ULTRA-HIGH SENSITIVITY" filed on Oct. 21, 2014, which claims priority to and the benefit of U.S. Provisional Application No. 61/893,532 entitled "METHODS AND DEVICES FOR ENRICHMENT AND DETECTION OF NUCLEIC ACIDS" filed Oct. 21, 2013, the entire contents of which are incorporated by reference in this document.

SEQUENCE LISTING

The instant application contains a Sequence Listing which has been filed electronically in ASCII format and is hereby incorporated by reference in its entirety. Said ASCII copy, created on Feb. 13, 2019, is named 009062-8269_US02_SL.txt and is 1,915 bytes in size.

TECHNICAL FIELD

This patent document relates to biosensor technologies and analytical devices.

BACKGROUND

A biological sensor or biosensor is an analytical tool that can detect a chemical, substance, or organism using a biologically sensitive component coupled with a transducing element to convert a detection event into a signal for processing and/or display. Biosensors can use biological materials as the biologically sensitive component, e.g., such as biomolecules including enzymes, antibodies, aptamers, peptides, nucleic acids, etc., or small molecules such as carbohydrates, as well as virus and living cells. For example, molecular biosensors can use specific chemical properties or molecular recognition mechanisms to identify target agents. Biosensors can use the transducer element to transform a signal resulting from the detection of an analyte by the biologically sensitive component into a different signal that can be addressed by a suitable transduction mechanism, for example, electrical, magnetic, mechanical, physicochemical, electrochemical, optical, piezoelectric, or others.

Detection of low abundance biomolecules is challenging for biosensors that rely on surface chemical reactions. For surface reaction based biosensors, it often takes hours or even days for biomolecules of diffusivities in the order of $10^{-10\text{-}11}$ m$^2$/sec to reach the surface of the sensors through Brownian motion. Moreover, the repulsive Coulomb interactions between the molecules and the probes can further defer the binding process, leading to undesirably long detection time for applications such as point-of-care in-vitro diagnosis.

SUMMARY

Techniques, systems, and devices are disclosed for enrichment and detection of biomarker molecules including nucleic acids.

The subject matter described in this patent document can be implemented in specific ways that provide one or more of the following features. For example, the disclosed devices and systems are capable of enriching and detection of biomarkers molecules, e.g., such as DNAs and RNAs, without requiring any amplification steps to increase the copy number of those molecular markers. Such devices are especially attractive to a variety of applications, for example, including, but not limited to, gene expression analysis by estimating the copy numbers of cDNA or mRNA transcripts present in the sample; applications in molecular detection, nucleic acid biomarker quantification for clinical, laboratory and point-of-care diagnostic purposes; development to detect pathogen and infectious disease with direct identification of endogenous sequences, including fragmental microbial genome (DNA) and retroviral RNA sequences; capability to quantify miRNA and other forms of circulating epigenetic marker for early diagnosis of disease and injury; and mutational analysis of cancer and hereditary diseases using tiling probes layout.

In one aspect, a biosensor device for enriching and detecting biomarker molecules include a substrate, and a microarray of hydrophilic islands disposed on the substrate. A layer of silicon oxide (SiO2) is disposed over the microarray of hydrophilic islands to form a sensing area on the microarray hydrophilic islands, the sensing areas are structured to anchor bio-molecular probes of at least one type for detecting molecules of a target biomarker and to attract an array of droplets of a biomarker solution that includes the target biomarker molecules. A super-hydrophobic surface is disposed to surround the microarray of hydrophilic islands. The super-hydrophobic surface include nanostructures having rough surfaces to enrich the target biomarker molecules on the sensing area by enhancing evaporation of the array of droplets leading to an enriched array of droplets with an increased concentration of the target biomarker molecules compared to before evaporation. The sensing area is structured to receive a layer of water-immiscible-liquid over the enriched array of droplets to form water-immiscible-liquid encapsulated reaction chambers (e.g., nano or microliter volume) for controlling a reaction between the target biomarker molecules and the bio-molecular probes. In one embodiment, the water-immiscible-liquid includes oil. In one embodiment, each droplet is nanoliter or less.

The biosensor can be implemented in various ways to include one or more of the following features. The nanostructures of the super-hydrophobic surface can include nanopillars. The sensing area can be structured to receive a labeling material to label target biomarker molecules that reacted with the bio-molecular probes. The labeling material can include quantum dots. The hydrophilic property of the SiO2 layer can cause the array of droplets to be self-aligned with the sensing area. The SiO2 layer covered microarray of hydrophilic islands and the nanostructures of the super-hydrophobic surface can be disposed to have a height difference that reduces adhesion of target biomolecules to a sidewall of the SiO2 layer covered microarray of hydrophilic islands during evaporation. The super-hydrophobic surface can include black silicon. The bio-molecular probes of at least one kind can include DNA probes and the target biomarker molecules can include target nucleic acids. The sensing areas of the microarray of hydrophilic islands can be structured to enrich and detect different types of target biomarker molecules. The biosensor device can detect the biomarker molecules of approximately 0.5 femtomolar (fM) concentration. The biosensor device can enrich and detect multiple biomarker molecule types in parallel. The multiple types of biomarker molecules can include RNA and DNA markers. In one embodiment, each droplet is nanoliter or less In another aspect, a method performed by a biosensor device to enrich and detect biomarker molecules includes receiving, by a biosensor device including a microarray of hydrophilic islands having sensing surfaces and surrounded by hydrophobic nanostructures, bio-molecular probes of at least one type for detecting molecules of a target biomarker to functionalize the sensing surfaces of the microarray of hydrophilic islands. The method includes receiving, over the functionalized sensing surfaces of the microarray of hydrophilic islands, droplets of a biomarker solution that includes the biomarker molecules to form an array of droplets of the biomarker solutions on the functionalized sensing surfaces. The method includes receiving over the array of droplets of the biomarker solutions a layer of water-immiscible-liquid to encapsulate the array of droplets of the biomarker solutions to form water-immiscible-liquid encapsulated reaction chambers (e.g., nano or microliter volume) for controlling a reaction between the target biomarker molecules and the bio-molecular probes. In one embodiment, the water-immiscible-liquid includes oil. In one embodiment, each droplet is nanoliter or less.

The method can be implemented in various ways to include one or more of the following features. The bio-molecular probes of at least one type can include DNA probes, and the molecules of biomarkers can include nucleic acids. The DNA probes can include DNA oligonucleotides. Receiving the layer of water-immiscible-liquid to encapsulate the array of droplets of the biomarker solutions to form water-immiscible-liquid encapsulated reaction chambers (e.g., nano or microliter volume) for controlling a reaction between the target biomarker molecules and the bio-molecular probes can include facilitating hybridization of the biomarker molecules with the DNA probes within the reaction chambers (e.g., nano or microliter volume). The method can include receiving labeling materials to within the reaction chambers (e.g., nano or microliter volume) to label bio-molecular probe attached biomarker molecules formed responsive to the controlled reaction. The labeling materials can include quantum-dots. The nucleic acids can include DNA, RNA or miRNA-based nucleic acids. The sensing areas can include a layer of silicon oxide (SiO2). The super-hydrophobic surface can include black silicon. The target biomarker molecules can include fluorescently labeled biomarker molecules to determine a concentration of the target biomarker molecules based on a fluorescent intensity of the fluorescently labeled biomarker molecules that react with bio-molecular probes. In one embodiment, the water-immiscible-liquid includes oil. In one embodiment, each droplet is nanoliter or less.

In another aspect, a technique is described for enriching biomarker molecules within a biosensor to facilitate ultra-sensitive detection and quantification of the biomarker molecules without an amplification of the biomarker molecules. This technique includes mixing a sample containing biomarker molecules with a hybridization buffer containing DNA oligo probes to form a biomarker solution; and dispensing droplets of the biomarker solution onto a device containing an array of micro-islands or microarray of islands surrounded and separated by a hydrophobic surface. The surface of each micro-island is functionalized with a set of DNA oligo probes, and each droplet is dispensed onto a separate micro-island to form a droplet array of the biomarker solution which substantially coincides with the microarray of islands or array of micro-islands. The technique includes evaporating the droplet array to increase a concentration of the biomarker molecules within each of the evaporated droplets as a result of reducing volume of the droplet. When the droplet array has evaporated to a thin layer of the biomarker solution, the technique includes encapsulating the droplet array in a layer of water-immiscible-liquid to stop the evaporation and to facilitate the biomarker molecules within the droplet array to hybridize with the DNA oligo probes within the microarray of islands or array of micro-islands. The technique includes attaching quantum-dots linked reporting DNA oligos to the set of DNA oligo probes within each of the micro-islands; and subsequently selectively removes a subset of the hybridized reporting DNA oligos from a corresponding subset of the DNA oligo probes which are not hybridized with the biomarker molecules. After the removal of the subset of the reporting DNA oligos, the number of the quantum-dots linked reporting oligos within each of the micro-islands is substantially equal to the number of the hybridized biomarker molecules within the same micro-island. The technique includes detecting and quantifying concentration of the hybridized biomarker molecules by either measuring a fluorescent intensity of each micro-island caused by the remaining quantum-dots or by counting the number of the remaining quantum dots using an image processing software. In one embodiment, the water-immiscible-liquid includes oil.

In another aspect, a technique is described for enriching biomarker molecules within a biosensor to facilitate ultra-sensitive detection and quantification of the biomarker molecules without an amplification of the biomarker molecules. This technique includes providing a device containing an array of sensing micro-islands surrounded and separated by a hydrophobic surface. The surface of each sensing micro-island is functionalized with a set of DNA oligo probes. The technique includes mixing a sample containing biomarker molecules with a hybridization buffer containing DNA oligo probes to form a biomarker solution. The technique includes dispensing droplets of the biomarker solution onto the surface of the device such that each droplet is dispensed onto a separate sensing micro-island to form a droplet array of the biomarker solution which substantially coincides with the array of sensing micro-islands. The technique includes evaporating the droplet array to increase a concentration of the biomarker molecules within each of the droplets as a result of reducing volume of the droplet. When the droplet array has evaporated to a thin layer of the biomarker solution, the technique encapsulates the droplet array in a layer of oil to stop the evaporation and to facilitate the biomarker molecules within the droplet array to hybridize with the DNA oligo probes within the array of sensing micro-islands. The technique next removes the layer of oil and the hybridization buffer to expose the DNA oligo probes, a subset of the DNA oligo probes are hybridized with the biomarker molecules. The technique labels the subset of the DNA oligo probes with quantum-dots linked reporting DNA oligos. After labeling the subset of the DNA oligo probes, the number of the quantum-dots linked reporting oligos within each of the sensing micro-islands is substantially equal to the number of the hybridized biomarker molecules within the same sensing micro-island.

In another aspect, a technique for enriching biomarker molecules within a biosensor to facilitate ultra-sensitive detection and quantification of the biomarker molecules without an amplification of the biomarker molecules is disclosed. This technique includes providing a device containing an array of sensing micro-islands surrounded by a hydrophobic surface and separated by a grid of pillars. The surface of each sensing micro-island is functionalized with a set of DNA oligo probes. The technique includes dispensing a biomarker molecules containing solution over the device to cover the array of sensing micro-islands and subsequently evaporates the solution over the array of sensing micro-islands to concentrate the biomarker molecules onto the sensing micro-islands. The technique includes dipping the device containing the condensed biomarker molecules in a hybridization buffer containing a suspension of quantum-dots linked reporting DNA oligos for a specific time (e.g., 1 second) to form an array of self-assembled nano-droplets (e.g., nanoliter volume or less) to immerse the concentrated biomarker molecules on the sensing micro-islands. The technique includes encapsulating the nano-droplets (e.g., nanoliter volume or less) with a layer of water-immiscible-liquid to form an array of hybridization reaction chambers (e.g., nano or microliter volume), which facilitate hybridization both between the biomarker molecules and the DNA oligo probes and between the DNA oligo probes and the quantum-dots linked reporting DNA oligos. The technique includes selectively removing a subset of the hybridized reporting DNA oligos from a corresponding subset of the DNA oligo probes which are not hybridized with the biomarker molecules. After the removal of the subset of the reporting DNA oligos, the number of the quantum-dots linked reporting oligos within each of the hydrophilic islands is substantially equal to the number of the hybridized biomarker molecules within the same hydrophilic island. The technique includes detecting and quantifying concentration of the hybridized biomarker molecules by either measuring a fluorescent intensity of each micro-island caused by the remaining quantum-dots or by counting the number of the remaining quantum dots using an image processing software. In one embodiment, the water-immiscible-liquid includes oil.

In yet another aspect, a technique for enriching biomarker molecules within a biosensor to facilitate ultra-sensitive detection and quantification of the biomarker molecules without an amplification of the biomarker molecules is disclosed. This technique includes providing a device containing an array of sensing micro-islands surrounded and separated by a hydrophobic surface and separated by a grid of pillars. The surface of each sensing micro-island is functionalized with a set of DNA oligo probes. The technique includes dispensing a solution of the biomarker molecules solubilized in a hybridization buffer over the device to form droplets of the biomarker molecules that cover the array of sensing micro-islands. The technique includes evaporating the droplets of the biomarker molecules, and while evaporating, each of the droplets of the biomarker molecules realigns with a corresponding hydrophilic sensing island in the array of hydrophilic sensing islands, reduces in size, concentrates, and become dry. The technique includes dipping the device containing the condensed droplets in water for a specific time to form an array of self-assembled nano-droplets (e.g., nanoliter volume or less) to immerse the concentrated biomarker molecules on the sensing micro-islands. The technique includes encapsulating the array of nano-droplets (e.g., nanoliter volume or less) with a layer of water-immiscible-liquid to form an array of hybridization chambers (e.g., nano or microliter volume), which facilitate hybridization between the biomarker molecules and the DNA oligo probes. The technique includes removing the layer of water-immiscible-liquid to expose the DNA oligo probes, and a subset of the DNA oligo probes are hybridized with the biomarker molecules. The technique includes labeling the subset of the DNA oligo probes with quantum-dots linked reporting DNA oligos. After labeling the subset of the DNA oligo probes, the number of the quantum-dots linked reporting oligos within each of the sensing micro-islands is substantially equal to the number of the hybridized biomarker molecules within the same sensing micro-island. The technique includes detecting and quantifying concentration of the hybridized biomarker molecules by either measuring a fluorescent intensity of each micro-island caused by the remaining quantum-dots or by counting the number of the remaining quantum dots using an image processing software. In one embodiment, the water-immiscible-liquid includes oil.

BRIEF DESCRIPTION OF THE DRAWINGS

FIG. 1A shows a schematic illustrating an exemplary process of dispensing nucleic acid (e.g., miRNA)-containing droplets onto microarray of island (or micro-islands) with specific DNA oligo probes.

FIG. 1B show a schematic illustrating an exemplary nucleic acid enrichment process by evaporating the sample droplets.

FIG. 1C show a schematic illustrating an exemplary process of encapsulating the thin layer of nucleic acid enriched liquid in oil to form highly efficient hybridization chambers.

FIG. 1D shows a schematic illustrating an exemplary process of hybridizing nucleic acids (e.g., miRNAs) with the specific probes on each of the microarray of island (or micro-islands).

FIG. 1E shows a schematic illustrating an exemplary process of attaching quantum-dots linked reporter oligos to all the probes.

FIG. 1F shows a schematic illustrating an exemplary process of using the stacking effect to selectively remove those reporter oligos from a subset of probes which did not hybridize with the target nucleic acids.

FIG. 4A discloses SEQ ID NOS 5, 6, and 5, respectively, in order of appearance.

FIG. 21A shows an exemplary design of a DNA probe and Q-dot linked reporter oligo. The stacking effect produces a melting temperature difference for the reporter oligo between miRNA hybridized and unhybridized probes. FIG. 21A discloses SEQ ID NOS 5, 6, and 5, respectively, in order of appearance.

FIG. 21B shows an exemplary device schematic for detection and quantification of different miR cancer markers and the on-chip negative control, and the process of using the stacking effect to selectively remove the Q-dot linked reporter oligos from probes without hybridized target miRNAs.

FIG. 21C shows an exemplary plot of anticipated time-dependent fluorescent signals from each specific miR cancer marker shown in FIG. 21B and the control signal.

DETAILED DESCRIPTION

Introduction and Overview

Figure 2C:
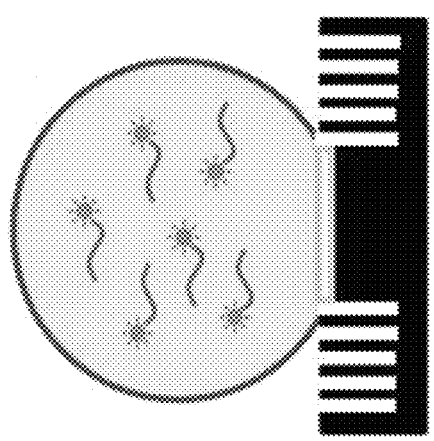
FIG. 2C shows a schematic illustration of a micro droplet positioned on the exemplary black Si template.

Identification of nucleic acid markers such as DNA, RNA, specially miRNAs from blood, biofluids, and cerebrospinal fluid (CSF) can be achieved by sequencing, quantitative-PCR, and liquid chromatography-mass spectrometry analysis. However, these techniques require sample enrichment via amplification, which can incur significant burden in time and cost. For example, polymerase-based amplification has to be accomplished by thermal cycling and enzymatic reactions, which is not practical for the purpose of time-sensitive clinical diagnosis. In addition, enzymatic amplification introduces inevitable bias toward specific sequences that greatly compromises the accuracy of the diagnosis. The disclosed technology provides advantages over conventional techniques and devices for nucleic acid detection and enrichment.

Blood and biofluids contain many biomolecules, including proteins, DNAs, and RNAs, that can be used as biomarkers for disease diagnosis. However, low concentration levels of these biomarkers often make accurate and rapid detection challenging. For instance, one needs to detect circulating miRNAs at concentrations as low as 10 to 100 femtomolar (fM) for cancers, traumatic brain injuries, cardiovascular diseases, etc. Most of the surface reaction-based biosensors and DNA microarrays have a detection limit of picomolar (pM), even when the most advanced detection technologies are used (e.g., with fluorescence, current, or SPR). The detection sensitivity is largely limited by the diffusion process when the concentration of the target biomarkers drops to fM range because the flux of diffusion is lowered by the decreasing concentration. The technology disclosed in this patent document includes detection techniques that can potentially overcome the diffusion limit to allow accurate and rapid detection of low concentrations of biomarkers.

Evaporating droplets (e.g., droplets that are nanoliter or less) may be used to enrich target molecules. In one implementation, a droplet device is used to concentrate DNAs by $1 \times 10^4$ fold. However, the detection position and the sensing area are difficult to control for reproducible performance. Also the dried DNAs resulted from this technique are difficult to be identified from the background noise. In another implementing, a microchip is used where the evaporation of DNA droplets takes place simultaneously with hybridization. In this approach, the salt concentration continues to increase with the shrinking volume of the droplet during the hybridization process, making the control of hybridization conditions, especially the salt concentration, temperature, and reaction time, rather difficult. Moreover, the sample may be dried up before the reaction is complete. These factors have limited the detection sensitivity of such device to around 100 pM. In yet another implementation, a two-stage enrichment device is developed where the target nucleic acids are first captured by microbeads and then dried for fluorescent detection. By separating the molecular enrichment step from the detection step, this approach has improved the overall device performance to pM sensitivity. However, this approach still does not enable precise control of the hybridization conditions to reach the sensitivity required for certain point-of-care in-vitro diagnostic applications.

Techniques, devices, and systems are disclosed for enriching and detecting a sample target molecule, that includes nucleic acids (also referred to as "the disclosed technology"). In some implementations, the disclosed technology provides a chip-based device that can concentrate nucleic acids in a fluidic sample on-chip. Such a chip-based device can be used to dramatically lower the miRNA detection limit below existing technologies to reach 1 femtomolar level. The disclosed techniques can be implemented without using any enzymatic reagents, and thus presents itself as a viable technology for miRNA-based point-of-care and clinical diagnosis solution to date.

The disclosed technology includes an water-immiscible-liquid (e.g., oil)-encapsulated evaporating droplet (e.g., droplet that is nanoliter or less) array on a microchip that can detect molecules at a concentration of fM range. Templates having surface properties that support the droplets have been engineered to allow the droplets to be self-aligned with the sensing areas to facilitate the binding or hybridization process. The disclosed technology further utilizes evaporation for pre-concentration of the detection targets to greatly shorten the reaction time and enhance the detection sensitivity. In the disclosed technology, the evaporation process of the droplets may be facilitated by the hydrophobic or superhydrophobic surface and resulting nano-droplets (e.g., nanoliter volume or less) can be encapsulated by water-immiscible-liquid (e.g., oil) drops to form stable reaction chamber (e.g., nano or microliter volume). To further enhance the sensitivity and specificity, a technique has been developed to have the target enrichment and molecular detection in the same areas of the device without intrachip or interchip sample transfer. Using the disclosed technology, desirable droplet volumes, concentrations of target molecules, and reaction conditions (salt concentrations, reaction temperature, etc.) in favor of fast and sensitive detection can be obtained. In some implementations, a linear response over 2 orders of magnitude in target concentration can be achieved at 10 fM for protein targets and 100 fM for miRNA mimic oligonucleotides.

Techniques, devices, and systems of the disclosed technology include: (1) lab-on-a-chip device architecture to perform enrichment and detection of a sample containing nucleic acids, without miRNA-specific label; (2) an evaporating droplet technique to enrich the nucleic acid biomarkers such as miRNAs; (3) water-immiscible-liquid (e.g., oil)-encapsulated reaction chambers (e.g. nano or micro-liter volume) for efficient and reproducible nucleic acid hybridization; and (4) detection and quantification techniques of DNAs or RNAs using a "stacking effect". Implementations of the disclosed technology can facilitate achieving: (1) parallel operation with multiple samples; (2) simultaneous detection of multiple RNA/DNA disease markers; (3) large enrichment without amplification; and (4) femtomolar sensitivity with high accuracy and specificity.

The disclosed technology can be used for enriching and detection of biomarkers molecules, such as DNAs and RNAs, without requiring any amplification steps to increase the copy number of those molecular markers. Such devices and systems are especially attractive to a variety of applications including, but not limited to: gene expression analysis by estimating the copy numbers of cDNA or mRNA transcripts present in the sample; applications in molecular detection, nucleic acid biomarker quantification for clinical, laboratory and point-of-care diagnostic purposes; development to detect pathogen and infectious disease with direct identification of endogenous sequences, including fragmental microbial genome (DNA) and retroviral RNA sequences; capability to quantify miRNA and other forms of circulating epigenetic marker for early diagnosis of disease and injury; and mutational analysis of cancer and hereditary diseases using tiling probes layout.

The disclosed lab-on-a-chip detection technique and device can be used for early stage cancer/precancerous detection from circulating extra-cellular vesicle (EV) encapsulated miRNAs in blood, biofluids, or cerebrospinal fluid (CSF), allowing rapid and accurate diagnosis at a fraction of current cost. The disclosed detection technique is highly sensitive, reliable and requires no amplification, thus removing any bias associated with the amplification process. The disclosed device is compact, easy to use, low cost, and quick in producing test results from a small sample amount. Hence, the disclosed detection technique and device provide a platform technology applicable to miRNA and DNA biomarkers for various cancer types/subtypes.

In one aspect, capabilities for providing enhanced sensitivity relative to sequencing and PCR assays are added to the hybridization-based assays that provide advantages in amplification free, low infrastructural cost and high-throughput capabilities. For example, the disclosed technology can provide for a massively parallel nano-droplet (e.g., nanoliter volume or less) microarray system and device with detection limit as low as 50 aM. Some embodiments of the disclosed system and device incorporate a micro-patterned super-hydrophobic black silicon surface that enriches nucleic acid samples by rapid evaporation and self-assembled nano-droplet (e.g., nanoliter volume or less) array formation. In addition of achieving an unprecedented atto-molar (aM) level sensitivity performance, some embodiments of the disclosed system and device can also exhibit a 6 orders of linear dynamic range and rapid hybridization time of 5 min. As a platform technology, it can be applied to a large number of research and clinical applications, including point-of-care disease diagnosis, real-time pathogen detection, and microRNA based early-stage cancer diagnosis and prognosis.

For nucleic acid detection and quantification, PCR-based amplification assay and next generation sequencing can provide enhanced sensitivity over other techniques such as hybridization-based microarray. However, PCR-based assay such as quantitative real-time PCR can only provide semi-quantitative result. While digital PCR can potentially provide absolute quantification, the throughput remains low. Next generation sequencing has high infrastructural cost and is non-quantitative, and remains a tool for discovering new DNA fragments and microRNAs. In comparison, microarray can provide the point-of-care capability with its amplification-free process, high throughput lacked by PCR-based assays, and significantly lower infrastructural cost that undermines next generation sequencing. The disclosed technology can provide microarrays with enhanced sensitivity, high dynamic range, and short hybridization time while providing an absolute quantification.

Nano-particles labeling, elaborate nucleic acid probe design, surface chemistry, electrochemistry, or microfluidic design at the labeling and detection step of the assay can be improved. Currently, the limit of detection from these approaches stands at 1-100 fM, and a dynamic range of 3-4 orders. In comparison to previous attempts, the disclosed technology provides innovations in the hybridization step prior to labeling and detection. Using the disclosed technology, a self-assembled nano-liter droplet microarray device has been designed to demonstrate a detecting limit of 50 aM. In some implementations, the disclosed device includes hydrophilic (e.g., $SiO_2$, metal, dielectrics, or other hydrophilic materials) patterns surrounded by micro- or nano-patterned, hydrophobic or super-hydrophobic, black silicon surface. Nucleic acid samples can be enriched and hybridized on such a device via rapid evaporation followed by self-assembled nano-droplet (e.g., nanoliter volume or less) formation. Within the nano-liter droplets, the hybridization reaction proceeds to completion rapidly due to the reduced volume, resulting in accelerated hybridization time. Moreover, the precise volume control offered by self-assembled nano-droplet (e.g., nanoliter volume or less) array allows for a wide range of control over enrichment ratio, resulting in higher sensitivity and extended dynamic range. The hybridized nucleic acid samples have been biotin-labeled and visualized by binding to quantum dots for absolute quantification. However, the proposed platform technology can be combined with other labeling and detection technique.

In one aspect, the disclosed technology can potentially provide for a 200,000 fold enrichment of the sample nucleic acid, and a self-assembled nano-liter droplet platform suitable for massively parallel processes. Such a self-assembled nano-liter droplet microarray system can have a detecting limit at 50 aM (50 zmol), 6 orders of linear dynamic range, and a hybridization time of approximately 5 minutes. As a platform technology, the nano-liter droplet microarray is suitable for point-of-care application as it does not require sample amplification, and can be applied to many research and clinical assays that detect and quantify short nucleic acid.

Clinically relevant short nucleic acids biomarkers such as viral and bacterial DNA fragments are routinely used to diagnose infectious diseases such as tuberculosis (TB), human immunodeficiency virus (HIV), methicillin-resistant *staphylococcus aureus* (MRSA), and group B *streptococcus* (GBS). The other class of clinically relevant short nucleic acid, microRNAs, are regulatory RNAs ~22 nucleotides in length, and can be extracted from plasma, serum, tissue, and cells. MircoRNAs are exceptional biomarkers for central nervous system injuries, cardiovascular diseases, and cancer diagnosis and prognosis. Most microRNAs studies on cancer and cardio-vascular diseases report microRNA concentration ranging from 1 fM to 1 pM. Consequently, with a detecting limit of 50 aM and 6 orders of linear dynamic range without sample amplification, the disclosed system and device provide a promising outlook for microRNA quantification, point-of-care infectious disease diagnosis, and real-time pathogen detection.

Exemplary Device Architecture and Process Flow

In one example, a device can handles nucleic acids (e.g. miRNAs) in biofluids. For miRNAs that are contained within extra-cellular vesicles or attached to Aga-protein in blood, biofluids, or CSF, they can be extracted using standard DNA/RNA extraction kits. The disclosed molecular enrichment and detection devices can solve the technology bottleneck, e.g., such as for nucleic acid biomarker enrichment and detection.

FIGS. 1A-1F show schematics illustrating an exemplary process for enriching and detection of biomarker molecules, such as DNAs and RNAs. FIG. 1A shows a schematic illustrating an exemplary process of dispensing nucleic acid (e.g., miRNA)-containing droplets onto microarray of islands or micro-islands with specific DNA oligo probes formed on a lab-on-a-chip device 100. The microarray of islands or micro-islands 102, each containing oligo probes 104, are surrounded by super-hydrophobic surface. Microarray of islands or micro-islands 102 can be hydrophilic islands. As can be seen in FIG. 1A, the nucleic acid 106 containing sample is mixed in diluted hybridization buffer and dispensed onto lab-on-a-chip device 100 in forms of droplets 108.

FIG. 1B shows a schematic illustrating an exemplary nucleic acid enrichment process by evaporating the sample droplets. As can be seen in FIG. 1B, as sample droplets 108 evaporate on the super-hydrophobic surface of lab-on-a-chip device 100 with hydrophilic islands, the nucleic acid concentration increases.

FIG. 1C shows a schematic illustrating an exemplary process of encapsulating the thin layer of nucleic acid enriched liquid in oil to form highly efficient hybridization chambers (e.g., nano or microliter volume). As can be seen in FIG. 1C, when sample droplets 108 are almost completely evaporated, but with a thin layer of sample liquid remaining to covering the hydrophilic islands, oil 110 is added to cover the remaining sample droplets 108, forming a stable microenvironment to facilitate nucleic acid hybridization with the DNA oligo probes. In some embodiments, after the completion of the hybridization, the process also includes removing the layer of oil and the hybridization buffer to expose the DNA oligo probes, as shown in FIG. 1D.

FIG. 1D shows a schematic illustrating an exemplary results of hybridization between nucleic acids (e.g., miRNAs) 106 and DNA probes 104 on each of the microarray of islands or micro-islands 102. In the embodiment shown, the numbers of hybridization between nucleic acids 106 and probes 104 are, 2, 3, and 1 for the three islands from left to right, respectively. The highly enriched nucleic acid within the thin (e.g., 20 μm) layer of the sample liquid renders high and repeatable hybridization efficiency within a short time (e.g., <30 minutes instead of 100 hours), as is discussed in more details below.

FIG. 1E shows a schematic illustrating an exemplary process of attaching quantum-dots (or "Q-dots") linked reporter or "reporting" oligos 112 to some or substantially all the DNA probes 104. As can be seen in FIG. 1E, after washing, reporting DNA oligos 112 linked with quantum dots are introduced. In some embodiments, the introduced reporting DNA oligos 112 have their nucleotide sequence complementary to the first 8 nucleotides of the DNA probes 104 and hybridize with substantially all the DNA probes.

FIG. 1F shows a schematic illustrating an exemplary process of using the stacking effect to selectively remove those reporter oligos 112 from a subset of probes 104 which did not hybridize with the target nucleic acids 106. In one embodiment, after washing away extra reporting DNA oligos linked with Q-dots, the device is heated or experiences shear stress from a relatively strong flow. Because of the "stacking effect", the reporting oligos attached to DNA probes hybridized with a miRNA molecule have a higher melting temperature ($T_m$) than the reporting oligos attached to those DNA probes without miRNA hybridization. As can be seen in FIG. 1F, by utilizing this stacking effect, reporting oligos linked with Q-dots 112 stay only on those probes hybridized with the target nucleic acids. The concentration of the specific target nucleic acids can then be detected and quantified by, for example, measuring the fluorescent intensity of each micro-island (due to the remaining Q-dots) or by counting the number of quantum dots using an image processing software.

Exemplary Techniques for Nucleic Acid Enrichment Using Evaporating Droplets

Some disclosed techniques can be performed to enrich nucleic acid concentrations substantially to detect and quantify low concentrations of nucleic acids without amplification, such as the technique based on the droplet array evaporation described above in conjunction with FIGS. 1A-1F. Prior to performing the technique, a template is fabricated to contain a 2-dimensional (2D) array of hydrophilic islands surrounded by super-hydrophobic surface. FIGS. 2A-2E show images and schematics depicting an exemplary device including a droplet array formed on hydrophilic islands surrounded by super-hydrophobic black Si. FIG. 2 shows the effect of enrichment using evaporating droplets.

Figure 2B:
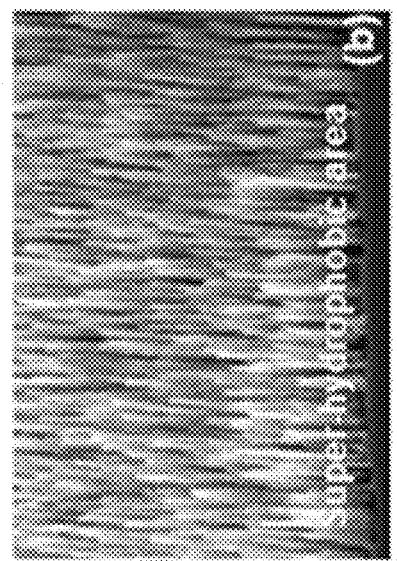
FIG. 2B shows a scanning electron microscopy (SEM) micrograph of an exemplary black Si region on the exemplary black Si template.
Figure 2A:
FIG. 2A shows a photograph of an exemplary droplet array formed on the exemplary black Si template.

FIG. 2A shows a photograph of an exemplary droplet array formed on the exemplary black Si template. FIG. 2B shows a scanning electron microscopy (SEM) micrograph of an exemplary black Si region on the exemplary black Si template. The black Si properties are caused by the nanostructures and the material properties of etched Si. FIG. 2C shows a schematic illustration of a micro droplet positioned on the exemplary black Si template. The yellow area represents the hydrophilic island, which is surrounded by black Si. FIG. 2D shows a photograph of the droplet on the exemplary black Si template with a contact angle of about 155 degrees.

In one embodiment, to form the droplet array shown in FIG. 2A, nucleic acids extracted from the biofluids or blood from patients can be mixed in highly diluted hybridization buffer and dispensed onto the template at an initial droplet volume of 4 μL each and covering a 125 μm diameter hydrophilic island on which specific DNA probes are immobilized. In some embodiments, as the droplets evaporate on the device surface, each droplet volume shrinks and centers at the corresponding hydrophilic island, eventually forming a thin layer of liquid layer (e.g., about 20 μm thick) covering the hydrophilic area for a liquid volume of around 0.4 nL, i.e., achieving 10,000× enrichment. The liquid thickness can be monitored from the top of the device by monitoring the focal length with a low magnification (10×) objective lens or observed and measured from side in a setup similar to the one for the contact angle measurement of liquid droplets. As the nucleic acid concentration reaches the desired level determined by the specific applications and the range of copy number of nucleic acid intended to measure, the evaporation process may be stopped by either oil encapsulation or by controlling the humidity of the microenvironment. For example, if one plans to enrich the nucleic acid from 10 fM to 100 pM (i.e., 10,000× sample enrichment), one may use 10,000× diluted hybridization buffer to form the initial droplet so that the optimal hybridization condition is achieved and maintained when the volume of the droplet is reduced to one ten thousands of the original volume. Next, fluorescently labeled DNA oligos are added to the liquid.

Figure 2E:
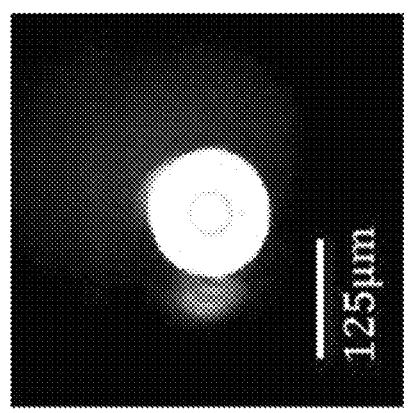
FIG. 2E shows an image demonstrating sample enrichment by evaporating the droplets.
Figure 2D:
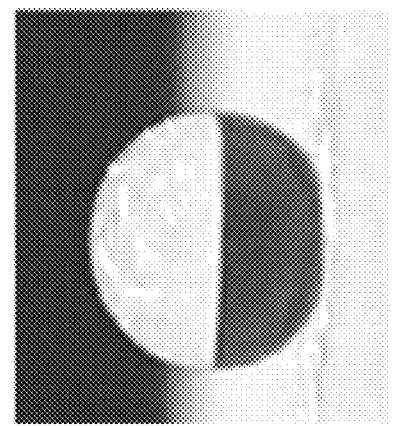
FIG. 2D shows a photograph of the droplet on the exemplary black Si template with a contact angle of about 155 degrees.

FIG. 2E shows an image demonstrating sample enrichment by evaporating the droplets. In the example shown, the fluorescently labeled DNA oligos in a 4 μL (e.g., ~2 mm diameter) droplet are condensed into a ~125 μm diameter hydrophilic surface area. At the end of the enriching process, DNAs are concentrated to the ~125 μm diameter hydrophilic surface, and the surrounding super-hydrophobic black silicon can eliminate the undesirable "coffee ring effect" that traps nucleic acids during the droplet drying process.

Exemplary Oil-Encapsulated Reaction Chambers (e.g., Nano or Microliter Volume) for Efficient miRNA Hybridization The hybridization efficiency between the target nucleic acid and the DNA probe is a significant factor of variation for quantitative detection of nucleic acid (e.g., miRNA) markers. To obtain accurate and repeatable results, the equilibrium state of nucleic acid/DNA binding needs to be obtained. Silicone oil or hexane can be used to encapsulate the thin layer of liquid produced by the evaporated droplet to form a "hybridization chamber" (e.g., nano or microliter volume) to assure high and repeatable hybridization efficiency.

Figure 3A:
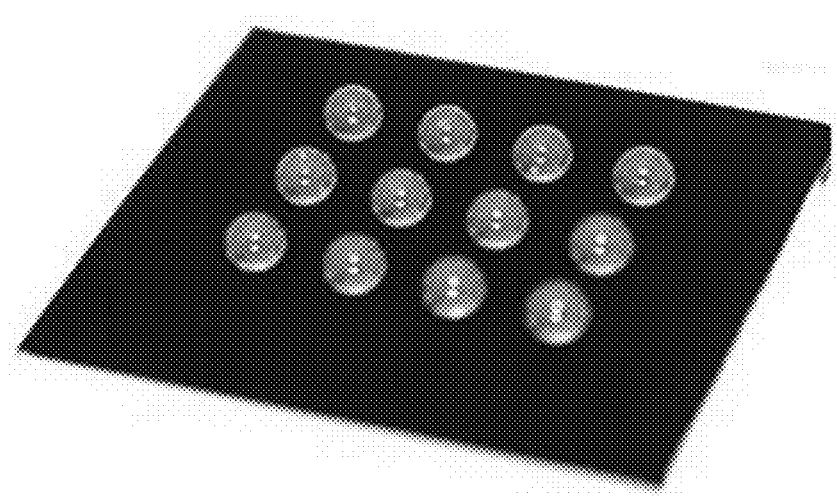
FIG. 3A shows a photographic image of a droplet array dispensed on black Si template without oil encapsulation.
Figure 3B:
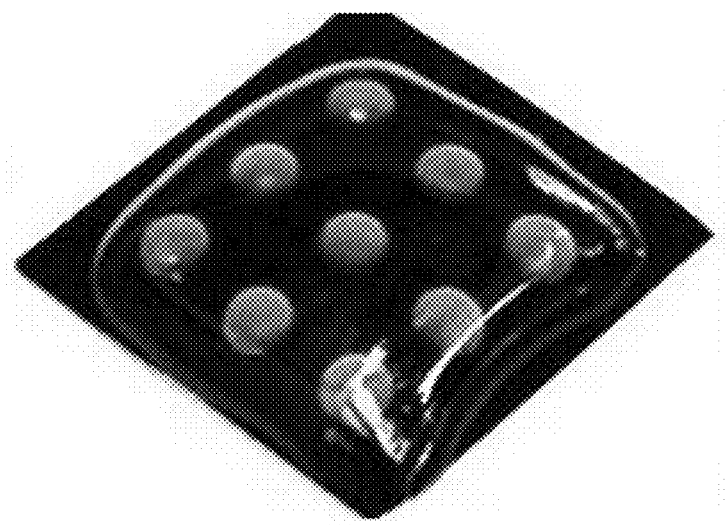
FIG. 3B shows a photographic image of the droplet array in an oil encapsulation after the droplet volume is reduced to about 50% of the original volume.
Figure 3C:
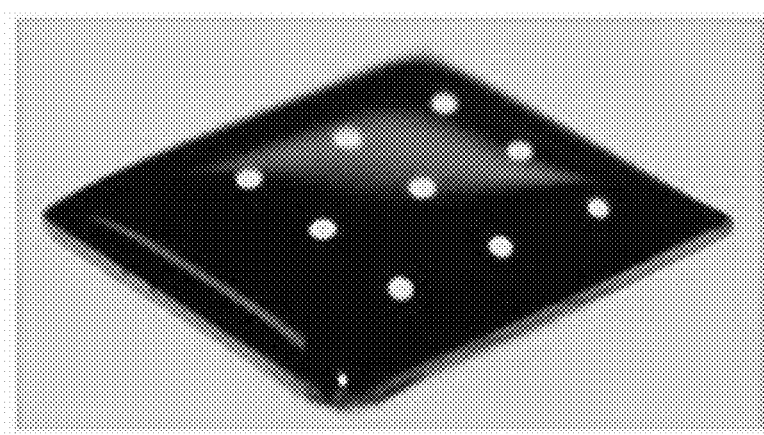
FIG. 3C shows a photographic image of the droplet array in an oil encapsulation when the droplets are nearly completely evaporated.

FIGS. 3A-3C show photographic images of exemplary oil encapsulated hybridization chambers (e.g., nano or microliter volume). FIG. 3A shows a photographic image of a droplet array dispensed on black Si template without oil encapsulation. FIG. 3B shows a photographic image of the droplet array in an oil encapsulation when the droplet volume is reduced to about 50% of the original volume. FIG. 3C shows a photographic image of the droplet array in an oil encapsulation when the droplets are nearly completely evaporated, leaving a thin layer of liquid over the hydrophilic areas. The enhanced green fluorescent intensity shows the effects of sample concentration and accelerated hybridization. FIGS. 3A and 3B are photographs under unfiltered white light, while FIG. 3C is a photograph under filtered fluorescence.

The kinetics of the hybridization process can be described by the following equations:

$$\frac{\partial C}{\partial t} = D \frac{\partial^2 C}{\partial x^2} \quad x > 0 \tag{1-a}$$

$$\frac{\partial C}{\partial t} = D \frac{\partial^2 C}{\partial x^2} - \frac{C}{\tau_c} + \frac{KQ_T}{1 + KL\tau_c}, \tag{1-b}$$

$x = 0$ (position of the DNA probe)

C: target nucleic acid concentration;
D: nucleic acid diffusivity;
$Q_T$: total amount of target nucleic acid in the droplet;
$\tau_c$: time for hybridization with the DNA probe (unit: seconds); and
K: dissociation constant of nucleic acid/DNA oligo complex (unit: 1/sec-cm); and
L: liquid thickness.

Equation (1) can be solved analytically to yield the time dependence of hybridization efficiency, defined as the fraction of target nucleic acids that are hybridized with the DNA probes:

$$\eta(t) \equiv \frac{C_s(t)}{Q_T} = \left[\frac{1}{1 + K\tau_c L}\right]\left\{1 - \exp\left[\frac{-Dt}{\left(\frac{2L}{\pi}\right)^2}\right]\right\} \tag{2}$$

Equation (2) suggests that the time to reach equilibrium is proportional to $L^2/D$, provided that there exist enough number of probes for the target nucleic acids to hybridize with, which can be obtained in the exemplary designs. For relatively short (e.g., 20 to 2K nt) DNAs or RNAs with D being in the order of $10^{-7}$ cm$^2$/s, it takes longer than 100 hours for the reaction to reach equilibrium in a typical reactor (e.g., 96-well plate) with a liquid height of a few millimeters. By reducing the liquid thickness to ~20 μm, the time to reach equilibrium state can be reduced by more than 3,000 times to be as short as 5 minutes.

Secondly, the prefactor $$\frac{1}{1 + K\tau_c L}$$

in Equation (2) suggests that high hybridization efficiency can be achieved at equilibrium only if $L<1/(K\tau_c)$ (i.e., the liquid thickness is thinner than the characteristic length determined by the countering processes of hybridization and dissociation). The above condition cannot be met with a large (e.g., L=5 mm) liquid thickness in conventional wellplates designs unless the temperature is substantially below the melting (denaturing) temperature, thus slowing the hybridization process further because the diffusivity in Equation (2) is also reduced with the decreasing temperature. By reducing the liquid thickness, the necessary condition for high miRNA hybridization efficiency: $L<1/(K\tau_c)$ can be met, thus producing high and repeatable nucleic acid hybridization efficiency within a short time (e.g., <10 minutes). The allowance of using higher hybridization temperature also improves the stringency of hybridization, which can be especially important for miRNA detection because many miRNAs may be different by 1 or 2 nucleotides for a typical length of around 20 nucleotides.

Exemplary On-Chip miRNA Detection Using the Stacking Effect

As mentioned previously, one way to detect and quantify the target nucleic acids that are hybridized with the DNA oligo probes is to use the stacking effect. For example, after nucleic acid hybridization in the oil-encapsulated reaction chambers (e.g., nano or microliter volume), a relatively high concentration (e.g., 10 nM) of quantum-dot linked reporter DNA oligos is introduced to allow these reporter DNA oligos to hybridize with the DNA probes. In some embodiments, different DNA probes that are designed to match different target miRNAs have the same sequence for the first 8 nucleotides so that substantially all the probes can hybridize with the Q-dot linked reporting DNA oligos, as was shown in FIG. 1E. After washing off extra Q-dot linked reporter DNA oligos, there exist DNA probes in two possible states: probes hybridized with reporter DNA oligos but without the target nucleic acid and probes hybridized with both the target nucleic acid and the reporter DNA oligos. Because of the stacking effect, the binding strength of the DNA oligos is enhanced by the hybridized nucleic acids that are immediately next to the DNA oligos with a nick. By introducing a relatively strong flow that exerts shear stress to the Q-dot linked reporter DNA oligos, one can selectively remove the Q-dot linked reporter oligos from the unhybridized DNA probes (in terms of the target nucleic acid) and subsequently measure the number of target nucleic acids within each island based on the fluorescence intensity of the remaining Q-dots.

Figure 4A:
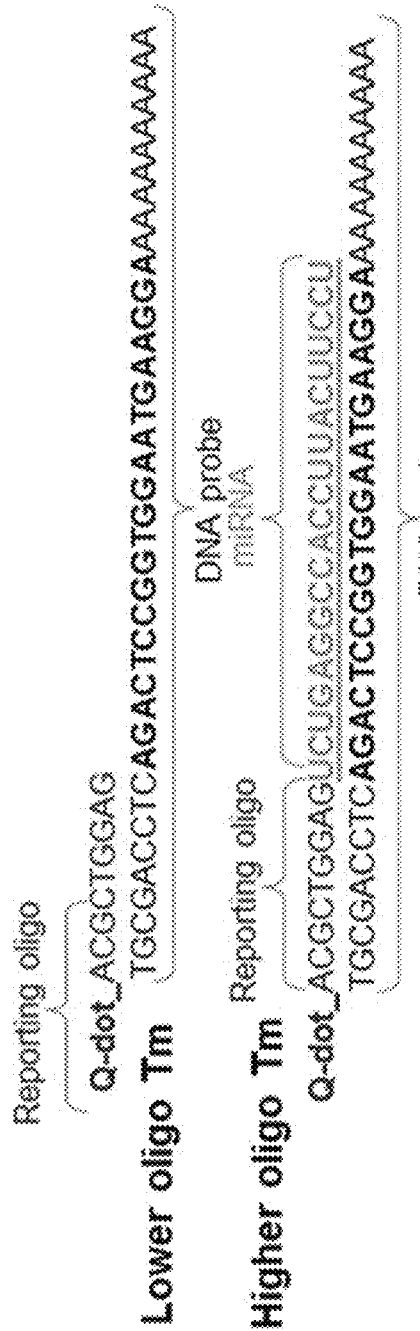
FIG. 4A shows an exemplary design of a DNA probe and Q-dot linked reporter oligo.
Figure 4B:
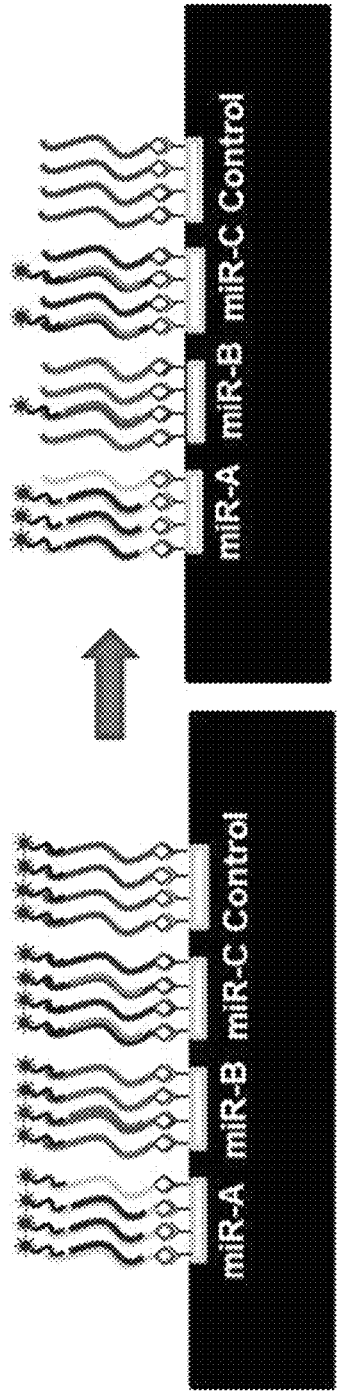
FIG. 4B shows an exemplary device schematic for detection and quantification of different miRNAs and the process of using the stacking effect to selectively remove the Q-dot linked reporter oligos from DNA probes without hybridized nucleic acid.
Figure 4C:
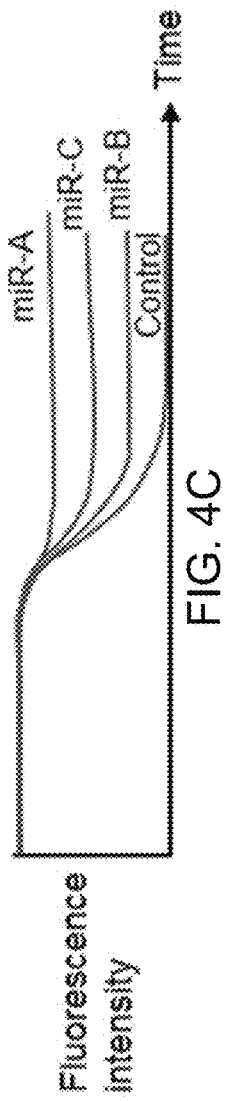
FIG. 4C shows an exemplary plot of anticipated time-dependent fluorescent signals from each specific miRNA marker shown in FIG. 4B and the signal from negative control.

FIGS. 4A-4C show schematics of exemplary nucleic acid detection and quantification techniques using Q-dot linked reporting oligo and the stacking effect. FIG. 4A shows an exemplary design of a DNA probe and Q-dot linked reporter oligo. As mentioned above, the stacking effect can produce a melting temperature difference for the reporting oligo between the nucleic acid (e.g., miRNA) hybridized and unhybridized probes. FIG. 4B shows an exemplary device schematic for detection and quantification of different miRNAs and the process of using the stacking effect to selectively remove the Q-dot linked reporter oligos from DNA probes without hybridized nucleic acid. FIG. 4C shows an exemplary plot of anticipated time-dependent fluorescent signals from each specific miRNA marker shown in FIG. 4B and the signal from negative control. As shown by the plot, a high number of hybridized target nucleic acids in a given sample island results in a higher detected fluorescent intensity from that sample island.

Figure 5A:
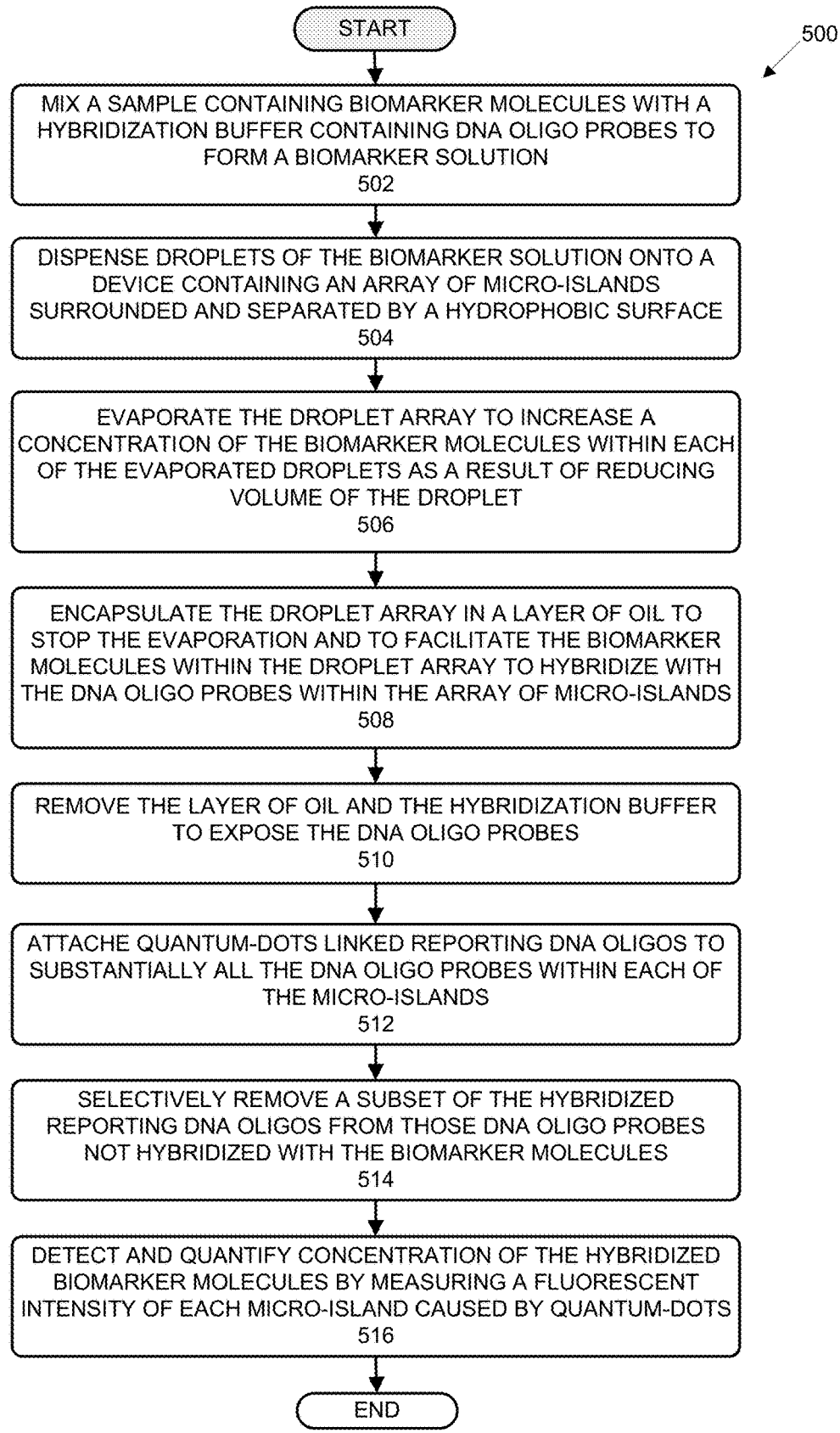
FIG. 5A presents a flowchart illustrating an exemplary process for enriching biomarker molecules, such as DNAs and RNAs within a biosensor to facilitate ultra-sensitive detection and quantification of the biomarker molecules without an amplification of the biomarker molecules.

FIG. 5A presents a flowchart illustrating an exemplary process 500 for enriching biomarker molecules, such as DNAs and RNAs within a biosensor to facilitate ultrasensitive detection and quantification of the biomarker molecules without an amplification of the biomarker molecules. The process may include mixing a sample containing biomarker molecules, including DNAs, RNAs, miRNAs, and other nucleic acids with a hybridization buffer containing DNA oligo probes, thereby forming a biomarker solution (502). The process also includes dispensing droplets of the biomarker solution onto a device containing an array of micro-islands or microarray of islands surrounded and separated by a hydrophobic surface (504). The surface of each micro-island is functionalized with a set of DNA oligo probes, and each droplet is dispensed onto a separate micro-island to form a droplet array of the biomarker solution which substantially coincides with the array of micro-islands or microarray of islands The process then evaporates the droplet array to increase a concentration of the biomarker molecules within each of the evaporated droplets as a result of reducing volume of the droplet (506).

After the droplet array has evaporated to a thin layer of the biomarker solution, the process then encapsulates the droplet array in a layer of oil to stop the evaporation and to facilitate the biomarker molecules within the droplet array to hybridize with the DNA oligo probes within the microarray of islands or array of micro-islands (508). After the completion of the hybridization, the process then removes the layer of oil and the hybridization buffer to expose the DNA oligo probes (510). Next, the process attaches quantum-dots linked reporting DNA oligos to the set of DNA oligo probes within each of the microarray of islands or array of micro-islands (512). The process then selectively removes a subset of the hybridized reporting DNA oligos from a corresponding subset of the DNA oligo probes which are not hybridized with the biomarker molecules (514). Hence, after the removal of the subset of the reporting DNA oligos, the number of the quantum-dots linked reporting oligos within each of the microarray of islands or array of micro-islands is substantially equal to the number of the hybridized biomarker molecules within the same micro-island. The process can also include detecting and quantifying concentration of the hybridized biomarker molecules by either measuring a fluorescent intensity of each micro-island caused by the remaining quantum-dots or by counting the number of the remaining quantum dots using an image processing software (516).

Figure 5B:
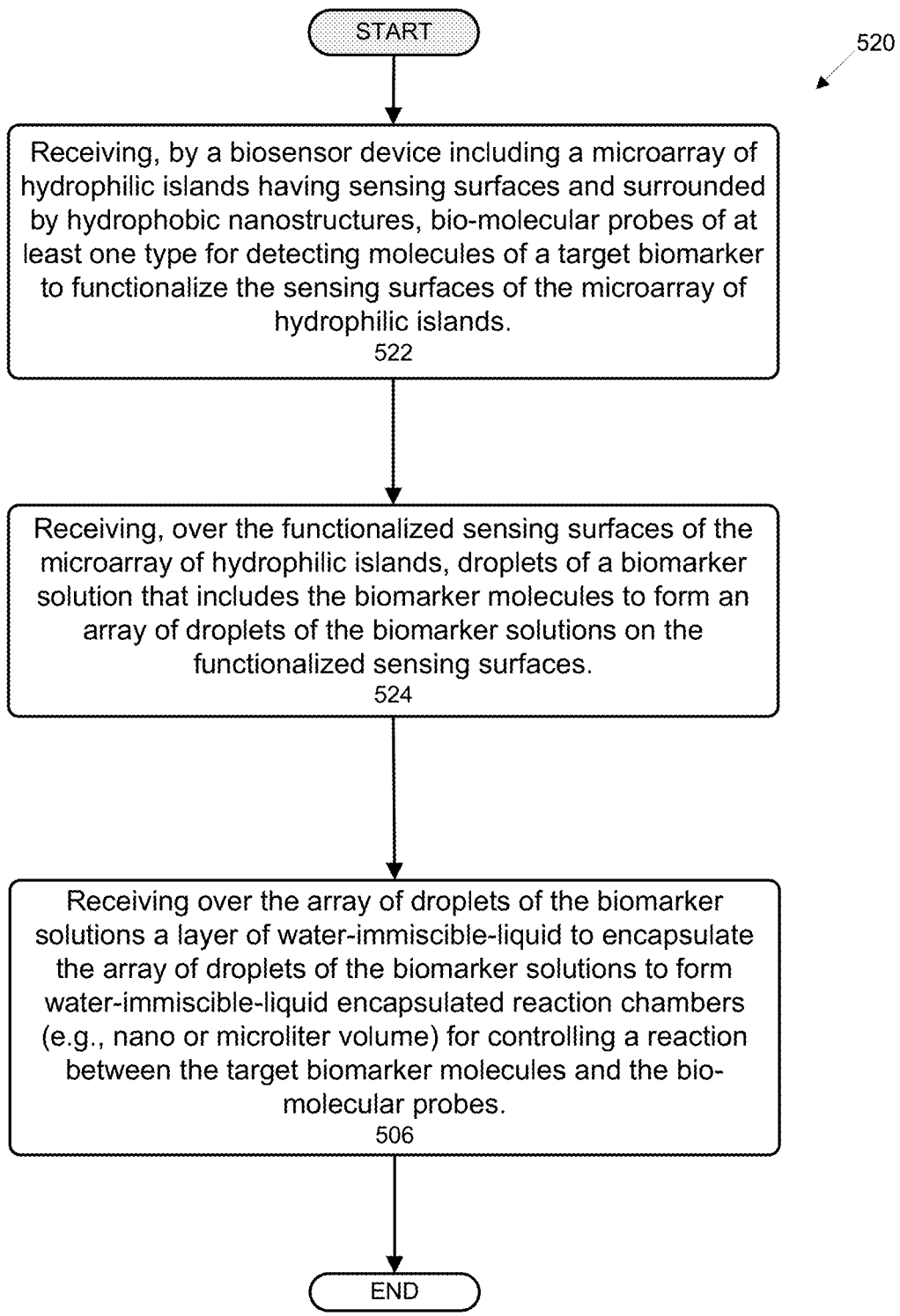
FIG. 5B presents a flowchart illustrating an exemplary process performed by a biosensor for enriching biomarker molecules, such as DNAs and RNAs to facilitate ultra-sensitive detection and quantification of the biomarker molecules without an amplification of the biomarker molecules.

FIG. 5B presents a flowchart illustrating an exemplary process 520 performed by a biosensor device for enriching biomarker molecules, such as DNAs and RNAs to facilitate ultra-sensitive detection and quantification of the biomarker molecules without an amplification of the biomarker molecules. A biosensor device as described in this patent document can perform the process 520 to enrich and detect biomarker molecules includes receiving, by a biosensor device including a microarray of hydrophilic islands having sensing surfaces and surrounded by hydrophobic nanostructures, bio-molecular probes of at least one type for detecting molecules of a target biomarker to functionalize the sensing surfaces of the microarray of hydrophilic islands (522). The method includes receiving, over the functionalized sensing surfaces of the microarray of hydrophilic islands, droplets of a biomarker solution that includes the biomarker molecules to form an array of droplets of the biomarker solutions on the functionalized sensing surfaces (524). The method includes receiving over the array of droplets of the biomarker solutions a layer of water-immiscible-liquid to encapsulate the array of droplets of the biomarker solutions to form water-immiscible-liquid encapsulated reaction chambers (e.g., nano or microliter volume) for controlling a reaction between the target biomarker molecules and the bio-molecular probes (526). In one embodiment, the water-immiscible-liquid includes oil. In one embodiment, each droplet is nanoliter or less.

The method can be implemented in various ways to include one or more of the following features. The biomolecular probes of at least one type can include DNA probes, and the molecules of biomarkers can include nucleic acids. The DNA probes can include DNA oligonucleotides. Receiving the layer of water-immiscible-liquid to encapsulate the array of droplets of the biomarker solutions to form water-immiscible-liquid encapsulated reaction chambers (e.g., nano or microliter volume) for controlling a reaction between the target biomarker molecules and the bio-molecular probes can include facilitating hybridization of the biomarker molecules with the DNA probes within the reaction chambers (e.g., nano or microliter volume). The method can include receiving labeling materials to within the reaction chambers (e.g., nano or microliter volume) to label bio-molecular probe attached biomarker molecules formed responsive to the controlled reaction. The labeling materials can include quantum-dots. The nucleic acids can include DNA, RNA or miRNA-based nucleic acids. The sensing areas can include a layer of silicon oxide (SiO2). The super-hydrophobic surface can include black silicon. The target biomarker molecules can include fluorescently labeled biomarker molecules to determine a concentration of the target biomarker molecules based on a fluorescent intensity of the fluorescently labeled biomarker molecules that react with bio-molecular probes. In one embodiment, the water-immiscible-liquid includes oil. In one embodiment, each droplet is nanoliter or less.

Exemplary Embodiments of a Sample Enrichment Template

In some embodiments, the disclosed techniques, devices, and systems of nucleic acid sample enrichment by evaporating droplets can overcome the so-called "coffee ring effect." On a typical surface, the suspended particles and macro molecules may precipitate on the surface when the liquid droplet is reduced to a certain size, leaving marks or stains on the surface, referred to as "coffee ring effect." Without eliminating the coffee ring effect, the target nucleic acids may not be condensed on the microarray of islands or array of micro-islands where the molecular probes are immobilized. This coffee ring effect may be caused by a weak Marangoni flow inside the droplet when the liquid/air boundary of the droplet moves towards the substrate. To strengthen the Marangoni flow which drives the nucleic acids toward the center of the droplet instead of forming the "coffee ring", various embodiments can reduce the surface tension by adding surfactant, using AC electrowetting to unpin the contact line as the droplet evaporates, or creating super-hydrophobic surface. In the discussion below, exemplary embodiments of a black silicon template and a nanostructured polymer template are described to create the super-hydrophobic surface. A super-hydrophobic surface can produce a large contact angle of well over 90 degrees for droplets of aqueous solution. In the case of black silicon and nanostructured polydimethylsiloxane (PDMS) surfaces, the contact angle of water droplets can be greater than 150 degrees.

In one embodiment to achieve super-hydrophobic surface, the device template can include an array of hydrophilic micro-islands or microarray of hydrophilic islands surrounded by super-hydrophobic black silicon fabricated on a Si wafer. To form black silicon, an exemplary Bosch etching process is employed in a reactive ion etcher. The etch process includes alternating cycles of etching ($SF_6$) and passivation ($C_4F_8$) to form nanopillar structures. For areas that are protected by lithographically defined $SiO_2$ patterns, no etching or passivation occurs so the hydrophilic properties are preserved after the black silicon process. The 2D array of hydrophilic micro-island is then coated with specific DNA probes matching specific nucleic acid targets.

In another embodiment to achieve super-hydrophobic surface, the device template can include an array of hydrophilic micro-islands or microarray of hydrophilic islands surrounded by super-hydrophobic PDMS pillars formed using nanoimprinting or hot embossing process. To obtain such a device template, an electron beam lithographically patterned nanopillars are first formed on a silicon wafer as the mold. For example, the diameter of the pillar can be in a range of 50 nm to 250 nm and the center-to-center distance of these pillars is about twice of the pillar diameter. The pillars may be arranged in a square or hexagonal lattice or in a semi-random fashion. Next, a "daughter mold" is formed from the silicon master mold. Due to the nature of the imprinting process, the daughter mold has an array of holes, complementary to the pillars. The daughter mold may be made of Perfluoropolyether (PFPE) Fluorolink MD700 (e.g., Solvay Solexis) as a stamp. The complementary patterns on the stamp can be formed on the PDMS material using standard nano-imprinting or hot embossing process. PDMS surface by itself is hydrophobic. When such nanopatterns are formed, the hydrophobicity increases to give an ultra large contact angle comparable to the hydrophobicity of black silicon. To form the hydrophilic microislands, a shadow mask can be used for $SiO_2$ deposition by sputtering or E-beam evaporation. The areas covered by the $SiO_2$ layer become hydrophilic.

Note that the above process to form the device template with nanostructured PDMS surface can also be applied to other polymer such as Cyclic Olefin Copolymer (COC) and Cyclic Olefin Polymer (COP) that may be more suitable for volume production and may have lower tendency of molecular adsorption than PDMS. Both COC and COP have low autofluorescence so will generally not affect the luminescence detection.

Figure 6:
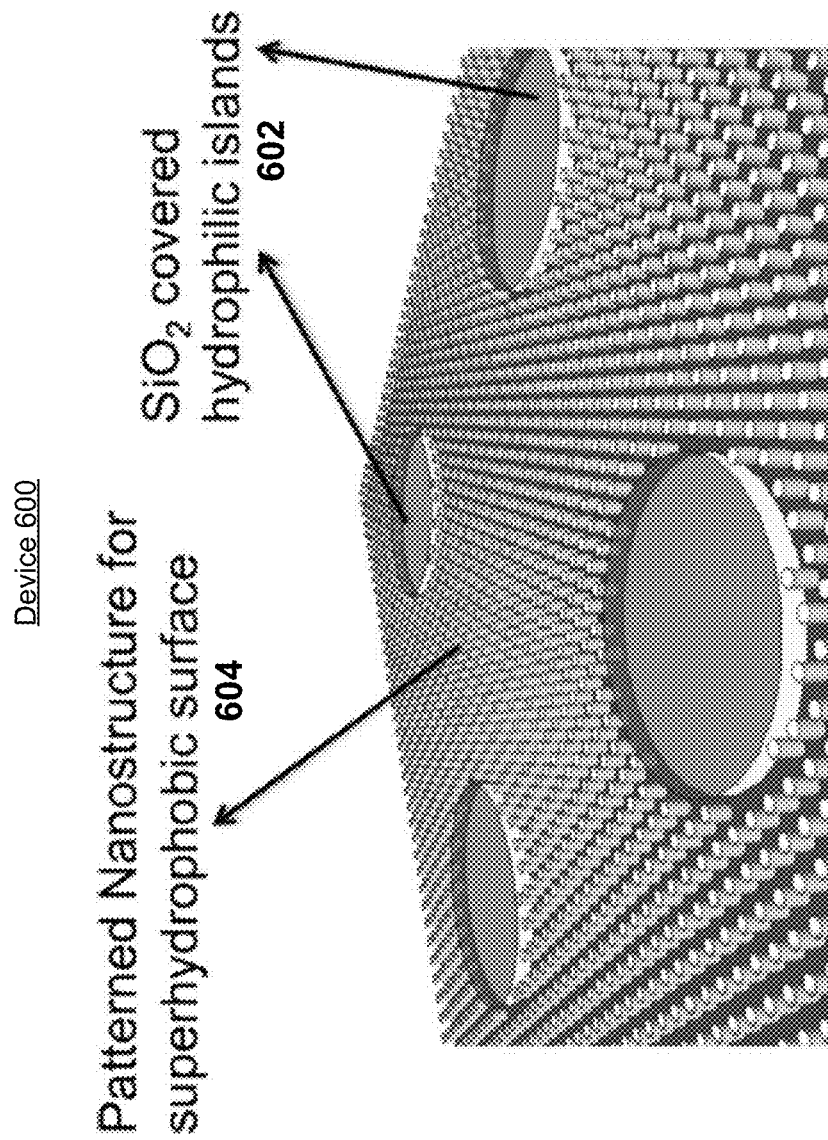
FIG. 6 shows an exemplary device for forming a droplet array.

Example of Constructing an Oil-Encapsulated Nano-Droplet (e.g., Nanoliter Volume or Less) Array for Bio-Molecular Detection
Template Design FIG. 6 illustrates an exemplary device 600 (i.e., the template) for forming a droplet array. As can be seen in FIG. 6, the surface of device/template 600 includes hydrophilic islands 602 surrounded by a hydrophobic or superhydrophobic surface 604 that has a patterned nanostructure. On each hydrophilic island 602, one type of molecular probes for a specific molecular target may be immobilized. Each hydrophilic island 602 is covered with a thin layer of $SiO_2$ to attract the sample droplet and to anchor the molecular probes because the $SiO_2$ surface is compatible with most of the surface modification protocols for biosensors. In some designs, the $SiO_2$ covered hydrophilic islands have a 400 μm diameter and are separated by 4 mm. Outside the $SiO_2$ covered areas, patterned nanostructures are formed to turn silicon into black silicon having hydrophobic or superhydrophobic properties. The black silicon fabrication process is adopted in the illustrated design due to its high throughput and low cost. When forming a droplet on a given hydrophilic island 602, the hydrophobic or superhydrophobic surface 604 surrounding the hydrophilic island 602 allows the droplet to shrink with a minimal solid/liquid contact area and sample loss. In some designs, an array of hydrophilic 20 islands is formed on a substrate and, if needed, the design can be easily scaled according to the applications.

Device Architecture and Process Flow

Figure 7:
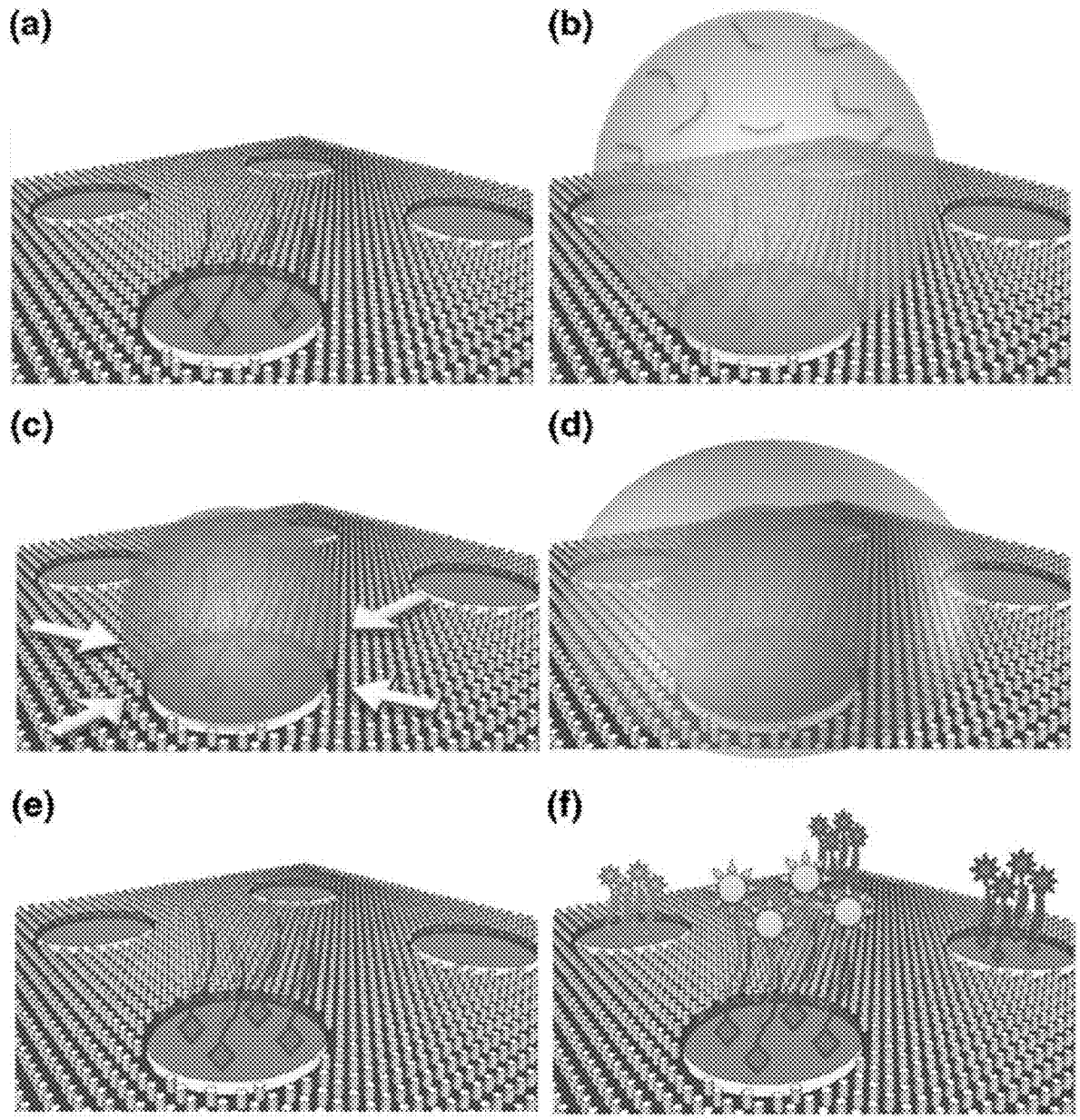
FIG. 7 shows schematics illustrating an exemplary workflow of a biosensor based on the device in FIG. 6 for bio-molecules, such as nucleic acid detection.

FIG. 7 shows schematics illustrating an exemplary workflow 700 of a biosensor based on device 600 in FIG. 6 for bio-molecules such as nucleic acid (e.g., DNAs and RNAs) detection. Workflow 700 includes six steps 7(a)-7(f). As can be seen in FIG. 7, in step 7(a), the probes having the complementary sequence to the target bio-molecules, such as nucleic acids, are anchored on the $SiO_2$ sensing area/islands. In specific implementation of step 7(a), amine end-linked probes are immobilized to aldehyde-activated $SiO_2$ islands. In step 7(b), sample droplets of the target bio-molecules mixed in diluted hybridization buffer are pipetted onto the hydrophilic islands. In specific implementations of step 7(b), the target bio-molecules include streptavidin labeled miRNA mimic oligonucleotides and the sample droplets of 4 μL each are dispensed on the template surface through a rough (visual) alignment with the $SiO_2$ islands. In step 7(c), the concentration of the target bio-molecules, e.g., the miRNA mimic oligonucleotides is increased and the volume of the sample droplet is reduced by evaporation. In specific implementation of step 7(c), through evaporation, the volume of each droplet is shrunk to 4 nL.

In step 7(d), a layer of oil is dispensed to encapsulate the shrunk droplets to keep the droplet volume and the salt concentration stable. As can be seen in step 7(d), an oil drop can encapsulate a given shrunk droplet, thereby forming a microchamber (e.g., a reaction chamber of microliter volume) or a nanochamber (e.g., a reaction chamber of nanoliter volume). The layer of oil stops the evaporation process and the hybridization reaction takes place in controlled reaction conditions within the encapsulated micro/nanochambers (which also referred to as a "micro/nano-droplet reactor"). In step 7(e), the oil layer and hybridization buffer are washed away, exposing the sample probes, some of which are hybridized with the target nucleic acids. In step 7(f), the sample probes (e.g., DNA duplex) are labeled with quantum dots (Q-dots) for fluorescent detection. Finally, the immobilized target bio-molecules, such as streptavidin labeled miRNA mimic oligonucleotides are visualized and quantified after in-situ labelling with quantum dots, such as streptavidin conjugated quantum dots.

In some implementations, after step 7(d), the assay is incubated at 50° C. for 30 minutes or up to 6 hours before washing in step 7(e). The length of incubation time does not show obvious effect on detection sensitivity, indicating the diffusion process may not be the sensitivity limiting factor within the nano-droplet (e.g., nanoliter volume or less) reactors. In some implementations, the workflow 700 of the biosensor is used for protein detection. In such implementations, the nucleic acid hybridization process is replaced with the protein-ligand binding process.

Device Fabrication

As mentioned above, the device for bio-molecules detection can be made of an array of hydrophilic $SiO_2$ islands surrounded by a hydrophobic or superhydrophobic surface. The device may start on a Si substrate. The array of hydrophilic islands can be fabricated on the Si surface using the conventional photolithographic technique and nanopillars can be formed by deep reactive ion etch (DRIE) over the rest of the Si area to create the black silicon hydrophobic or superhydrophobic surface.

Figure 8:
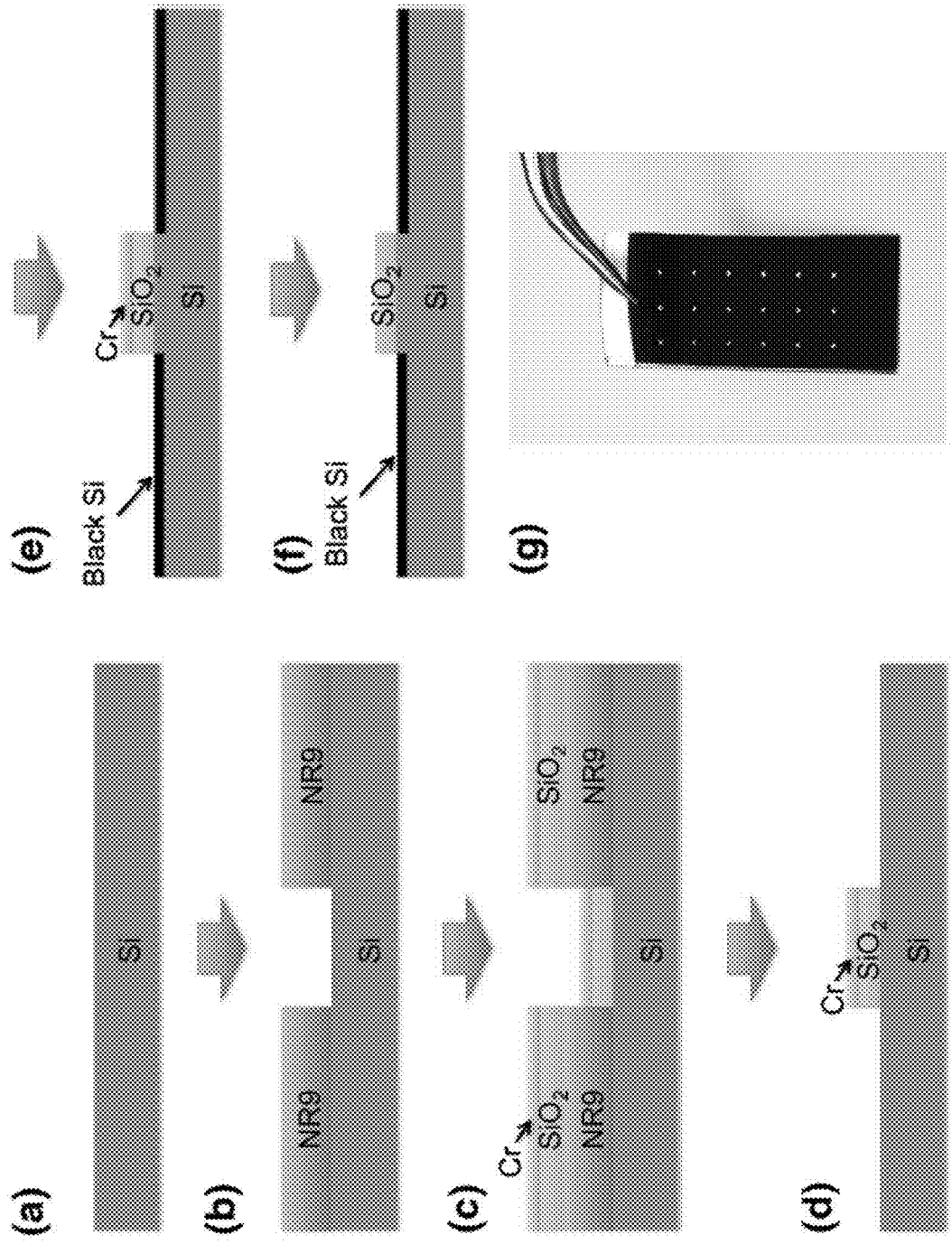
FIG. 8 illustrates an exemplary fabrication process of a device for bio-molecules detection including a microarray of islands or micro-island array for evaporating droplets.

FIG. 8 illustrates an exemplary fabrication process 800 of a device for bio-molecules detection including a micro-island array for evaporating droplets. Fabrication process 800 includes steps 8(*a*)-8(*f*). As can be seen in FIG. 8, in step 8(*a*), a silicon wafer, such as a mechanical grade silicon wafer is cleaned for microfabrication. In step 8(*b*), a photoresist layer (e.g., negative tone photoresist NR9-1500PY (Futurrex, USA)) is patterned on the silicon wafer by lithography. The patterned photoresist layer defines areas of hydrophilic islands as well as surrounding areas of hydrophobic or superhydrophobic surface. After photoresist patterning, $SiO_2$ and chromium (Cr) layers are deposited on the Si substrate by sputtering in step 8(*c*). In a specific implementation, Cr and $SiO_2$ films are deposited on the Si wafer using a sputtering system (e.g., Denton Discovery 18, Denton Vacuum, LLC) and the thickness of the Cr and $SiO_2$ films are 100 nm and 120 nm, respectively. In step 8(*d*), a micro-island array of $SiO_2$/Cr dots is patterned on the silicon wafer. The remaining photoresist is removed, e.g., by using acetone under slight agitation.

After forming the micro-island array, a hydrophobic or superhydrophobic surface of black Si is formed in step 8(*e*). In some implementations of step 8(*e*), the hydrophobic or superhydrophobic surface is formed by forming nanopillars using a deep reactive ion etching (DRIE) process (e.g., using Plasmalab System 100, Oxford Instruments). Unlike most top-down processes for nanostructure formation that require definition of nanoscaled patterns and pattern transfer, the nanopillars are formed naturally during the deep reactive etching process. In an example process, during the DRIE process, $SF_6$ gas was flowed at 30 sccm during the 8 seconds of reaction time, followed by a passivation cycle when $C_4F_8$ gas was flowed at 50 sccm for 7 seconds. After 80 etching/passivation cycles, dense arrays of nanopillars were formed with an average pillar height of 4.5 μm. Also during the DRIE process, those islands covered by the Cr layer were protected. In the last step 8(*f*), the Cr layer over the microarray of islands or array of micro-islands is removed by a Cr etchant to obtain the $SiO_2$ covered hydrophilic islands. The photograph in FIG. 8(*g*) shows a fabricated device containing a 3×6 array of hydrophilic islands. The optical reflectivity difference between the array of $SiO_2$ islands and the surrounding black Si can be clearly observed.

Nucleic Acids Detection

Figure 9:
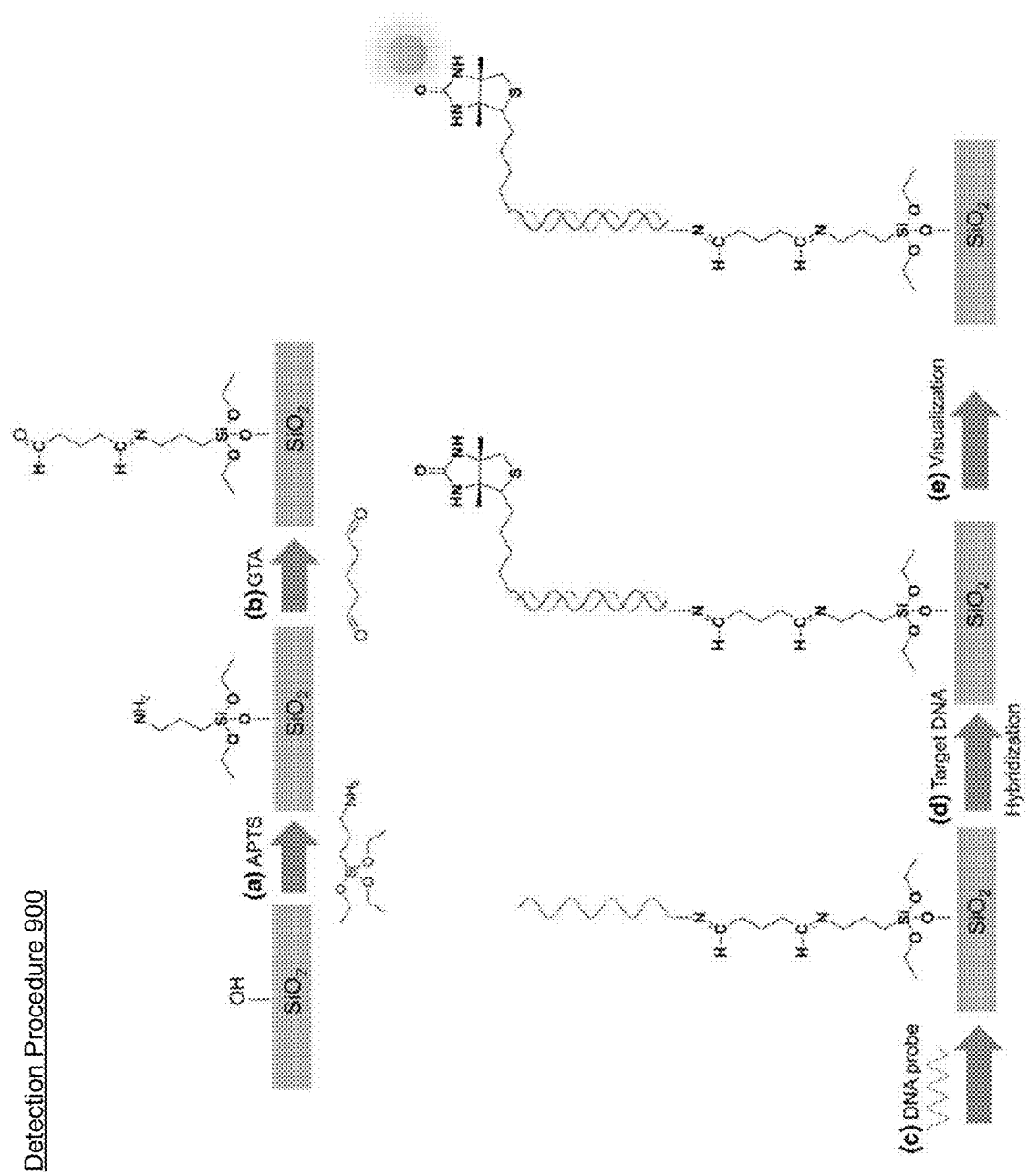
FIG. 9 shows schematics of an exemplary nucleic acids detection procedure on the hydrophilic surface of the bio-molecules detection device from FIG. 8.

The detection of bio-molecules, such as nucleic acids may be performed with the above device obtained through the process described in FIG. 8. FIG. 9 shows schematics of an exemplary nucleic acids detection procedure 900 on the hydrophilic surface of the bio-molecules detection device from FIG. 8. Detection procedure 900 includes steps 9(*a*)-9(*e*), which includes functionalizing the $SiO_2$ surface, immobilizing the DNA probe, and detecting the target nucleic acids.

As can be seen in FIG. 9, in step 9(*a*), the device surface is linked to aminopropyl-triethoxysilane (APTS or APTES) which converts silanol group (SiOH) on the device surface to amine group ($NH_2$). The silicon atom in the APTES molecule also forms a chemical bond with the oxygen of the hydroxyl group (OH). Next, in step 9(*b*), APTES is bonded with glutaraldehyde (GTA), which is used as a grafting agent for DNA immobilization. GTA binding can be achieved through its aldehyde group (COH) forming a chemical bond with the amino group of APTES, as shown in FIG. 9(*b*). Step (c) shows DNA probe immobilization, wherein a given DNA oligonucleotide probe with amine group at the 3' end is linked to a given aldehyde group of the GTA. Next in step 9(*d*), target nucleic acids, such as a DNA with biotin modification at the 3' end is hybridized with the anchored DNA probe of a complementary sequence, forming DNA duplex. In step 9(*e*), streptavidin conjugated quantum dots are bonded to DNA duplex for visualization and quantification of the amounts of hybridized DNA/RNA or DNA/DNA duplex.

Exemplary Results

Surface Roughness of Black Silicon

Figure 10:
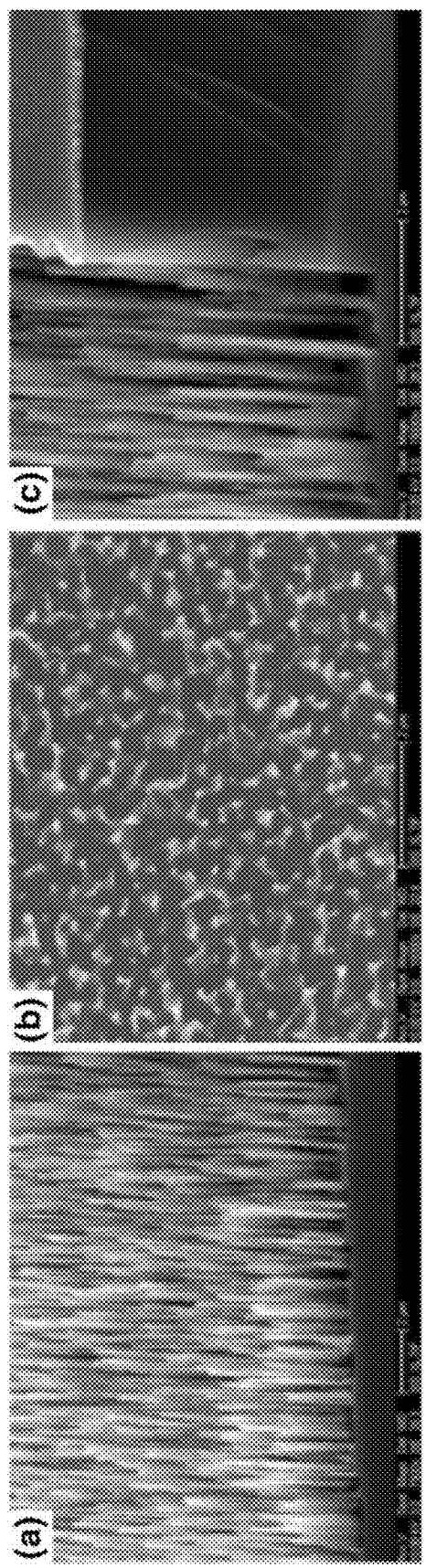
FIG. 10 shows SEM images of nanopillars fabricated using the DRIE process with 10(a) showing a 45° degree view; 10(b) showing a top view; and 10(c) showing an interface between an hydrophilic island and the nanopillars.

The evaporation process of droplets can be significantly influenced by the surface roughness, hydrophobicity and contact angle hysteresis. We examined the surface profile of the $SiO_2$ patterned black silicon template using an environmental scanning electron microscope (e.g., ESEM, FEI, XL30). FIG. 10 shows SEM images of nanopillars fabricated using the DRIE process with 10(*a*) showing an 45° degree view; 10(*b*) showing a top view; and 10(*c*) showing an interface between an hydrophilic island and the nanopillars. The nanopillars are ~300 nm in diameter, ~300 nm in spacing and 4.5 μm in height. All the scale bars in 10(*a*)-10(*c*) are 2 micrometers.

In the illustrated example, the hydrophobic or superhydrophobic property of the black Si is produced by the fluoride coating resulted from the DRIE process and the increased surface roughness. In FIG. 10(*c*), the $SiO_2$ islands are around 1.5 μm higher than the black silicon surface. Minimizing the height difference between the $SiO_2$ islands and the black silicon surroundings facilitates reducing the adhesion of target molecules to the sidewall of the islands while the sample droplet solution shrinks by evaporation.

Contact Angle Measurement

Contact angles of a 4 μL water droplet were measured at 25° C. by the sessile-drop technique with a contact-angle goniometer. The values reported herein were the averages three measurements. The same instrument was used to observe evolution of water droplets during evaporation. The contact angle of an evaporating droplet was measured continuously until the droplet was dried. Several droplets were observed during evaporation to assure consistency of the data.

Figure 11:
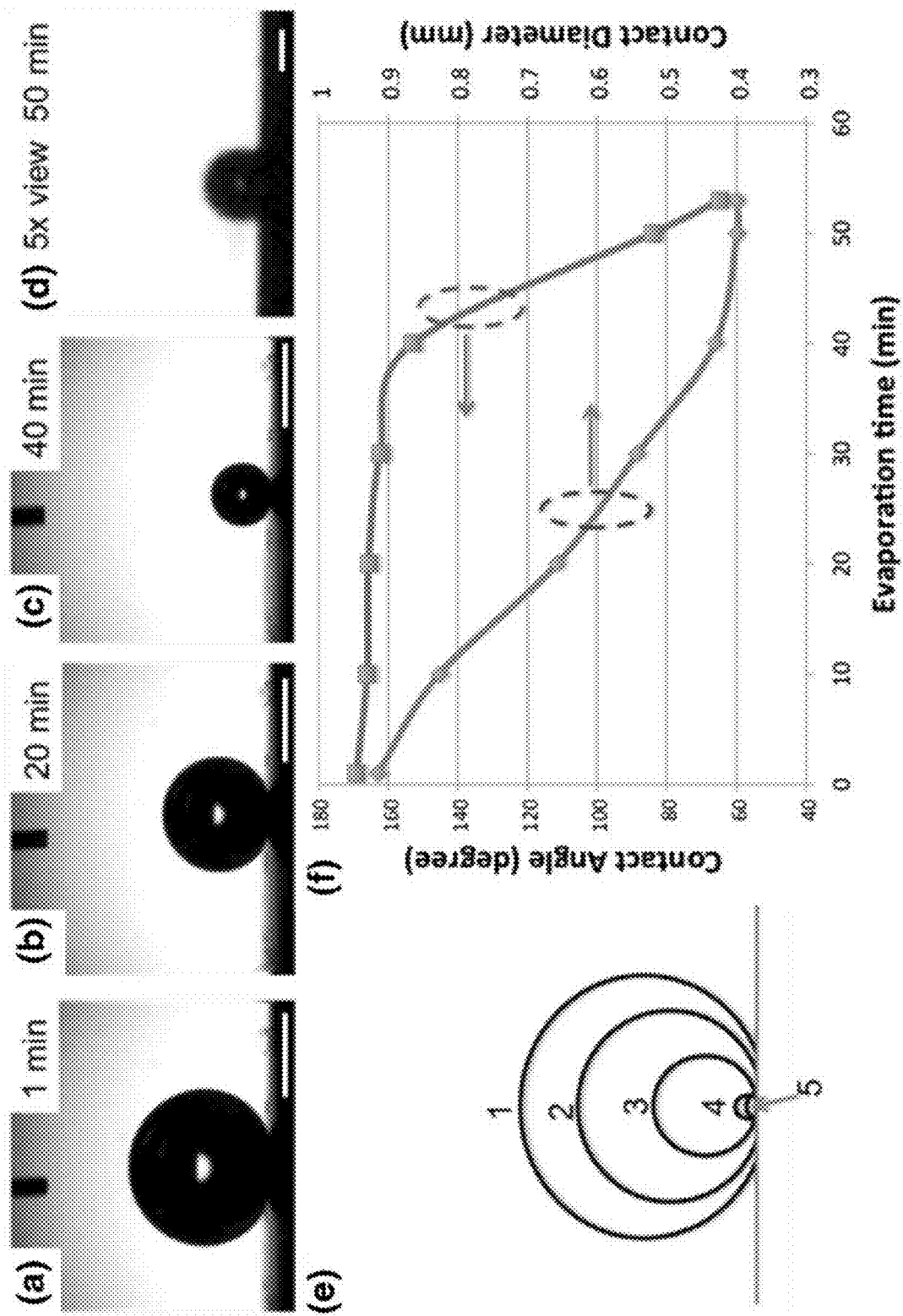
FIG. 11 shows the evolution of an evaporating water droplet on a $SiO_2$ patterned black silicon template (11(a)-11(c) photographic images of the droplet at evaporation time of 1 min, 20 mins, and 40 mins; 11(d) micrograph of the droplet at evaporation time of 50 mins; 11(e) a schematic of the evolving shape of the droplet at 1 min, 20 mins, 40 mins, 50 mins, and 53 mins; and 11(f) contact angle and contact diameter dependence on the evaporation time).

FIG. 11 shows the evolution of an evaporating water droplet on a $SiO_2$ patterned black silicon template. The static contact angle is measured at ~169.22°, suggesting the hydrophobic or superhydrophobic nature of the black silicon template. 11(*a*)-11(*c*) are photographic images of the droplet at evaporation time of 1 min, 20 mins, and 40 mins; 11(*d*) is micrograph of the droplet at evaporation time of 50 mins; 11(*e*) is a schematic of the evolving shape of the droplet at 1 min (1), 20 mins (2), 40 mins (3), 50 mins (4), and 53 mins (5); and 11(*f*) shows exemplary plots of the contact angle and contact diameter dependence on the evaporation time. The scale bars in 11(*a*)-(*c*) are 1 mm, and the scale bar in 11(*d*) is 200 micrometers. As can be observed from FIG. 11(*f*), before the droplet shrank toward the 400 μm diameter hydrophilic island, the contact angle curve is approximately a constant while the contact diameter curve decreases approximately linearly. As soon as the boundary of the droplet reached the SiO$_2$ island, the contact angle curve drops suddenly and the contact diameter curve of the droplet is pinned to the boundary of the SiO$_2$ island.

Self-Alignment Properties of Evaporating Droplet

Figure 12:
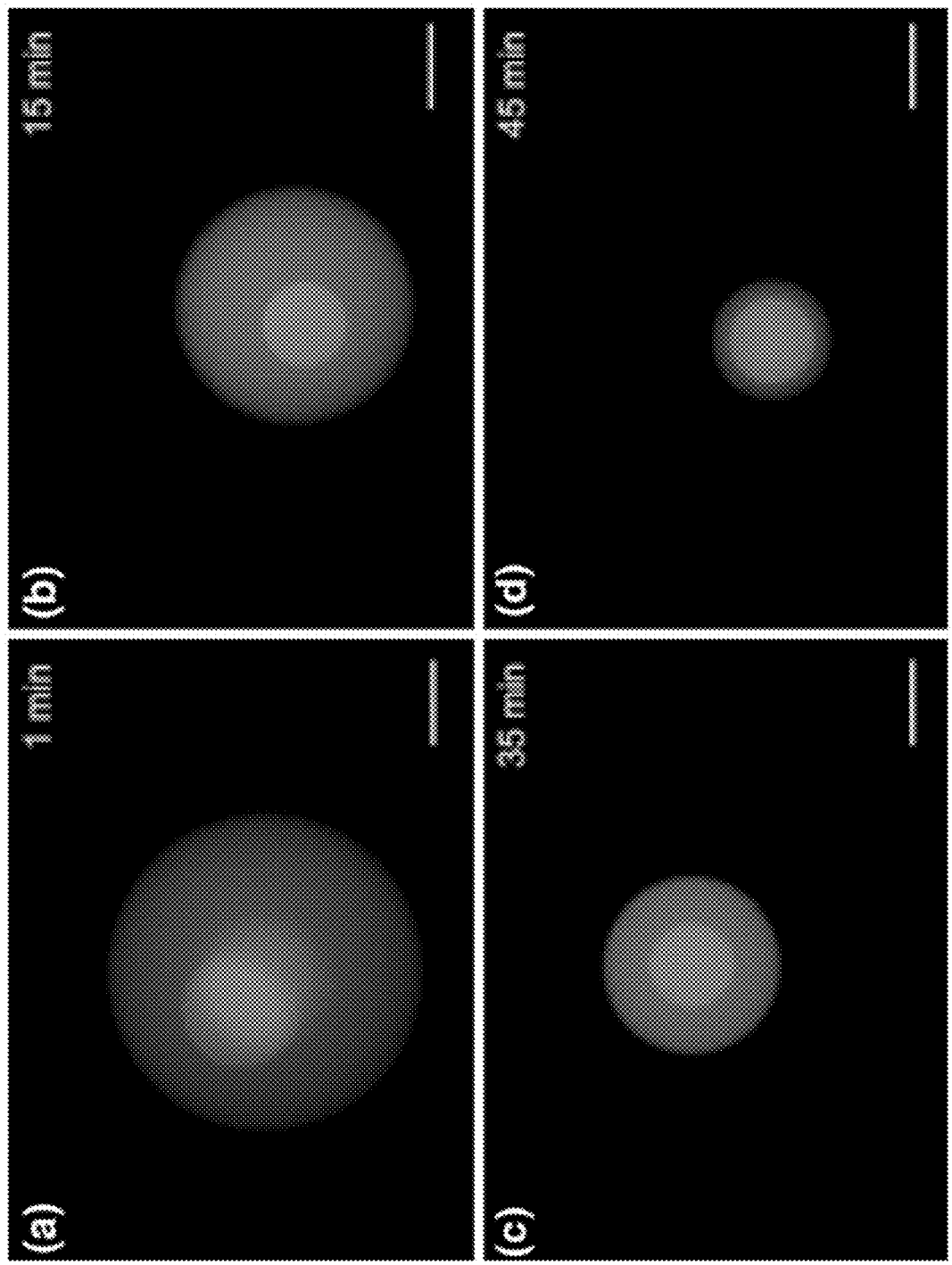
FIG. 12 shows photographic images illustrating a process when a sample droplet self-aligns with the $SiO_2$ island during evaporation: (a) 1 minute; (b) 15 minutes; (c) 35 minutes; and (d) 45 minutes.

An upright fluorescent microscope (e.g., Axio Imager, Zeiss) was used to observe the droplet evaporation over time from the top-view angle. A Xenon arc lamp was mounted on the microscope for illumination. A 4 μL droplet of water with diluted Rhodamine was pipetted onto the patterned black silicon template. Because of the SiO$_2$ hydrophilic islands, the target droplet settled onto a stable area when being dispensed. However, due to the large size mismatch between the droplet and the SiO$_2$ island, the droplet was often misaligned with the SiO2 island even though the droplet covered the SiO2 island. As the evaporation process proceeded, the droplet shrank towards the center of the SiO$_2$ island till the contour of the droplet was aligned with the boundary of the SiO$_2$ island. For example, FIG. 12 shows photographic images illustrating a process when a sample droplet self-aligns with the SiO$_2$ island during evaporation: (a) 1 minute; (b) 15 minutes; (c) 35 minutes; and (d) 45 minutes. The scale bars in all images (a)-(d) are 400 μm. Through this self-alignment process, sample droplets can be easily controlled on the black silicon template, which greatly facilitates the droplet dispensing process and molecular sensing process for point-of-care applications.

Fluorescently Labeled DNA Oligonucleotides Concentrated onto the Sensor Area

To test the capability of the evaporating droplets for sample enrichment, a 4 μL, droplet of FITC labelled DNA oligonucleotides diluted in distilled water was pipetted on the device. Solutions of progressively decreasing concentration were examined. The droplets were dried at 37° C. and investigated under an inverted epifluorescence microscope (Eclipse TE2000U, Nikon). After background subtraction, the average intensity over the entire SiO$_2$ island was analyzed using ImageJ and a custom image analysis Matlab program.

Figure 13:
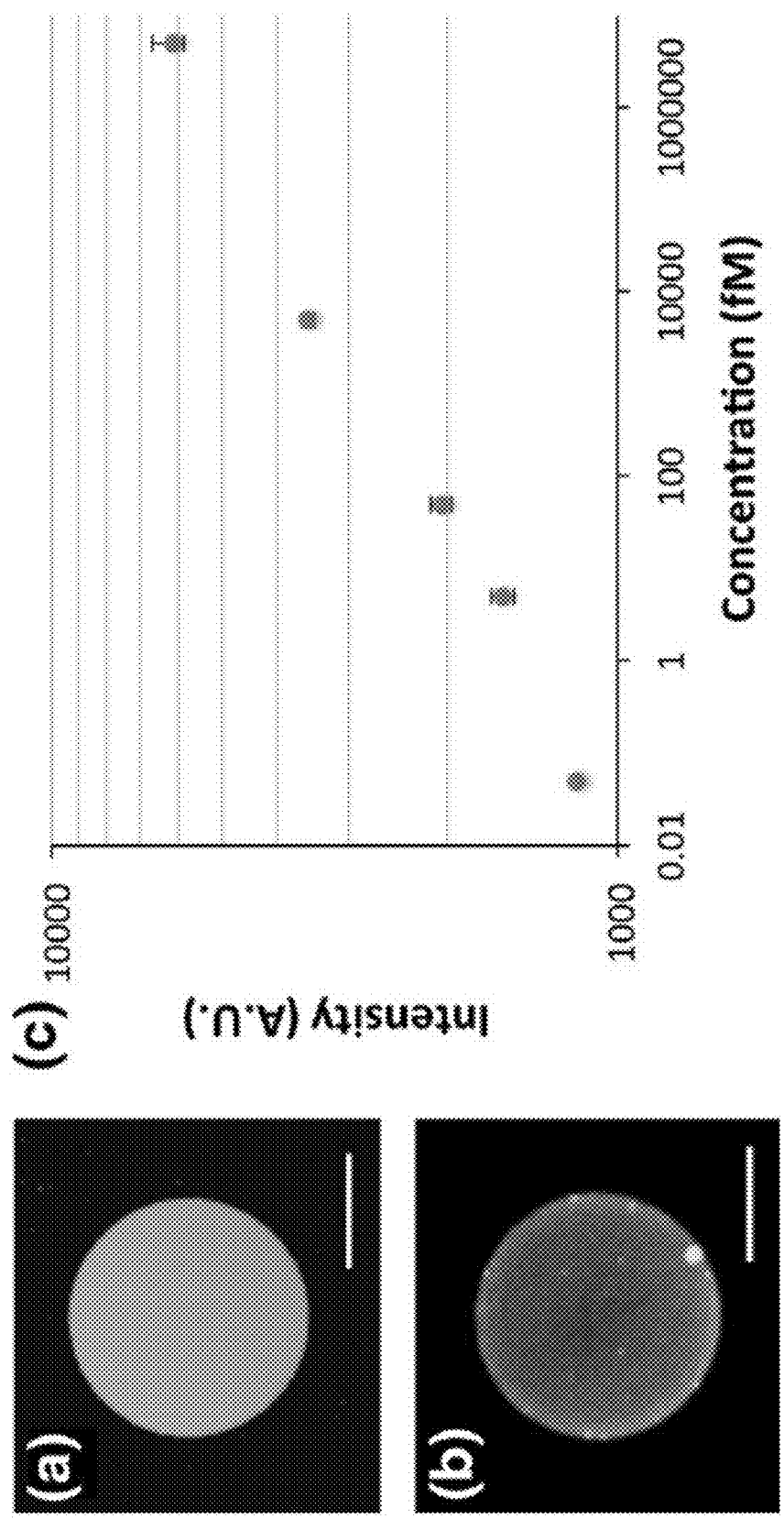
FIG. 13 shows: (a) a bright view image of a clean $SiO_2$ island surrounded by black silicon after the microfabrication process; (b) a fluorescent image of the FITC labeled DNA dried on the $SiO_2$ island; and (c) detected fluorescence intensity of FITC labeled DNA dried on the $SiO_2$ island.
Figure 14:
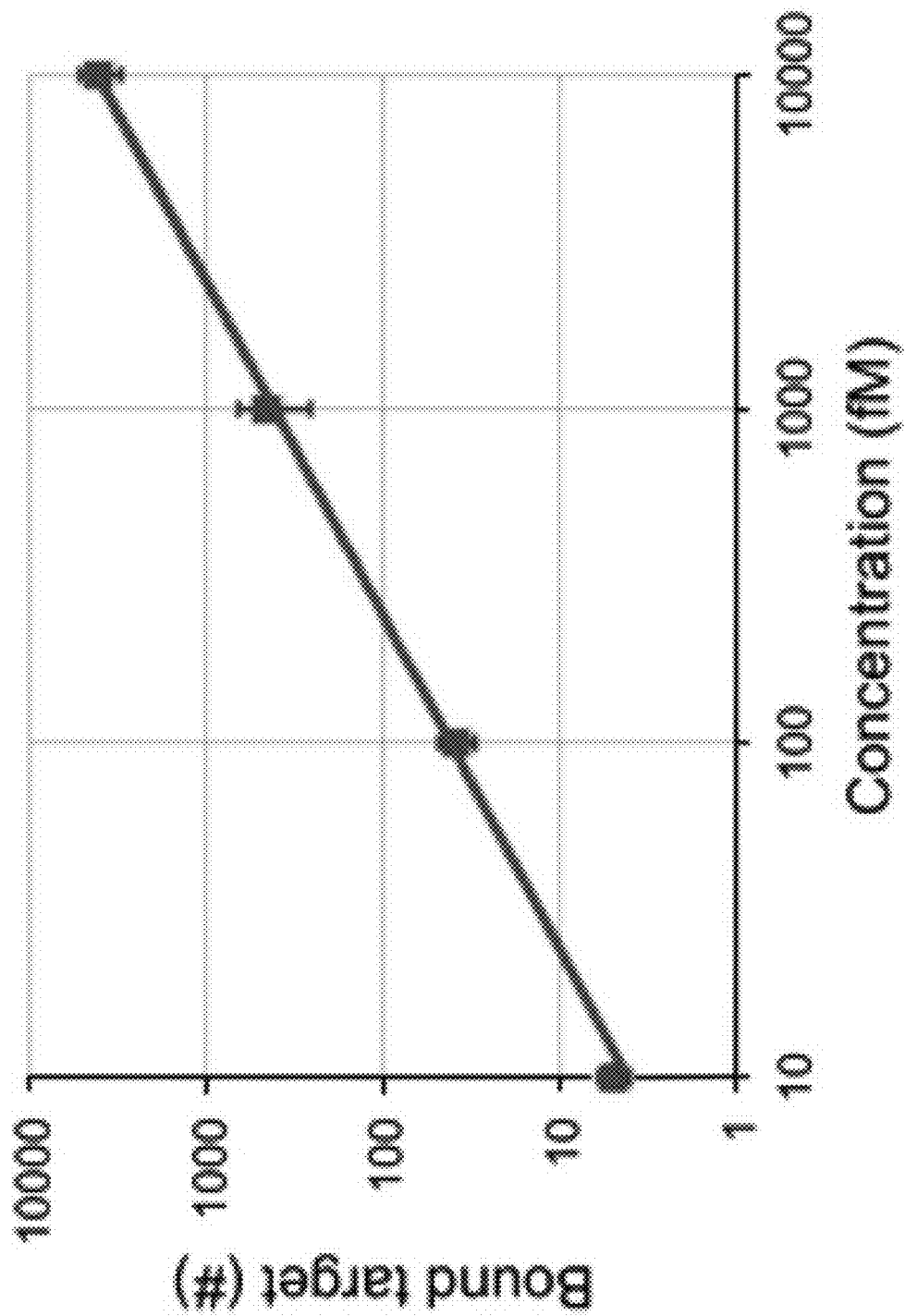
FIG. 14 shows an obtained relationship between the detected number of streptavidin-biotin binding and the concentration of streptavidin in the sample solution.

FIG. 13 shows: (a) a bright view image of a clean SiO$_2$ island surrounded by black silicon after the microfabrication process; (b) a fluorescent image of the FITC labeled DNA dried on the SiO$_2$ island; and (c) detected fluorescence intensity of FITC labeled DNA dried on the SiO$_2$ island. The scale bars are 200 μm. It can be observed from FIG. 12(*b*) that when the fluorescently labelled DNA oligonucleotides solution was completely dried on the SiO$_2$ islands, the molecules were uniformly distributed over the entire hydrophilic surface. The clean background on the black silicon surrounding region suggests that the sample loss due to the liquid/solid boundary movement during evaporation was minimal. FIG. 12(*c*) shows that a concentration lower than 50 fM was detectable above the background noise.

Protein Detection

For streptavidin detection, the hydrophilic islands were pre-anchored with biotin-linked DNA oligonucleotides. The DNA oligonucleotides sequence was: 5' Biotin-AAAAA AAAAA-amine 3' (SEQ ID NO: 1). Target streptavidin was conjugated with quantum dots (e.g., Qdot 525, Life technologies) for visualization. Sample droplets (4 μL, each) with different concentrations of quantum dots-streptavidin complex were spotted on the black silicon template. The assay was incubated at 37° C. to accelerate the evaporation process. The contact area of the droplet is fixed by the hydrophilic surface of the SiO2 island, and the height of the droplet was monitored by a goniometer as the droplet volume decreased by evaporation. When the height of the droplet approached the target value, we optically zoomed in by 25× to closely monitor the droplet height. As soon as the sample droplet shrank to 4 nL, a drop of silicone oil (e.g., S159-500, Fisher Chemical) was employed to encapsulate the sample droplet and stop the evaporation. The assay was further incubated at room temperature for 1 hour before it was dipped in hexane solution to remove the silicone oil. The assay was then cleaned by gentle shaking in TBST buffer and Milli-Q water for 5 minutes and 3 minutes, respectively. After blowing dry with nitrogen, the assay was ready for observation.

The detection sensitivity of the evaporating droplet microarray was tested by varying the target molecule (e.g., nucleic acid or protein) concentration from 10 fM to 100 pM. The bound Q-dots were quantified by using a custom Matlab program. As a control sample, one device area has hydrophilic islands pre-anchored with the scrambled probes, so that any quantum dots left in those areas were due to incomplete wash or non-specific binding. We obtained the real binding events by subtracting the number of non-specifically bound Q-dots from the detected events over the areas with DNA or ligand probes. The final results are shown in FIG. 13, which shows an obtained relationship between the detected number of streptavidin-biotin binding and the concentration of streptavidin in the sample solution.

A linear relationship between the streptavidin concentration and the number of streptavidin-Q-dots bound to the biotin probes was obtained with the streptavidin concentration ranging from 10 fM to 10 pM. For higher target concentration beyond 10 pM, the bonding events were too dense to be resolved microscopically by the specific image processing program used to obtain the relationship. For streptavidin concentration lower than 10 fM, the results were less reliable because the number of non-specific binding could be comparable with the number of specific binding. The amount of non-specific binding can be reduced by optimizing the washing conditions and proper surface treatments of the SiO$_2$ islands. Furthermore, the variation of the measurements can be further reduced by improved control of the droplet evaporation process through automation.

The Detection of miRNA Mimic Oligonucleotides

An exemplary sequence of anchor probe oligonucleotides is: 5' TGCGA CCTCA GACTC CGGTG GAATG AAGGA AAAAA AAAAA-amine 3' (SEQ ID NO: 2). The exemplary target is miRNA 205 mimic oligonucleotides with a sequence of: 5' TCCTT CATTC CACCG GAGTC TGAGG TCGCA-biotin 3' (SEQ ID NO: 3). miRNA 205 mimic was used here because miR205 has been reported as a specific biomarker for squamous cell lung carcinoma. The hybridization buffer (2% BSA, 50 mM borate buffer, 0.05% sodium azide, pH 8.3) was diluted 1000 fold before the target oligonucleotides were mixed in. Sample droplets (4 μL each) of different concentrations of miRNA 205 mimic oligonucleotides were pipetted to the black silicon template to form micro-droplets. After the evaporation and oil encapsulation process described previously, the assay was incubated at 50° C. to facilitate hybridization. In the last step, streptavidin conjugated quantum dots (1 nM) was introduced to label those hybridized DNA duplex.

Figure 15:
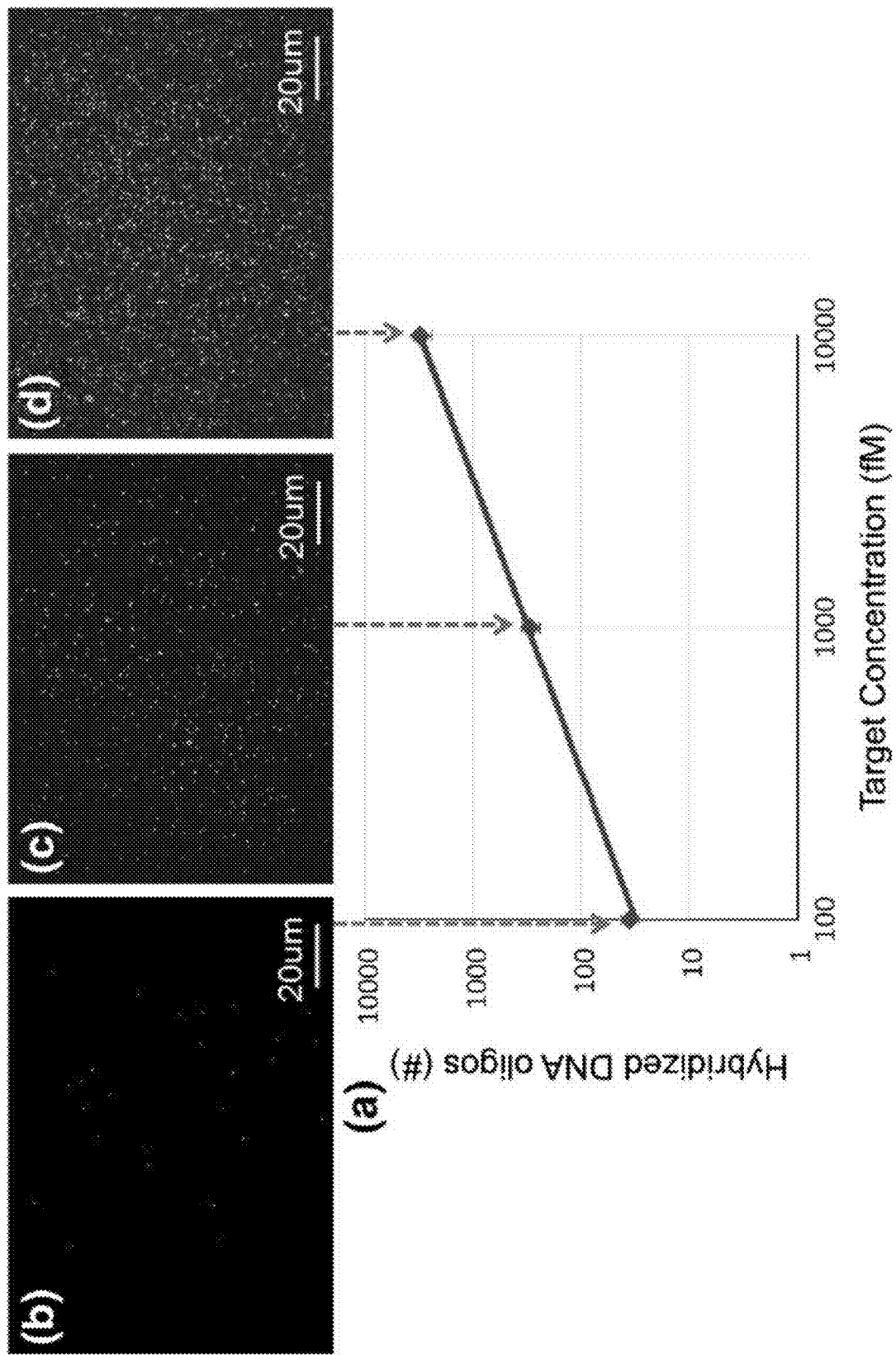
FIG. 15 shows: (a) a dependence plot of the number of hybridized targets and the concentration of target molecules in the sample; (b-d) the processed images of visualized quantum dots with a target concentration of 100 fM, 1 pM, and 10 pM, respectively.

FIG. 15 shows: (a) a dependence plot of the number of hybridized targets and the concentration of target molecules in the sample; (b-d) the processed images of visualized quantum dots with a target concentration of 100 fM, 1 pM, and 10 pM, respectively. As was shown in FIG. 15(a), a linear relationship between the number of detected hybridized target and the DNA target concentration was obtained. Hence, we have achieved a sensitivity of 100 fM with a dynamic range of 2 orders of magnitude. Yet in another embodiment of the disclosed technology, which includes a similar process but with a larger volume (1 mL) of initial DNA containing sample, a sensitivity of 50 aM with a dynamic range of 4 orders of magnitude has been achieved. This embodiment is discussed later on in this patent disclosure, e.g., see FIG. 25C. By optimizing the hybridization conditions such as the incubation temperature, DNA probe density, and salt concentration by varying the buffer dilution factor, the detention sensitivity is expected to be further increased.

Discussion

A novel oil-encapsulated micro/nano-droplet (e.g., microliter volume or nanoliter volume or less) array reactor for biosensing applications has been demonstrated. The disclosed design has addressed the inherited slow, passive diffusion limitation commonly observed during DNA hybridization or protein-ligand binding by drastically decreasing the height of the reaction aqueous layer. Furthermore, the design greatly enriches the concentration of target molecules by several orders of magnitude in a controllable manner. Specifically, this enrichment procedure does not introduce amplification bias commonly found in thermal cycling or reverse transcription process (i.e., the enrichment factors for all the molecules are substantially the same and independent of the GC contents of target DNAs). Hence, the disclosed system and technique may be used as a hybridization platform for direct detection of molecular markers of low abundance without requiring the enzymatic amplification process such as PCR, and offers a cost-effective, fast solution for point-of-care in-vitro diagnosis.

Embodiments of the oil-encapsulated evaporating-droplet molecular-detector platform are based on the fabrication of hydrophilic islands surrounded by a hydrophobic or superhydrophobic surface. The hydrophobic or superhydrophobic surface yields very large contact angle (~160 degrees) and eliminates the coffee ring effect caused by the receding boundary of the droplet. Black silicon is chosen to form the hydrophobic or superhydrophobic surface because the nanopillars that give black silicon its optical and hydrophilic properties are formed naturally during the deep reactive etching to form the black silicon, thereby avoiding the slow and expensive steps of fabricating nanopatterns over a large area.

In some implementations, protocols have been developed to precisely control the evaporation process. Goniometer was used to closely monitor the evolution of the droplets during evaporation. Oil encapsulation terminated the evaporation process and formed a stable environment for the micro/nano-droplet (e.g., microliter volume or nanoliter volume or less) reactor without being affected by the outside environment such as humidity. Preliminary data has shown a detection sensitivity of 10 fM for streptavidin as a protein target and <0.1 fM (e.g., 50 aM) for miRNA mimic oligonucleotides. A linear response was obtained for a concentration range spanning nearly 4 orders of magnitude. The detection sensitivity may be further enhanced by optimizing the hybridization conditions and reducing the diameters of hydrophilic islands. Furthermore, the device architecture can be easily scaled to increase the throughput and miniaturized footprint to support various molecular detection purposes desirable for point-of-care applications.

Exemplary Techniques and Devices for Glioblastoma Diagnosis

Glioblastoma can be used to assess the disclosed technology because it is a dominant form of brain tumor. Detection at an early stage provides significant benefits for intervention options to improve the prognosis outcome. Currently, glioblastoma is primarily diagnosed by CT, MRI and pathological examination of biopsy. Lack of a robust molecular marker has prevented a timely and effective diagnosis solution to this day. Recently, researchers have identified the presence of microRNA-21 (miR-21) in the extra-cellular vesicles (EVs) as a unique molecular signature secreted by glioblastoma cells. Utilizing miRNAs as oncogenic marker has sometimes raised concerns over reliability of normalization standards. To address this issue, an EV-based normalization technique has been developed, accompanied by a minimum copy number cut-off protocol without the need for controversial "reference transcripts" such as GAPDH, 18S rRNA, and hsa-miR-103. Based on the absolute number of miR-21 per EV particle assessment, the disclosed technique has demonstrated the capability to quantitatively distinguish between cerebrospinal fluid (CSF) derived from glioblastoma and from non-oncologic patients.

Based on the concept of utilizing EV-associated miR-21 in combination with potentially additional miRNAs as a biomarker panel (e.g. miR-92b, miR-128 and miR-192), an in-vitro platform has been developed for reliable and accurate detection of miRNAs in CSF for early prognostication of glioblastoma. The disclosed lab-on-a-chip device in this patent document can be used to enrich, detect, and quantify specific miRNA markers from CSF. As a platform technology, it can be applied to a large number of other diseases beyond glioblastoma diagnosis, including lung, pancreatic, kidney, breast, liver cancer etc., as well as cardiac vascular diseases (CVDs) and immune disorders. Moreover, the disclosed platform is expected to be highly quantitative and more sensitive to the current nucleic-acid based diagnosis, and allows rapid, early detection at less than $\frac{1}{10}$ of today's cost using a device that is $\frac{1}{10}$ of the cost of image-based systems. Table 1 shows comparisons between some existing and emerging technology platforms and the disclosed nucleic acid/miRNA technology.

TABLE 1

Comparisons with current and emerging nucleic acid/miRNA technology platforms

| Technology | Manufacturer | Processing time (post extraction) | Detection limit | Sample volume | Amplification | Instrument cost | Consumable and Reagent cost |
|---|---|---|---|---|---|---|---|
| qPCR | Life Tech., BioRad, Perkin Elmer | 2 hr+ | pM | 15-100 uL/reaction | Required | $20K | $100-$200/96 well plate |

TABLE 1-continued

Comparisons with current and emerging nucleic acid/miRNA technology platforms

| Technology | Manufacturer | Processing time (post extraction) | Detection limit | Sample volume | Amplification | Instrument cost | Consumable and Reagent cost |
|---|---|---|---|---|---|---|---|
| Digital PCR | Formulatrix, Life Tech | 2 hr+ | pM | 10-100 uL/reaction | Required | $100K | $100-$200/96 well plate |
| Sequencing | Illumina, Roche 454, Life Tech | 2-7 days | pM | 10-50 ul/reaction | Required | $50K-$700K | $5,000 per flowcell |
| This Patent Disclosure | UCSD/ Compliance Decisions | 30 min | 0.1 fM | No limitation | Not required | <$5K | <$20 per 8 samples |

Overall Architecture Design and Concepts

The disclosed technology includes (a) lab-on-a-chip device architecture to perform enrichment and detection without miRNA-specific label, (b) an evaporating droplet material to enrich miRNAs, (c) oil-encapsulated reaction chambers (e.g., nano or microliter volume) for efficient and reproducible miRNA hybridization, and (d) detection and quantification of miRNAs using the "stacking effect". Implementations of the disclosed technology can facilitate achieving: parallel operation with multiple (>8) samples, simultaneous detection of multiple RNA/DNA cancer markers, large enrichment without amplification, and sub-femto-molar sensitivity with high accuracy and specificity.

In some implementations, the disclosed device handles miRNAs (or any nucleic acid) cancer markers that are extracted from either extra-cellular vesicles or Aga-protein in blood, biofluids, or CSF. Specifically, the platform will be validated with short nucleic acid oligos spiked in the nuclease-free water identical to the miR-21 sequence extracted by the mirVANA kit (Life Technologies) optimized for purification of RNA species <200 bps. The protocol is proven and cost effective, and can be readily applicable to miRNA extraction from CSF for clinical samples.

The disclosed device includes an array of hydrophilic micro-islands or microarray of hydrophilic islands surrounded by super hydrophobic black silicon. The hydrophilic islands includes $SiO_2$ coated Si with DNA probes that are complimentary to the miR targets.

FIGS. 16A-16F summarizes an exemplary device design and operation process flow. Note that FIGS. 16A-16F provide a different enrichment process from the enrichment process described in conjunction with FIGS. 1A-1F.

Figure 16A:
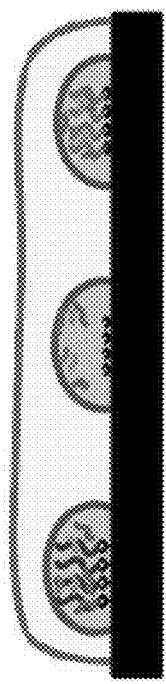
FIG. 16A shows putting miRNA containing RNAse-free deionized water over microarray of islands or micro-islands functionalized with specific DNA oligo probes.
Figure 16B:
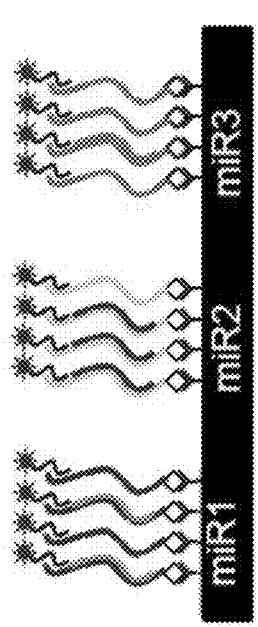
FIG. 16B shows water is evaporated and miRNAs are condensed to microarray of islands or micro-islands.

More specifically, FIG. 16A shows putting miRNA containing RNAse-free deionized water over micro-islands functionalized with specific DNA oligo probes. The microarray of islands or array of micro-islands are surrounded by super-hydrophobic surface formed by black silicon and separated by Teflon-coated grids. The extracted miR sample from 0.1-1 mL CSF simulant from the mirVANA kit is suspended in RNase free deionized water over a Teflon grid that matches the patterns of the microislands. The device is heated to 95° C. to accelerate water evaporation. FIG. 16B shows water is evaporated and miRNAs are condensed to the microarray of islands or array of micro-islands. As the liquid is evaporated to become droplets (10-30 μL), the temperature is reduced from 95° C. to 60° C. to assure the liquid remains in the Cassie state (i.e. slippery droplet over the black Si) instead of in the Wenzel state (i.e. droplet pinned to the black Si). This process leads to miRNA condensation on the microislands when the liquid is completely dried out.

Figure 16C:
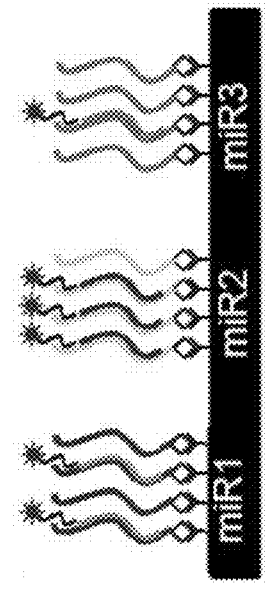
FIG. 16C shows dipping the device into hybridization buffer to form self-assembled nano-droplets (e.g., nanoliter volume or less). The hybridization buffer also contains quantum dots linked with DNA oligos.

Next the entire device that contains the condensed miRNAs is dipped in the hybridization buffer with suspension of quantum-dot conjugated reporter DNAs for detection using the stacking effect (described below). FIG. 16C shows dipping device into hybridization buffer to form self-assembled nano-droplets (e.g., nanoliter volume or less), the hybridization buffer also contains quantum dots linked with DNA oligos. Because of the properties from surface energy engineering, a uniform array of nano-droplets (around 0.2 nL each) is formed as soon as the wafer is removed from the buffer.

Figure 16D:
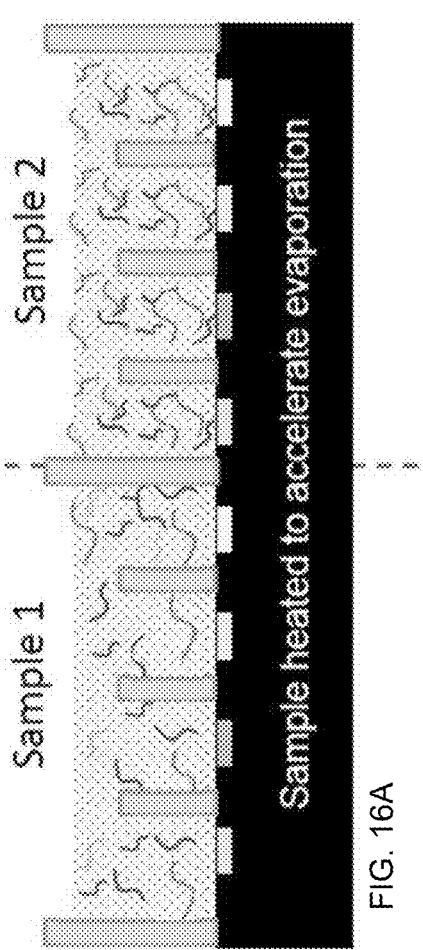
FIG. 16D shows oil encapsulation of the nano-droplets (e.g., nanoliter volume or less) to form hybridization chambers.
Figure 16E:
FIG. 16E shows miRNAs and quantum-dots linked reporter oligos are hybridized with DNA probes on each island.

Next, a layer of oil is applied to encapsulate the nano-droplets (e.g., nanoliter volume or less), forming an array of stable, well-controlled hybridization chambers (e.g., nano or microliter volume). FIG. 16D shows oil encapsulation of the droplets to form hybridization chambers (e.g., nano or microliter volume). Due to the small volume of the hybridization chamber (e.g., nano or microliter volume) and the isolation of the reaction chambers (e.g., nano or microliter volume) from the influences of outside environments (humidity, edge effect, etc.), hybridization between the target miRNAs and the complementary probes and the Q-dot conjugated reporting DNAs occur at high efficiency, resulting in significant improvements in sensitivity and hybridization time (from >10 hours in a 96-well plate to <10 minutes). In some embodiments, after the completion of the hybridization, the process also includes removing the layer of oil and the hybridization buffer to expose the DNA oligo probes, as shown in FIG. 16E. FIG. 16E shows miRNAs and quantum-dots linked reporter oligos are hybridized with DNA probes on each island.

Figure 16F:
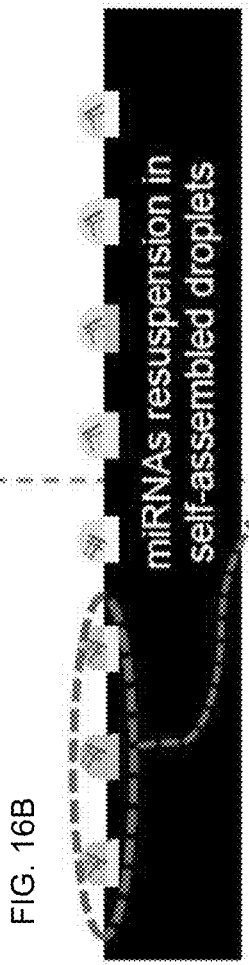
FIG. 16F shows using the stacking effect to selectively remove reporter oligos from probes without miRNA hybridization.

FIG. 16F shows using the stacking effect to selectively remove reporter oligos from probes without miRNA hybridization. After washing away extra reporting DNA oligos linked with Q-dots, the device is heated or experiences shear stress from a relatively strong flow. Because of the "stacking effect", the reporting oligos attached to DNA probes hybridized with a miRNA molecule have a higher melting temperature (Tm) than the reporting oligos attached to those DNA probes without miRNA hybridization. Quantum dots can be retained on those miRNA hybridized probes but not on those probes without miRNA hybridization. The concentration of the specific miRNA can then be obtained by measuring the fluorescent intensity of each micro-island or by counting the number of quantum dots using software such as ImageJ. By detecting the Q-dot fluorescent intensity, each miRNA cancer marker can be detected and quantified.

miRNA Enrichment Using Evaporating Droplets

To detect and quantify miRNAs without amplification, it is necessary to enrich the miRNA concentration significantly. This disclosed technology in conjunction with FIGS. 16A-16F provides an effective, repeatable approach to enrich the miRNA concentration by up to 500,000 times, which may be calculated from the initial (spiked) miRNA concentration in CSF simulant to the final miRNA concentration within the oil-encapsulated nano-droplet (e.g., nanoliter volume or less) hybridization chambers. The enrichment factor is achieved from the ratio of initial sample volume (0.1-1 mL) and the final volume of the nano-droplet (200 pL per droplet), giving rise to an enrichment factor of >500,000 assuming no miR loss in the process. Because of the hydrophobicity or superhydrophobicity of black silicon surrounding the hydrophilic islands to suppress the coffee-ring effect, minimum sample loss is expected.

Figure 17C:
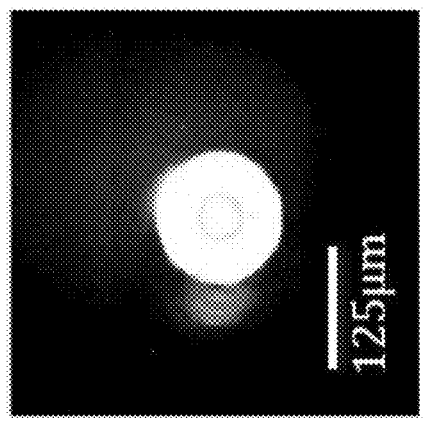
FIG. 17C shows sample enrichment from the evaporating droplets, wherein the fluorescently labeled DNA oligos are condensed onto a 125 μm diameter hydrophilic surface area.
Figure 17B:
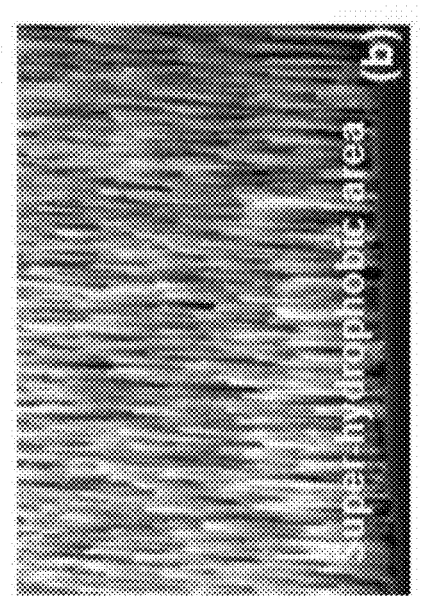
FIG. 17B shows an SEM micrograph of the black Si area.
Figure 17A:
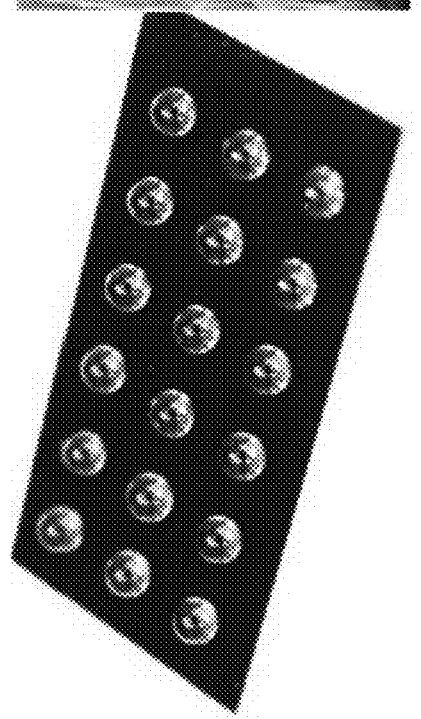
FIG. 17A shows photographic image of a droplet array self-assembled on $SiO_2$ islands surrounded by black silicon.

FIGS. 17A-17C show photographic images of nucleic acid enrichment on hydrophilic islands surrounded by super-hydrophobic black Si. FIGS. 17A-17C may be used to prove the concept of sample enrichment using evaporating droplets. In the examples shown, fluorescently labeled DNA oligos were added to the liquid. FIG. 17A shows photographic image of a droplet array self-assembled on $SiO_2$ islands surrounded by black silicon. FIG. 17B shows an SEM micrograph of the black Si area. The black Si properties are caused by the nanostructures and the material properties of etched Si. FIG. 17B shows sample enrichment from the evaporating droplets, wherein the fluorescently labeled DNA oligos are condensed onto a 125 μm diameter hydrophilic surface area. As can be seen in FIG. 17C, at the end of the enrichment process, DNAs were concentrated to the 125 μm diameter hydrophilic surface, and the surrounding super-hydrophobic black silicon eliminates the undesirable "coffee ring effect" that traps nucleic acids during the droplet drying process.

Oil-Encapsulated Reaction Chambers (e.g., Nano or Microliter Volume) for Efficient miRNA Hybridization The hybridization efficiency between the target nucleic acid and the DNA probe is a significant factor of variation for quantitative detection of nucleic acid (e.g., miRNA) markers. To obtain accurate and repeatable results, the equilibrium state of nucleic acid/DNA binding needs to be obtained. The following analyses and FIGS. 18A-18C show that the proposed exemplary oil-encapsulated nano-droplet (e.g., nanoliter volume or less) hybridization chamber design can enable (a) drastic reduction of reaction time from ~10 hours to <10 minutes and (b) high hybridization efficiency.

Figure 18A:
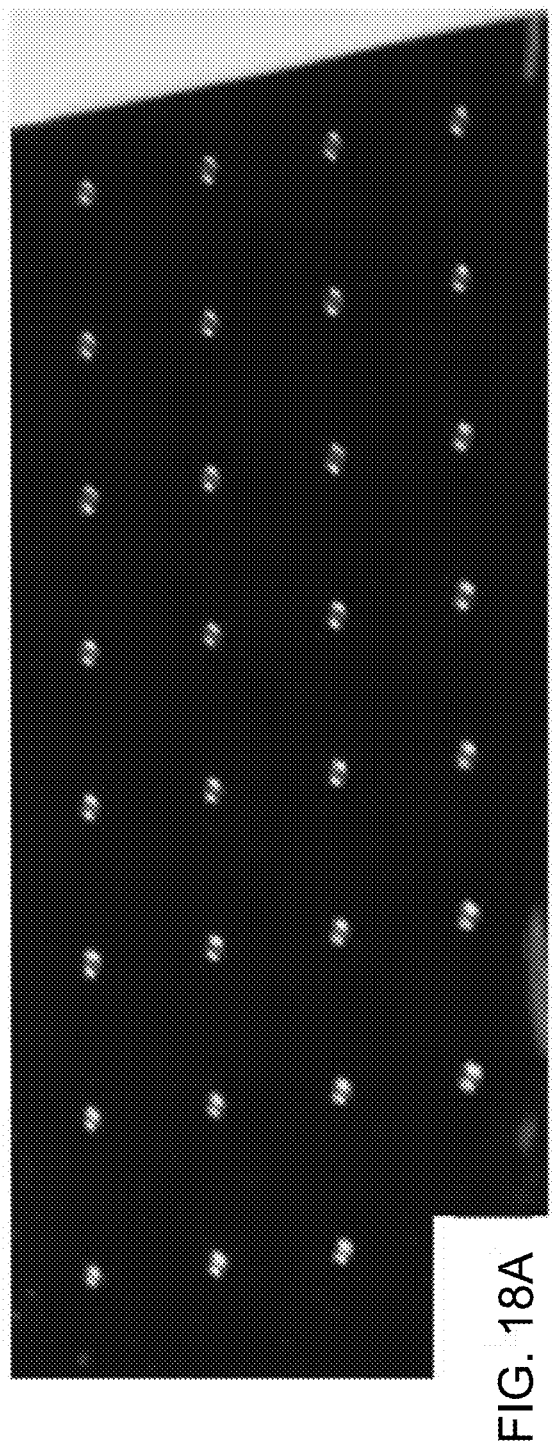
FIG. 18A shows an example of self-assembled nano-droplets (e.g., nanoliter volume or less) after dipping the miRNA condensed sample into hybridization buffer.
Figure 18C:
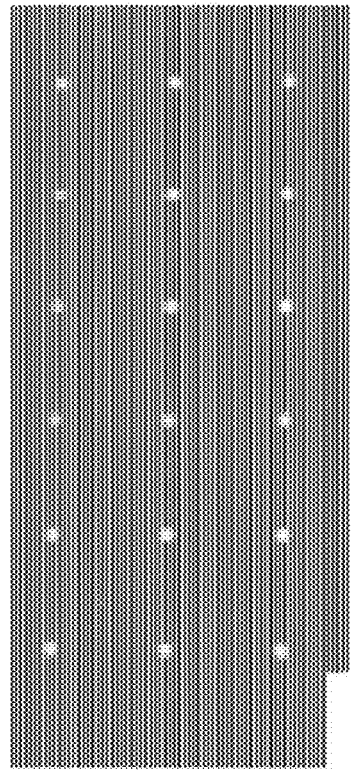
FIG. 18C shows fluorescence from Q-dots to show the formation of miRNA/DNA duplex within the reaction chambers.
Figure 18B:
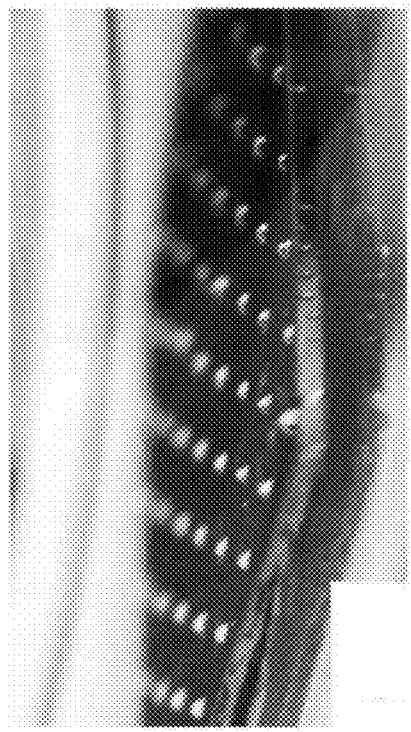
FIG. 18B shows an example of oil encapsulated nano-droplet (e.g., nanoliter volume or less) hybridization cambers.

FIGS. 18A-18C show preliminary results following the process flow in FIGS. 16A-16F. FIG. 18A shows an example of self-assembled nano-droplets (e.g., nanoliter volume or less) after dipping the miRNA condensed sample into hybridization buffer. FIG. 18B shows an example of oil encapsulated nano-droplet (e.g., nanoliter volume or less) hybridization cambers and FIG. 18C shows fluorescence from Q-dots to show the formation of miRNA/DNA duplex within the reaction chambers (e.g., nano or microliter volume).

The kinetics of the hybridization process has been described previously by Equation (1), which can be solved analytically to yield the time dependence of hybridization efficiency, η(t) and Equation (2). From Equation (2), the time to reach equilibrium is proportional to $L^2/D$ provided there exist enough number of probes for miRNA to hybridize with, which can be obtained in the exemplary designs. For miRNAs with D being in the order of $10^{-7}$ cm$^2$/s, it takes longer than 100 hours for the reaction to reach equilibrium in a typical reactor (e.g. 96-well plate) with a liquid height of millimeters. By reducing the liquid thickness to 20 μm (for 0.2 nL droplet volume), the time to reach equilibrium state is reduced by more than 1,000 times to be as short as 5 minutes, which was experimentally demonstrated and results are shown in FIG. 19.

Figure 19:
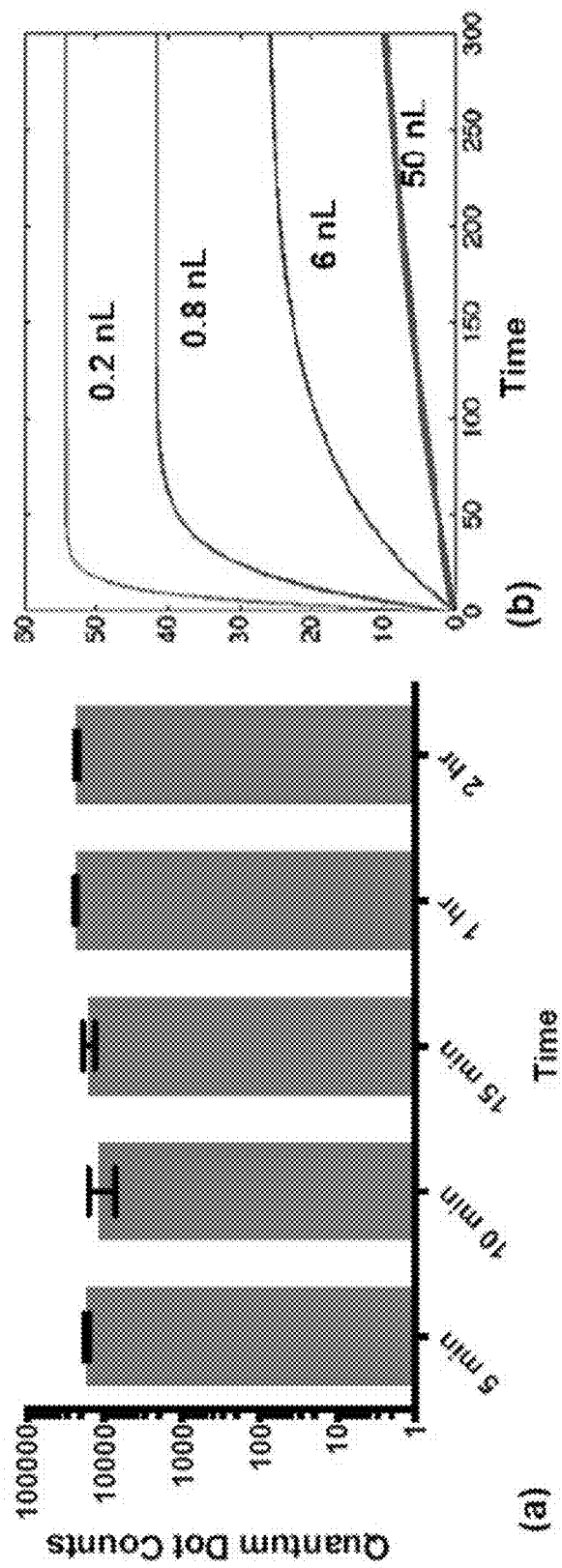
FIG. 19 shows (a) greatly reduced hybridization time with the oil-encapsulated nano-droplet (e.g., nanoliter volume or less) hybridization chamber; and (b) simulated time dependent DNA hybridization efficiency with different liquid volume.

FIG. 19 shows (a) greatly reduced hybridization time with the oil-encapsulated nano-droplet (e.g., nanoliter volume or less) hybridization chamber; and (b) simulated time dependent DNA hybridization efficiency with different liquid volume. With 200 μL volume in most conventional devices, the reaction takes 16-24 hours to reach the equilibrium state. Using the disclosed device, the reaction can be completed in <5 minutes.

Design and Fabrication of Black Silicon Templates for Droplet-Based miRNA Enrichment In some implementations, the disclosed lab-on-a-chip device includes an array of hydrophilic micro-islands or microarray of hydrophilic islands surrounded by super-hydrophobic black silicon fabricated on a commercial Si wafer. To form black silicon, the Bosch etching process can be employed in a reactive ion etcher. The etch process includes alternating cycles of etching ($SF_6$) and passivation ($C_4F_8$) to form nanopillar structures. For areas that are protected by lithographically defined $SiO_2$ patterns, no etching or passivation occurs so the hydrophilic properties are preserved after the black silicon forming process. To construct a detector using the template, the 2D array of hydrophilic micro-islands or microarray of hydrophilic islands is coated with specific DNA probes matching specific miRNA targets.

The miRNA extracted from CSF simulant (0.1-1 mL) is suspended in RNAse free deionized water before being dispensed to the lab-on-a-chip device with Teflon coated grids (see FIG. 16A). At a concentration of 1 fM, 100 μL CSF simulant contains 60,000 molecules, which gives rise to sufficient signal intensity and low statistical noise. In some embodiments, the enrichment factor may be characterized under different miRNA concentrations and evaporation and wash conditions.

Development of Process for High Sensitivity (<1 fM), Quantitative, and Specific miRNA Detection 1. miRNA Hybridization in Oil-Encapsulated Reaction Chambers (e.g., Nano or Microliter Volume):

As discussed previously, the hybridization efficiency and process reproducibility can be greatly enhanced with a reduced thickness of the liquid layer. After the miRNA condensed sample is dipped into the hybridization buffer to form a self-assembled droplet array, the self-assembled droplet array can be used to characterize the following parameters: (a) the optimal composition of the hybridization buffer (e.g., its PH value and ionic strength); and (b) the concentration and properties (e.g., surface charge) of Q-dot linked DNA oligos in the hybridization buffer to minimize Q-dot residues due to incomplete wash.

Figure 20:
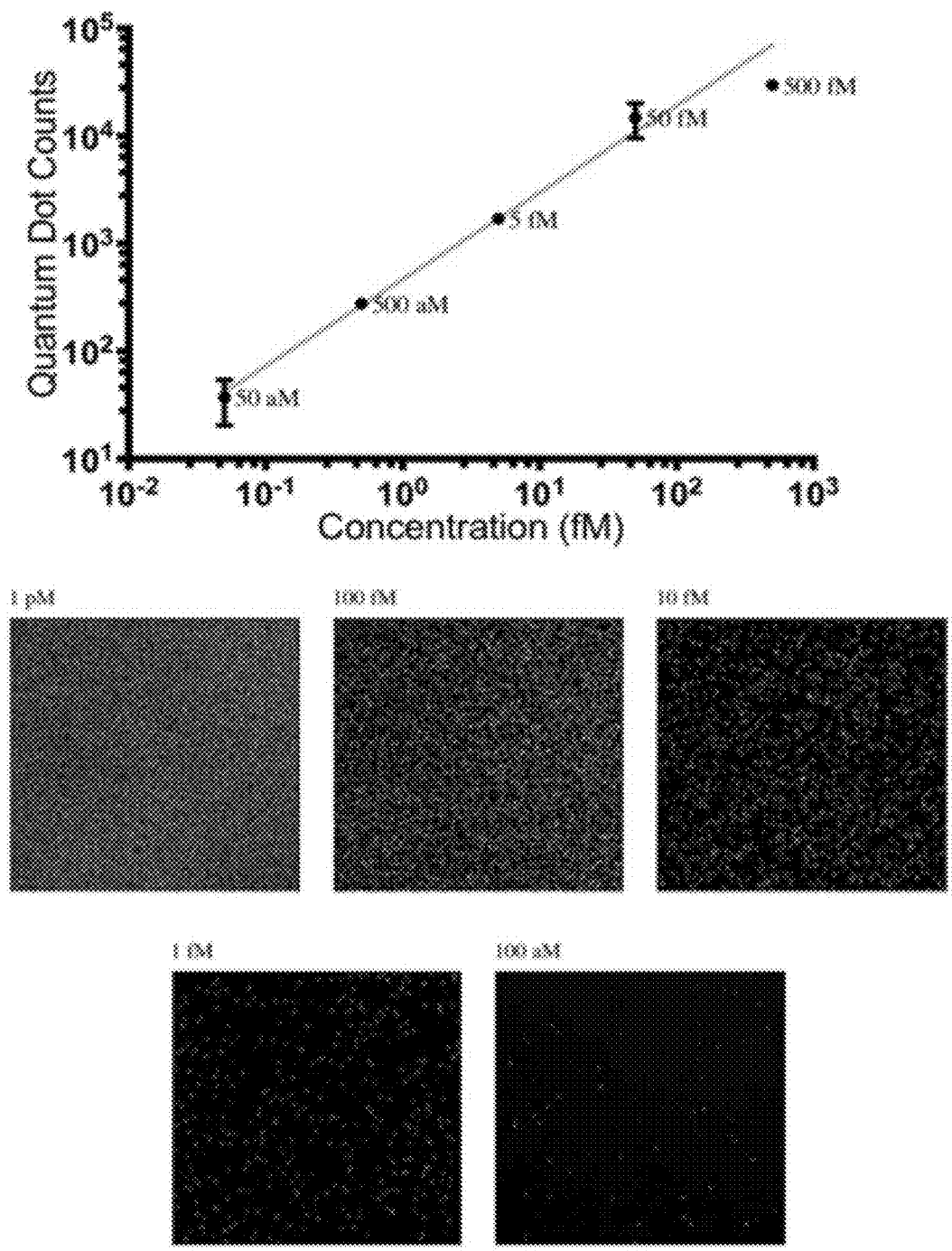
FIG. 20 shows preliminary sensitivity measurement of the disclosed device containing synthesized miR205 and obtained based on the process of FIGS. 16A-16F.

FIG. 20 shows preliminary sensitivity measurement of the disclosed device containing synthesized miR205 and obtained based on the process of FIGS. 16A-16F. More specifically, FIG. 20 shows a dependence plot of the number of Q-dots and the concentration of target molecules in the sample (the upper plot); and the processed images of visualized quantum dots with a target concentration of 100 aM, 1 fM, 10 fM, 100 fM, and 1 pM, respectively (the bottom images). As shown by the dependence plot, a linear relationship between the number of detected Q-dots and the target molecule concentration is obtained. Preliminary results with miR205 have shown that the device can obtain sensitivity of 50 aM (0.05 fM) even though there is still room for improvement in the reproducibility of the detection to assure repeatable (<20% run-to-run variation) and quantitative results. In these embodiments, quantum dots are used over fluorescent molecules because one can count individual quantum dots that signify the hybridization of each single miRNA molecule. This property enables researchers to visualize and precisely measure the enrichment and hybridization efficiency of target miRNAs, offering great advantages during the R&D phase to optimize the device process and protocols.

2. miRNA Detection and Quantification Using the Stacking Effect

FIGS. 21A-21C show schematics of miRNA cancer marker detection and quantification using Q-dot linked reporting oligo and stacking effect. FIG. 21A shows an exemplary design of a DNA probe and Q-dot linked reporter oligo. The stacking effect produces a melting temperature difference for the reporter oligo between miRNA hybridized and unhybridized probes. In some implementations, different DNA probes that are designed to match different target miRNAs have the same sequence for the first 8 nucleotides so that substantially all the probes can hybridize with the Q-dot linked reporting DNA oligos, as shown in FIG. 21A.

FIG. 21B shows an exemplary device schematic for detection and quantification of different miR cancer markers and the on-chip negative control, and the process of using the stacking effect to selectively remove the Q-dot linked reporter oligos from probes without hybridized target miRNAs. After washing off extra Q-dot linked reporter DNA oligos, the molecular probes can be in two possible states: probes hybridized with reporter DNA but without the target miRNAs and probes hybridized with both the target miRNAs and the reporter DNA. Because of the stacking effect, the binding strength of the DNA oligos is enhanced by the hybridized miRNAs that are immediately next to the DNA oligos with a nick. Control areas are provided where molecular probes are mismatched to any human miRNAs. The Q-dot signals during heating or flushing can be recorded, wherein the heating or flushing usually takes <10 minutes.

Next, it is possible to analyze how the number of quantum dots in each area varies over time, thus can be used to produced curves similar to those in FIG. 21C. FIG. 21C shows an exemplary plot of anticipated time-dependent fluorescent signals from each specific miR cancer marker shown in FIG. 21B and the control signal. From this study, one can obtain background level due to instrument noise, non-specific binding, and incomplete wash of extra quantum dots. Such information will help process optimization and signal processing to further improve the accuracy of the test. The on-chip control signal allows for removing the effects of non-specific binding, background noise, and residues due to incomplete wash.

Verification of the Device Efficiency, Repeatability, Accuracy, and Utility

In some embodiment, the disclosed device is validated by quantitatively detecting the levels of glioblastoma miRNA marker (miR-21) over the relevant range from 1 fM to 100 fM. The tests can be performed using spiked synthetic miRNA oligos. The validation process can include the following calibration steps.

Calibration of variations in miRNA enrichment factor by the droplet process: A known amount of synthetic, fluorescently labeled miR-21 can be introduced into the sample. The emission intensity from each run gives rise to the run-to-run variation of the miRNA enrichment and hybridization efficiency.

Calibration of the "stacking effect": The denaturing of reporter DNA oligo from the probes is generally a stochastic process. To produce an accurate reading of the miRNA level, the signal will be measured with and without synthetic miR-21. The temporal response of the emission signal with and without target miRNAs produces data about the kinetics of the denaturing process. These curves can be used to (a) optimize the denaturing process control (i.e. temperature and flow rate); and (b) find the statistical properties (mean and sigma) of the "stacking effect". Similar curves can also be generated using qPCR to serve as data for cross-platform comparisons.

Calibration of non-specific binding: During the process development, one can use test probes made to have one or two nucleotides mismatch from the target miRNA, and can test miRNAs of different GC contents. The binding event detected from those "test probes" can help to identify the extent of non-specific binding. In addition to optimization of device design and experimental conditions, data analysis and Q-dot specific image quantification techniques can be developed to minimize uncertainties caused by non-specific binding.

Figure 22A:
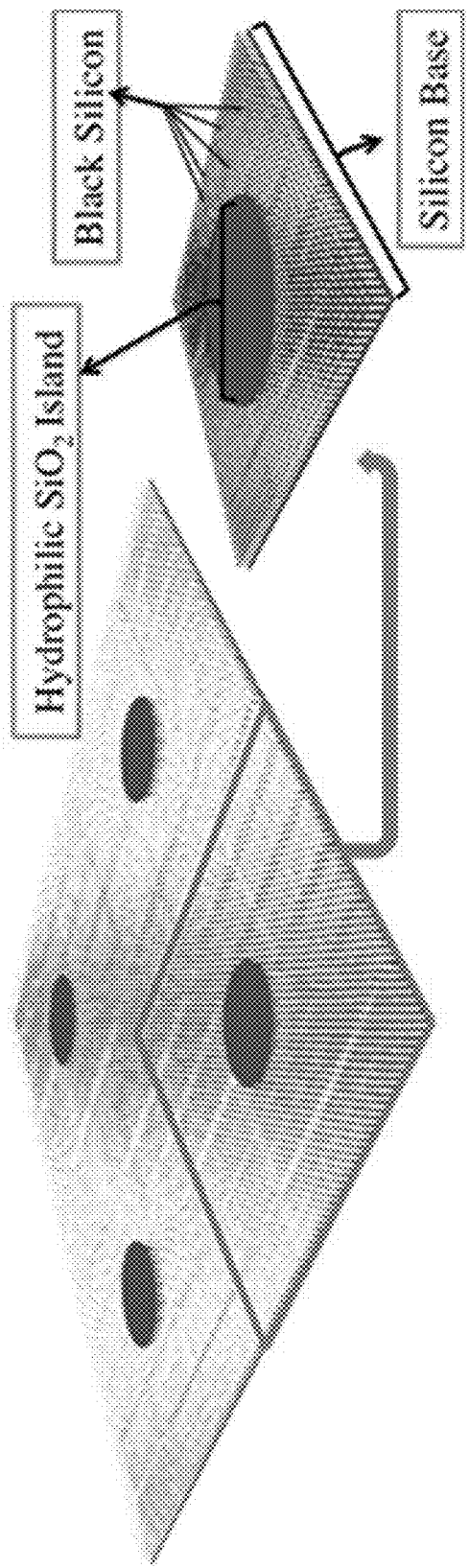
FIG. 22A shows a 2×2 $SiO_2$ array device with circular $SiO_2$ patterns surrounded by super-hydrophobic black silicon.
Figure 22C:
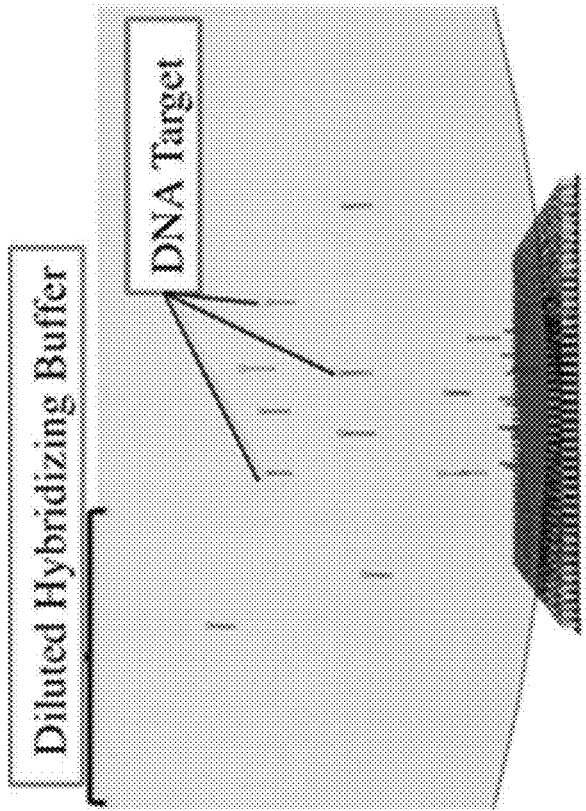
FIG. 22C shows DNA targets solubilized in diluted hybridization buffer are added onto SiO2 surface and allowed to evaporate.
Figure 22B:
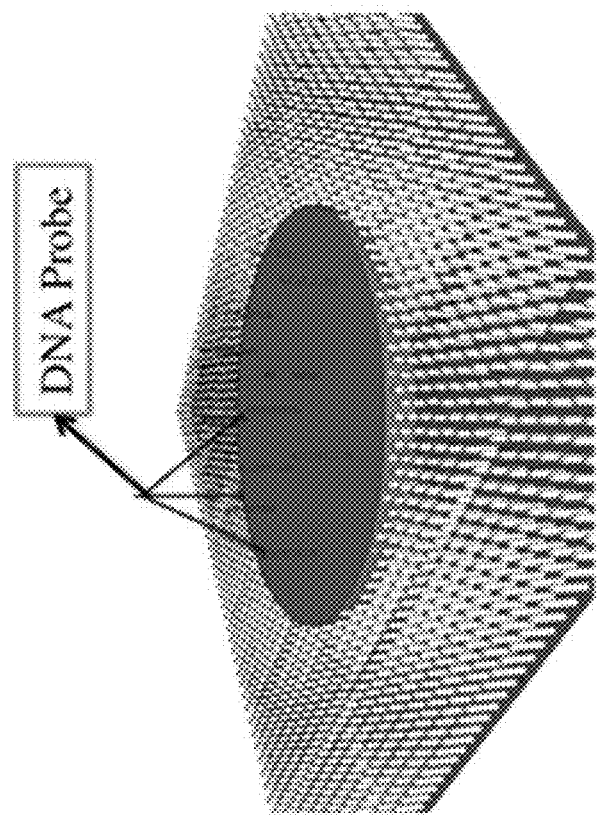
FIG. 22B shows DNA probes are chemically cross-linked to SiO2 pattern surfaces.
Figure 22D:
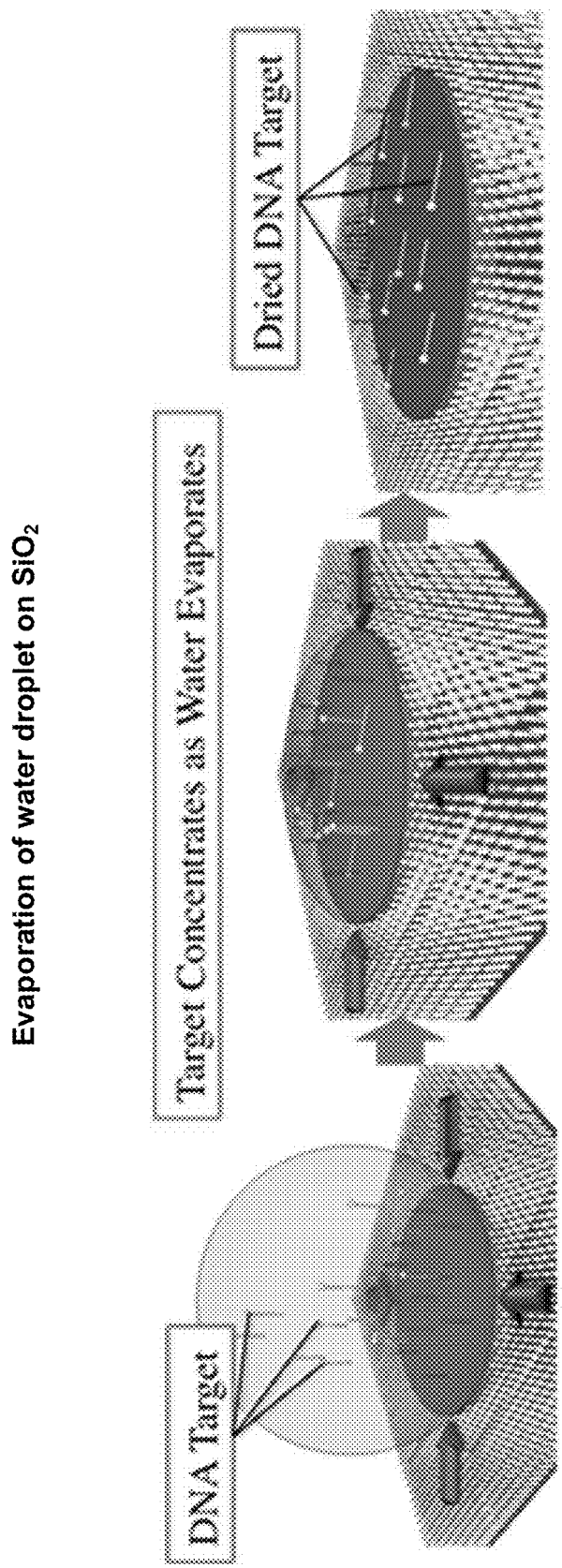
FIG. 22D shows that while evaporating, the target solution droplet realigns itself onto the $SiO_2$ pattern, reduces in size, concentrates, and dries completely.

Massively Parallel Nano-Droplet (e.g., Nanoliter Volume or Less) Microarray for Ultrasensitive Nucleic Acid Quantification Detailed Embodiment of the Disclosed Technology An ultra-sensitive nucleic acid quantification workflow performed on a super-hydrophobic, nano-patterned microarray device is disclosed. The workflow utilizes device surface super-hydrophobicity to form self-assembled nano-droplet (e.g., nanoliter volume or less) array, which is massively parallel in nature and exhibits precise droplet volume control and extreme concentration enrichment. FIGS. 22A-22G show a process flow of nano-liter droplet array formation, surface hybridization reaction, and quantum dots labeling on a nano-droplet (e.g., nanoliter volume or less) microarray device including an array of 400 um, circular $SiO_2$ pattern surrounded by super-hydrophobic black silicon surfaces. FIG. 22A shows a 2×2 $SiO_2$ array device with circular $SiO_2$ patterns surrounded by super-hydrophobic black silicon. For nucleic acid quantification, the following steps are implemented in the nano-droplet (e.g., nanoliter volume or less) microarray workflow: (1) DNA probes are chemically cross-linked to SiO2 pattern surfaces (see FIG. 22B). Next, DNA targets solubilized in deionized water or diluted hybridization buffer are added onto SiO2 surface to form droplets of the target solution and the target solution is allowed to evaporate (see FIG. 22C). While evaporating, the target solution droplet realigns itself onto the $SiO_2$ pattern, reduces in size, concentrates, and dries completely (see FIG. 22D).

Figure 22E:
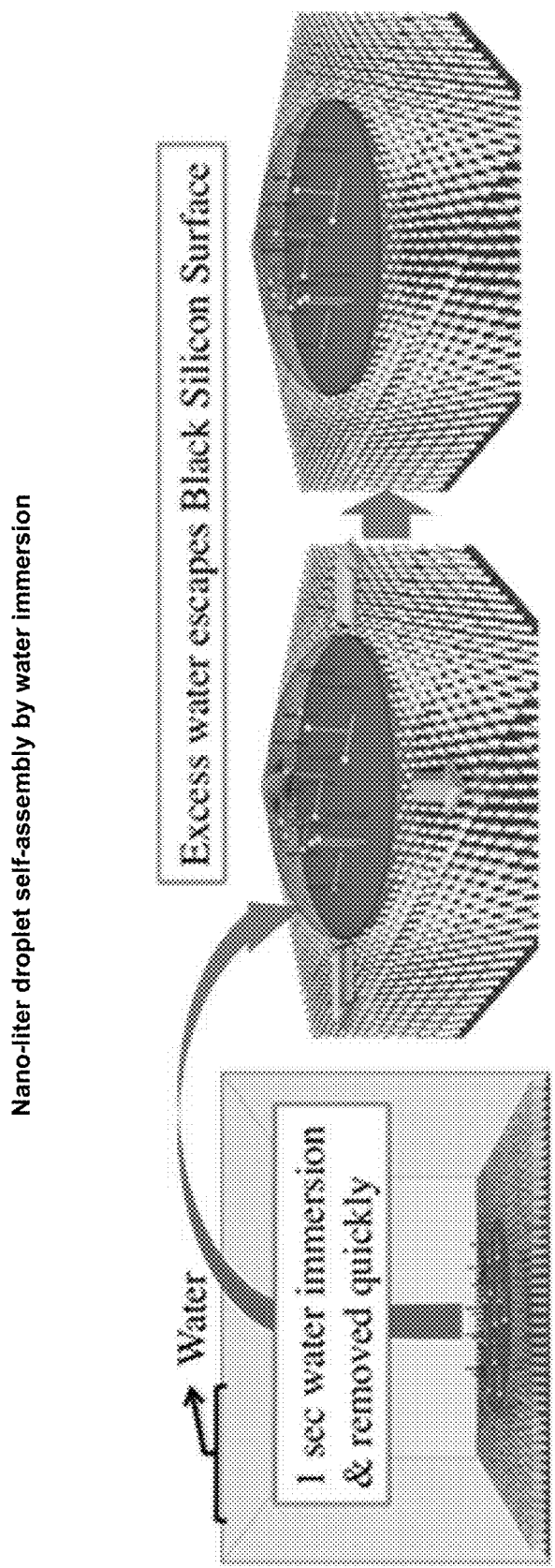
FIG. 22E shows the device is dipped in water for a specific time and removed, excess water escapes the super-hydrophobic black silicon surface, leaving a nano-liter droplet on each $SiO_2$ pattern.
Figure 22F:
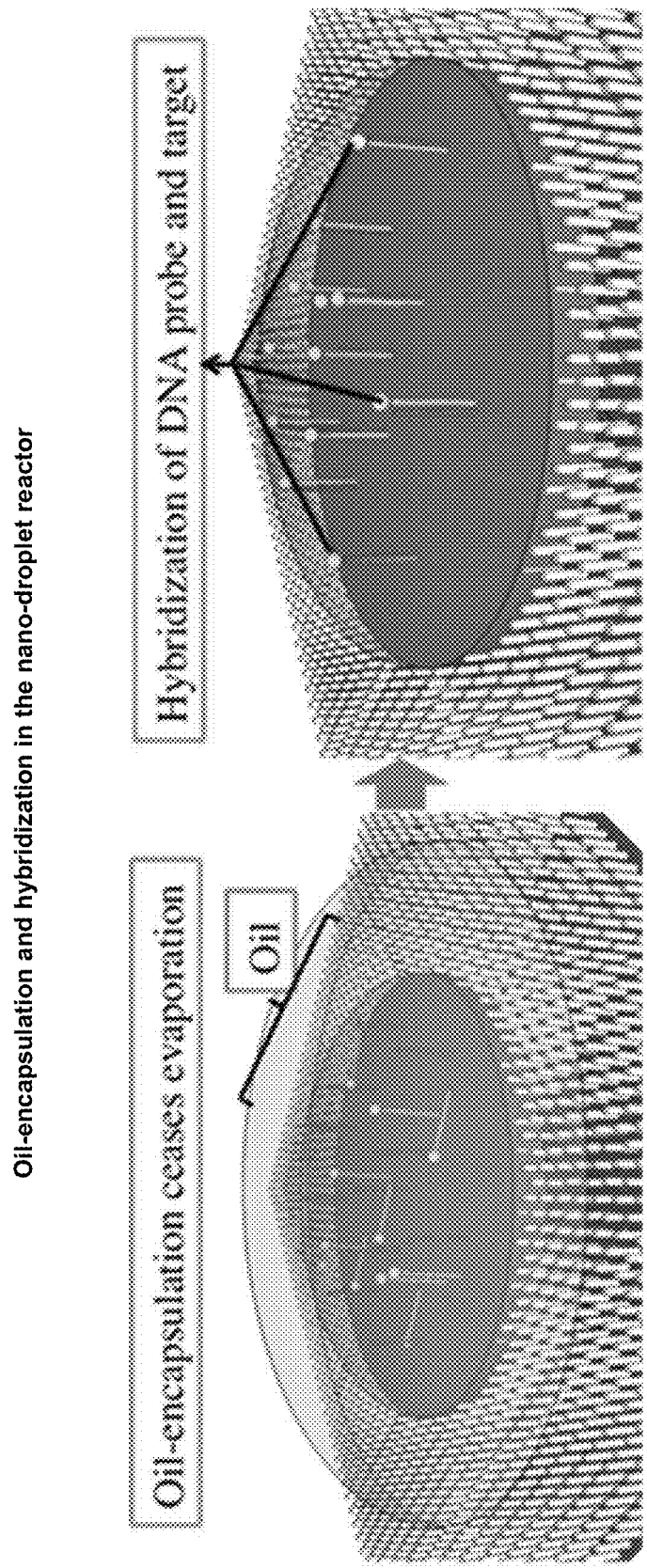
FIG. 22F shows that oil is added onto the nano-liter droplets, which stops evaporation, and the encapsulated nano-liter droplets undergo hybridization between DNA probes and targets.
Figure 22G:
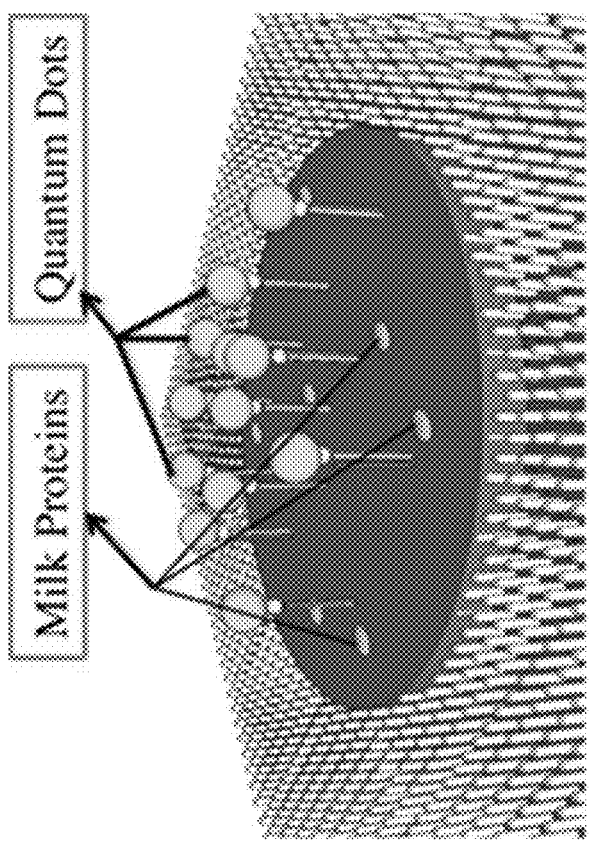
FIG. 22G shows the DNA probe-target duplexes are labeled with quantum dots for observation under fluorescent microscope.

Next, the device is dipped in hybridization buffer or water for a specific time (e.g., 1 second) and removed, excess hybridization buffer or water escapes the super-hydrophobic black silicon surface, leaving a nano-liter droplet on each $SiO_2$ pattern (see FIG. 22E). After forming the nano-droplets (e.g., nanoliter volume or less) on the device, oil is added onto the nano-liter droplets, which stops evaporation, and the encapsulated nano-liter droplets undergo hybridization between DNA probes and targets (see FIG. 22F). In some embodiments, the device is immersed in oil and heated to undergo target-probe hybridization within the oil-encapsulated nano-droplets (e.g., nanoliter volume or less). Subsequently, the device is removed from oil and the DNA probe-target duplexes are labeled with quantum dots for observation under fluorescent microscope (see FIG. 22G). In some embodiments, milk protein was added to prevent non-specific binding.

To demonstrate the massively parallel nature of the disclosed nano-droplets (e.g., nanoliter volume or less) microarray, data are generated on droplet volume, droplet volume variance, and nucleic acid retention resulted from the disclosed workflow. During the proposed workflow, after drying DNA target solution on SiO$_2$ pattern, the device is dipped in water or hybridization buffer to form nano-droplets (e.g., nanoliter volume or less) on each pattern. The underlining principal of this self-assembled process can be attributed to black silicon's super-hydrophobicity, i.e., the black silicon-water adhesion force is far less than water cohesion force. On the other hand, SiO$_2$ is hydrophilic and the SiO$_2$-water adhesion force is greater than water cohesion force. During dipping, water adheres onto SiO$_2$ surfaces and escapes from the black silicon surface, thus forming many nano-droplets (e.g., nanoliter volume or less). In some implementations, the nano-droplet (e.g., nanoliter volume or less) size is governed primarily by SiO$_2$ pattern size and contact angle of the water-SiO$_2$ interface.

Figure 23A:
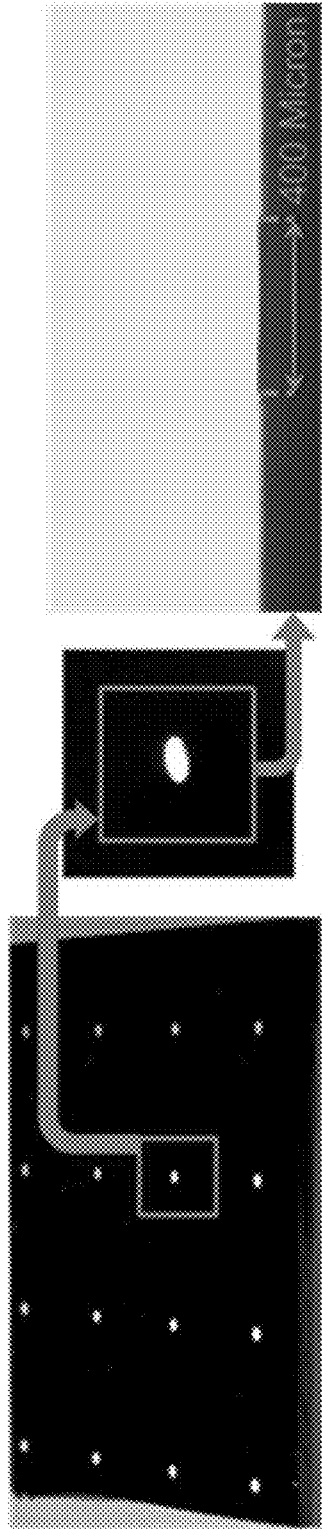
FIG. 23A shows top and side view of the 400 micron diameter circular pattern prior to water immersion.
Figure 23B:
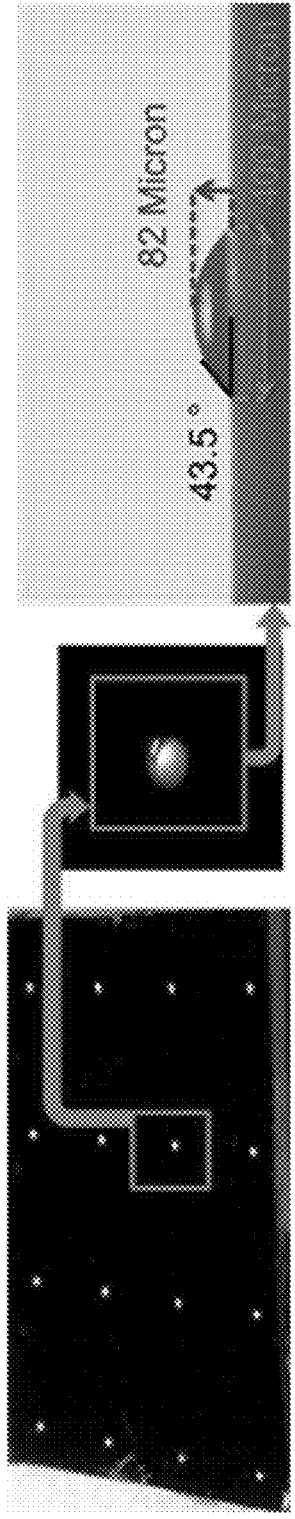
FIG. 23B shows top and side view of the nano-liter droplet pattern after 1 second water immersion and removal having a dome-shaped.
Figure 23C:
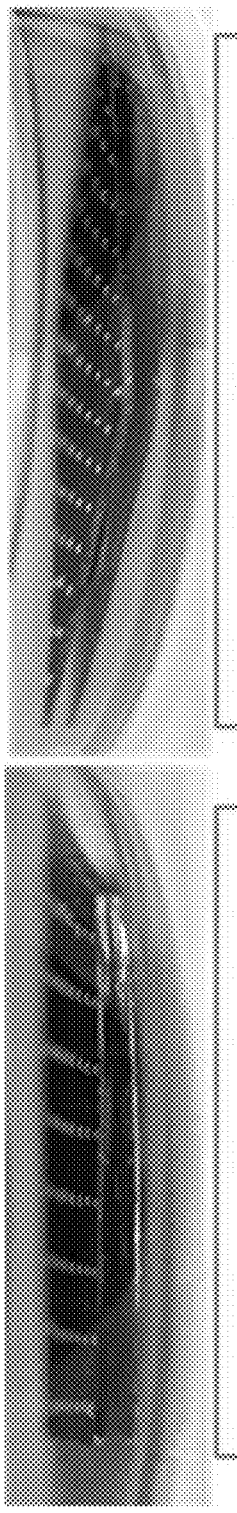
FIG. 23C shows parallel and 45° views of an array of nano-droplets (e.g., nanoliter volume or less) immersed in oil.

FIGS. 23A-23C show characterization of an exemplary nano-liter droplet array obtained using the workflow shown in FIGS. 22A-22G. FIG. 23A shows top and side view of the ~400 micron diameter circular patterns prior to water immersion. FIG. 23B shows top and side view of the nano-liter droplet after 1 second water or hybridization buffer immersion and removal having a dome-shaped pattern. The nano-droplet (e.g., nanoliter volume or less) is formed at a height of ~82 micron and a water contact angle on the SiO$_2$ surface of ~43.5°. FIG. 23C shows parallel and 45° views of an array of nano-droplets (e.g., nanoliter volume or less) immersed in oil.

In the embodiments shown in FIG. 23B, the geometry of water droplet resembles a spherical cap with average height of ~82 um and diameter of 400 um, which can be used to compute a droplet volume of 5.4 nL. Table 2 shows exemplary nano-droplet volumes (e.g., nanoliter volume or less) obtained from multiple samples after 1-second water or hybridization buffer dipping. To verify that the droplet geometry is indeed a spherical cap, one can check agreements between the droplet height, contact radius, and contact angle. Subject to the spherical cap geometry, the nano-droplet volume ($V_d$) (e.g., nanoliter volume or less) can be characterized by the droplet height (h), contact radius ($R_c$), radius of the sphere forming the spherical cap ($R_d$), and the contact angle ($\theta$). Generally, two variables out of the four are needed to characterize other variables. In some embodiments, the relationships between these four variables can be expressed as:

$$V_d = \frac{1}{6}\pi h(3\ R_c^2 + h^2),\ R_d = \frac{R_c^2 + h^2}{2\ h},\ \theta = 2\ \tan^{-1}\frac{h}{R_c} \quad (3)$$

Thus, the contact angle may be based on the droplet height and contact radius, and obtained to be 44.6°, which is in agreement with our measurement of 43.5°.

TABLE 2

| Nano-droplet volumes after 1-second water dipping | |
|---|---|
| Sample # | Nano-liter droplet Volume (nl) |
| 1 | 5.4 |
| 2 | 5.8 |
| 3 | 5.3 |
| 4 | 5.1 |
| 5 | 5.5 |
| 6 | 5.6 |
| Mean | 5.4 |
| Standard Deviation | 0.3 |

The water dipping process forms nano-droplets (e.g., nanoliter volume or less) in a massively parallel fashion due to low variances in the SiO$_2$ pattern size and contact angle of the water-SiO2 interface. In exemplary device setup, the SiO$_2$ pattern size is patterned onto the silicon wafer by photolithography, which offers low variance (+/−1 micron) for 400 microns patterning. The contact angle, on the other hand, may be determined by interfacial energy and hysteresis. During water immersion and removal, a thin layer of water is formed homogenously across the array device. Because the water on top of black silicon is in a dynamically unstable Cassie state, as water on the edge of the device dissipates, the entire water layer on black silicon follows and leaves nano-droplets (e.g., nanoliter volume or less) on SiO$_2$ patterns. The nano-droplets (e.g., nanoliter volume or less) are formed by a self-assembled process in which the water cohesion force is greater than the adhesion force between water and black silicon, thus stripping waters from the surface. In contrast, water cohesion force is less than the adhesion force between water and SiO$_2$, thus forming nano-liter water droplets. Because both water cohesion and surface adhesion forces are material properties that vary with the purity of water, SiO$_2$ and black silicon surface consistency, and temperature, the contact angle of the nano-droplet (e.g., nanoliter volume or less) is intrinsically homogenous across the microarray. The nano-droplets (e.g., nanoliter volume or less) have a droplet size standard deviation of 300 pL (Table 2). Table 3 shows the setup of three example nucleic acids used for synthetic miR-205 DNA mimic quantification. Overall, the homogeneity of both SiO$_2$ pattern size and contact angle results in a massively parallel, self-assemble nano-droplet (e.g., nanoliter volume or less) microarray.

TABLE 3

| Single strand DNA for Synthetic miR-205 DNA mimic quantification | | | |
|---|---|---|---|
| Sequence Name | Sequence (5'-3') | Modification | Length |
| DNA Probe | TGC GAC CTC AGA CTC CGG TGG AAT 3' GAA GGA AAA AAA AAA A (SEQ ID NO: 2) | C6Amine | 40 nt |

TABLE 3-continued

Single strand DNA for Synthetic miR-205 DNA mimic quantification

| Sequence Name | Sequence (5'-3') | Modification | Length |
|---|---|---|---|
| Scrambled DNA Probe | AGC AGG AGA TAC GAC ATA ATA CAC GAT AAG TAG ACA CGA G 3' (SEQ ID NO: 4) | C6Amine | 40 nt |
| DNA Target (Synthetic miR-205 DNA mimic | TCC TTC ATT CCA CCG GAG TCT GAG GTC GCA 3' (SEQ ID NO: 3) | Biotin | 30 nt |

Figure 24:
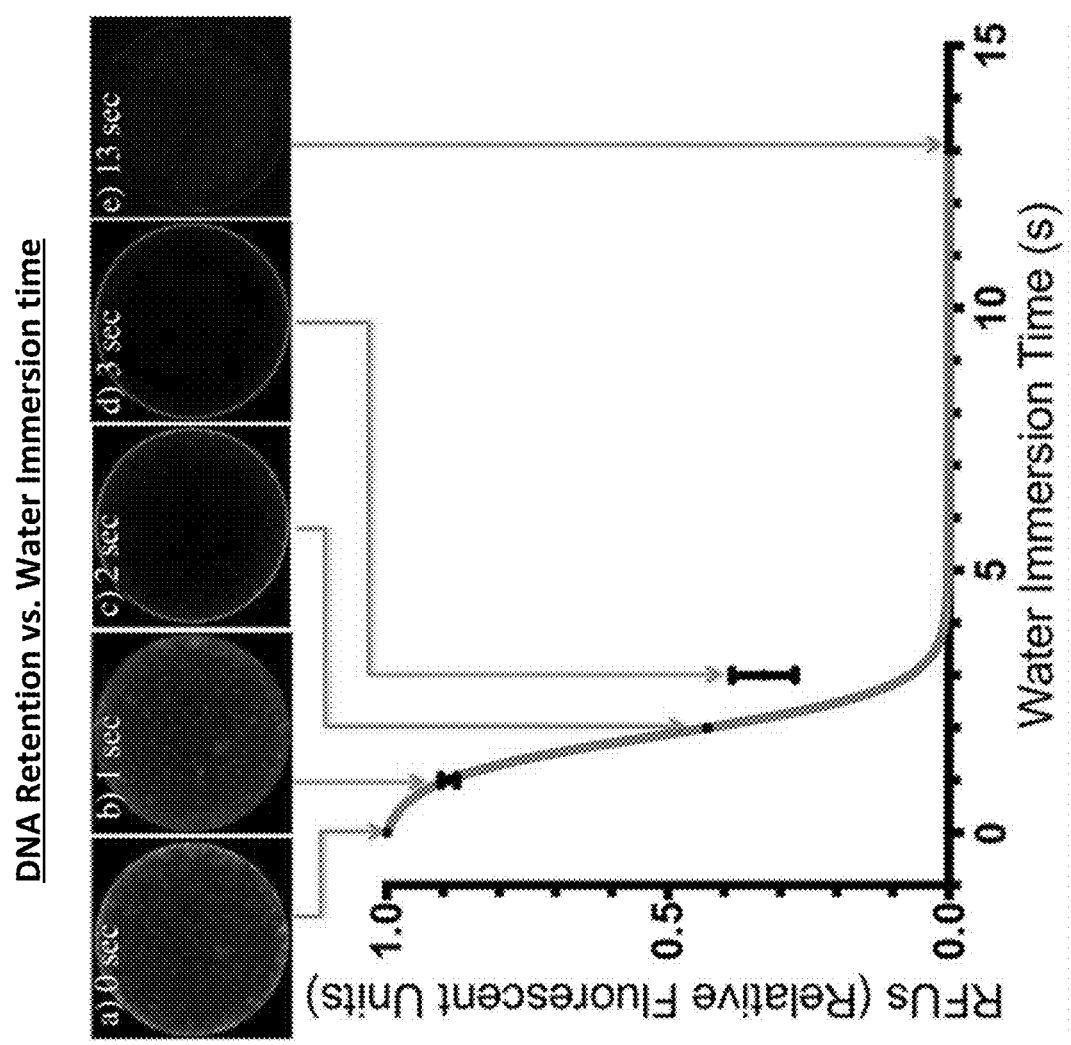
FIG. 24 shows DNA retained on $SiO_2$ surface after drying from water immersion at different immersion lengths of 0, 1, 2, 3, and 13 seconds, respectively.

Mass transfer occurs when there is a concentration gradient across two connected systems. Nevertheless, with brief dipping process, the majority of the nucleic acids are retained on the SiO$_2$ pattern. During water or hybridization buffer immersion, there is a significant nucleic acid concentration gradient across the SiO$_2$ pattern and the liquid reservoir, and thus after water or hybridization buffer removal, loss of nucleic acid from mass transfer is expected. The relationship between water immersion duration and nucleic acid retention is quantified by drying fluorescently labeled DNA on SiO$_2$ patterns and recording the fluorescent signal for water immersion time varying from 1-13 seconds. FIG. 24 shows DNA retained on SiO$_2$ surface based on the measured fluorescent intensity after drying from water immersion at different immersion lengths of 0, 1, 2, 3, and 13 seconds, respectively. DNAs used in the exemplary device are 24 nucleotides in length and labeled with FAM. Relative fluorescent units are calculated by normalizing the integrated intensity with respect to 0 seconds water immersion. While a significant decay in fluorescent signal is observed for 2-seconds water immersion, ~90% of the original signal is retained for 1-second water immersion.

To demonstrate the performance of the nano-droplet (e.g., nanoliter volume or less) microarray device, we present data on DNA target sensitivity curve, dynamic range, and accelerated hybridization kinetics. Particularly, synthetic miR-205 DNA mimic was chosen to be the DNA target to illustrate applications for short, 30mer oligonucleotides quantification. In the disclosed device workflow, DNA targets are dried onto the SiO$_2$ pattern and re-suspended in nano-droplets (e.g., nanoliter volume or less). Depending on the initial solution volume prior to drying, different degrees of enrichment can be achieved by the disclosed workflow and thus resulting in different sensitivity curves.

Figure 25A:
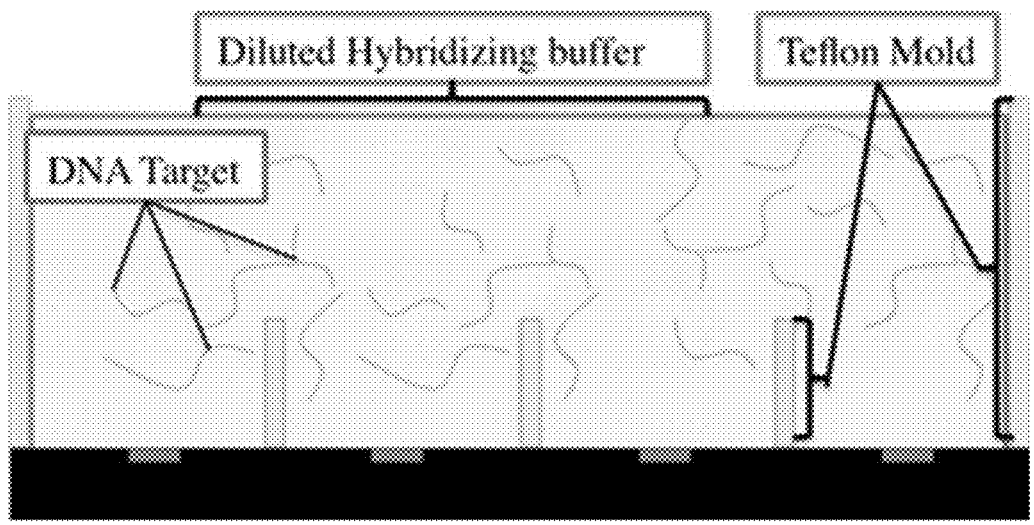
FIG. 25A shows 1 ml to 5 µl enrichment achieved by evaporating target DNA solution at 95° C. while Teflon mold restricts solution above the $SiO_2$ patterns.
Figure 25B:
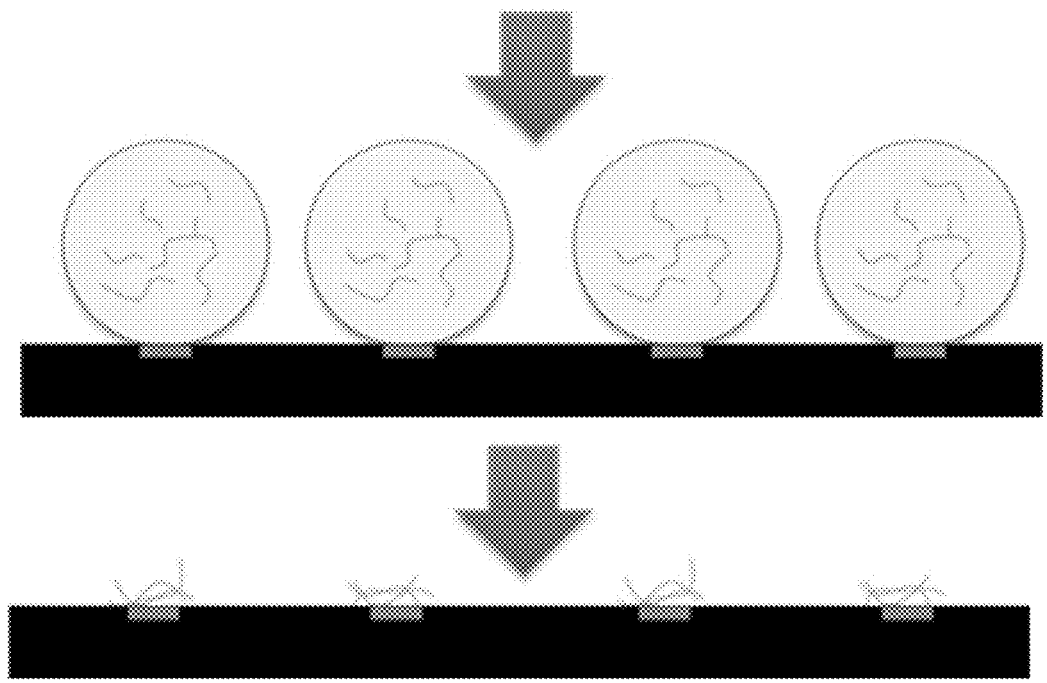
FIG. 25B shows 5 µl to 5 nl enrichment achieved by evaporating target DNA solution at 50° C., followed by nano-liter droplet self-assembly described in FIG. 22E.

We have implemented two enrichment conditions with initial solution volumes of 1 mL and 5 µL. FIGS. 25A-25D show DNA target (e.g., Synthetic miR-205 DNA mimic) sensitivity from 1 ml to 5 µl and then from 5 µl to 5 nl enrichment. FIG. 25A shows 1 ml to 5 µl enrichment achieved by evaporating target DNA solution at 95° C. while Teflon mold restricts solution above the SiO$_2$ patterns. FIG. 25B shows 5 µl to 5 nl enrichment achieved by evaporating target DNA solution at 50° C., followed by nano-liter droplet self-assembly described in FIG. 22E. When starting with 1 mL of initial volume, the solution undergoes a two-step drying process that begins with an accelerated evaporation at 95° C. from 1 ml to 5 µL, and followed by a slower evaporates from 5 µL to dry at 50° C. However, when starting with 5 µL of initial volume, the solution evaporates to dry in one step at 50° C. While evaporation time minimizes when the drying process is carried out near the boiling point, in practice we reduces evaporation temperature when DNA target solution volume decreases to 5 µL. This temperature control is needed to prevent droplet state transition that can hinder solution self-realignment to the SiO$_2$ pattern.

Briefly, water in contact with nano-patterned, super-hydrophobic surface such as black silicon can existed in either Cassie or Wenzel states. Cassie state is a state in which the liquid is in contact with only the nano-pattern peaks and thus trapping air pockets underneath and demonstrating unstable dynamics. Wenzel state, on the other hand, describes full liquid contact with the surface and shows significant resistance to movement. Simulation predicts equal energy level for both states separated by a free-energy barrier and states coexistence. Yet, experimental investigations revealed a lowered energy level in Wenzel state, indicating an irreversible state transition. Furthermore, the state-transition is initiated via a nucleation event that is dependent of the contact area and thermal energy. At DNA target solution volume of 5 µL, evaporation is carried out at 50° C. to minimize nucleation event that initiates the Cassie-Wenzel state transition. Premature Cassie-Wenzel state transition during evaporation causes redeposition of dried DNA target outside the intended SiO2 pattern. By switching from 95° C. to 50° C. at different stage of drying, the dried target area coverage closely resembles that of the SiO$_2$ pattern size.

Figure 25C:
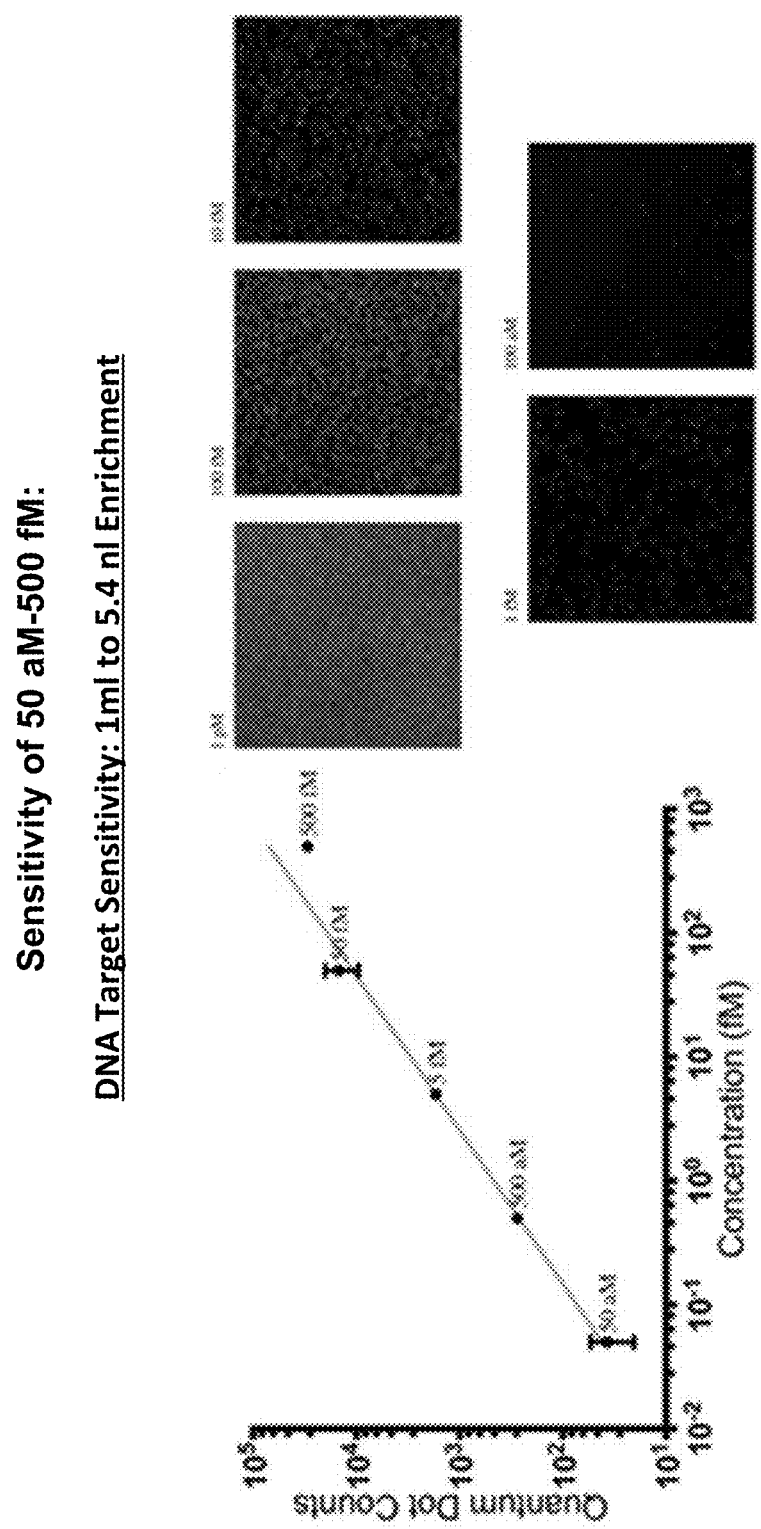
FIG. 25C shows that 1 ml to 5 nl enrichment results in a linear sensitivity curve ranging from 50 aM to 500 fM.
Figure 25D:
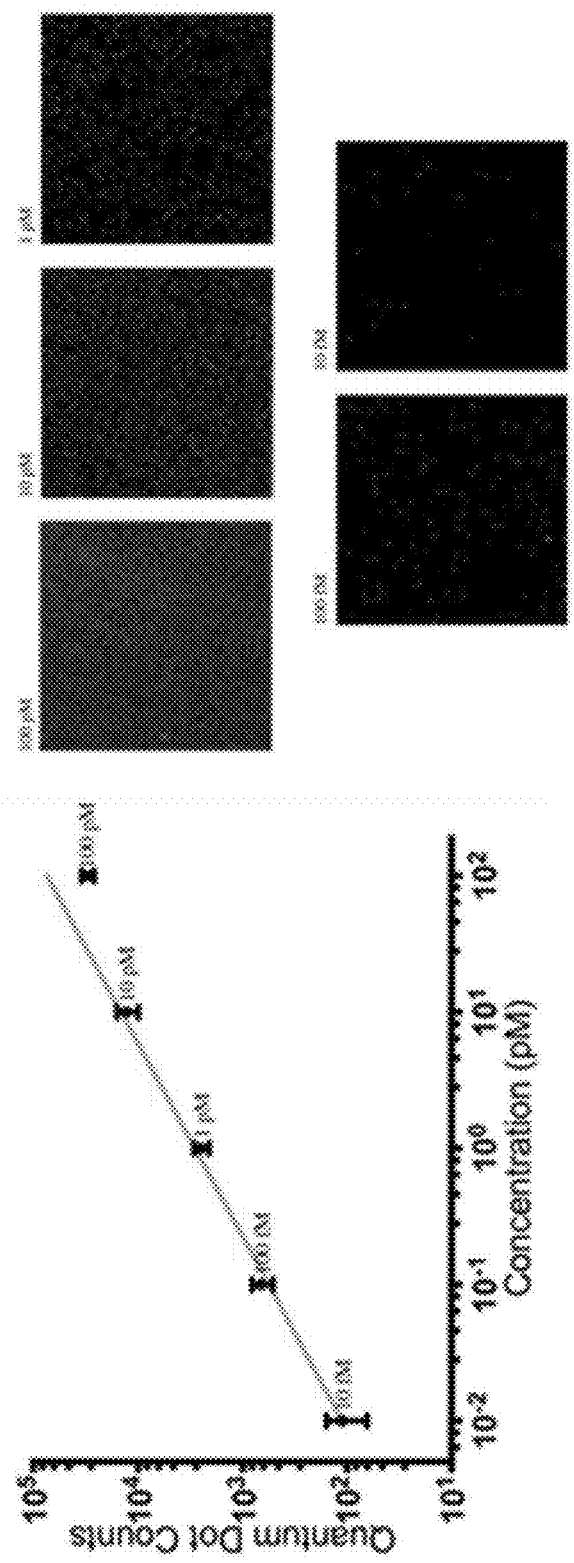
FIG. 25D shows that 5 µl to 5 nl enrichment results in a linear sensitivity curve ranging from 10 fM to 100 pM.

Both drying processes starting at different initial volumes conclude with water or hybridization buffer dipping that generates homogenous, 5.4 nL of nano-droplets. The resulting volume changes lead to solute concentration enrichment of 1,000 and 200,000 times respectively for initial volume of 5 µL and 1 mL. These 2 enrichment ratios translate directly into the sensitivity curve observed: 1 mL and 5 µL initial volumes correspond to sensitivity curves covering 50 aM to 500 fM and 10 fM to 100 pM DNA target concentration (see FIGS. 25C-25D). FIG. 25C shows that 1 ml to 5 nl enrichment results in a linear sensitivity curve ranging from 50 aM to 500 fM. FIG. 25D shows that 5 µl to 5 nl enrichment results in a linear sensitivity curve ranging from 10 fM to 100 pM.

The signal is expressed in number of quantum dots counted on the 145×108 micron detection area, and negative control quantum dots count resulted from scrambled sensing DNA is subtracted from the signal.

Moreover, given the same nano-droplet volume (e.g., nanoliter volume or less), knowing the copy number of DNA target is sufficient to determine the final quantum dot signal, regardless of particular initial volume or target concentration. For instance, 1 mL of 5 fM DNA target and 5 µL of 1 pM DNA target display almost identical quantum dot binding signal in our sensitivity curve because both contain ~5 amole of DNA target. Still, we observed slightly lowered quantum dot binding systemically with initial volume of 1 mL due to either the result of the extensive drying process or possible molecule adherence to the Teflon mold surface.

Besides absolute copy number, DNA target concentration also provides important biologically relevant information, and thus a wide concentration dynamic range is desired. On a log-log plot, both 1 mL and 5 µL initial volume sensitivity curves in FIGS. 25C-25D display linear relationship between the quantum dot binding signal and the DNA target concentration, exhibiting 4 orders of dynamic range. Sensitivity curve's dynamic range is intrinsically limited by optical diffraction and photonic sensor performance. By combining the two sensitivity curves with partially overlapping sample concentration range for cross-reference, a dynamic range of over 6 orders of magnitude is demonstrated. The slope for these linear curves is less than 1 for both cases (0.7 for 1 mL and 0.8 for 5 µL initial volume), meaning that the overall binding efficiency reduces as target DNA concentration increases. The effect of DNA probe surface density on binding efficiency is well studied: increasing DNA probe surface density may lead to reduced binding efficiency, which is caused by steric hindrance and electrostatic repulsion. Because quantum dots have high negative surface charges, electrostatic repulsion is likely the cause of the reducing overall binding efficiency with increasing target DNA concentration.

In conventional microarrays, extended hybridization time (16+ hours) is required for DNA targets to diffuse from bulk solution toward surface DNA probes. Due to enrichment by evaporation and reduced volume of the nano-droplet (e.g., nanoliter volume or less) array, hybridization time in the disclosed technology is reduced to 5 minutes. This can be at least partially attributed to the nano-droplet (e.g., nanoliter volume or less) height, or the target DNA maximum diffusion length, which is ~80 microns, as oppose to ~2 mm in the case of a 4 µl droplet. In a model of one-dimensional target DNA-probe DNA binding, the binding efficiency ($\eta(t)$) is diffusion limited and related to diffusion coefficient of the target ($D_T$), time (t), and diffusion length (L) as following:

$$\eta(t) \propto 1 - e^{-\frac{D_T \pi^2 t}{(2L)^2}}. \quad (4)$$

According to this model, a diffusion length reduction from 2 mm to 80 micron (25 fold) leads to time reduction of 625 folds; therefore, the time required for completing hybridization can theoretically be accelerated from 16 hours to 90 seconds.

Figure 26:
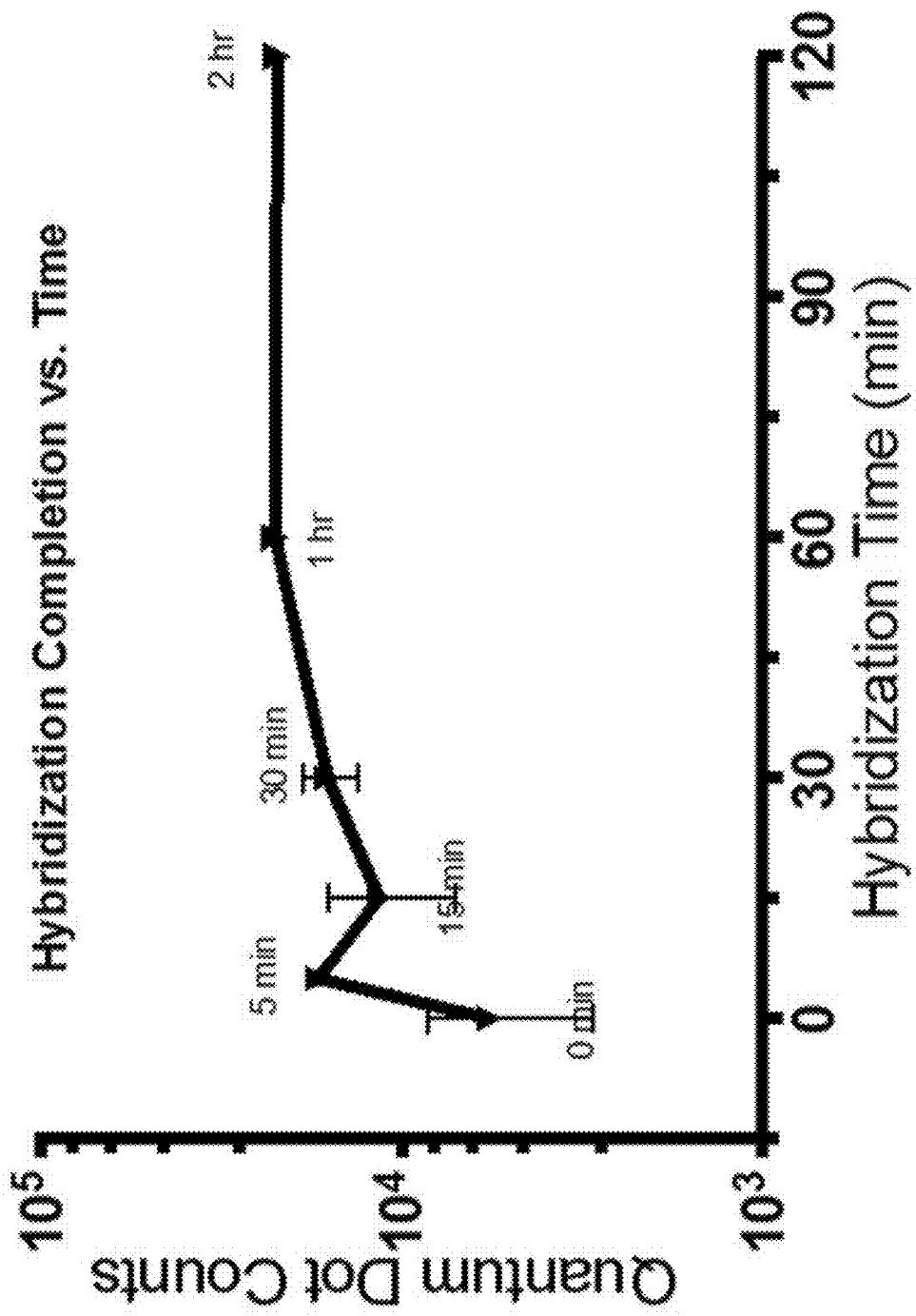
FIG. 26 shows hybridization completion rate vs. hybridization time within the nano-droplets (e.g., nanoliter volume or less).

FIG. 26 shows hybridization completion rate vs. hybridization time within the nano-droplets (e.g., nanoliter volume or less). 10 pM of Synthetic miR-205 DNA mimic enriched from 5 µl to 5 nl is allowed to hybridize from 5 minutes to 2 hours in nano-droplets (e.g., nanoliter volume or less). The signal is expressed in number of quantum dots counted on the 145×108 micron detection area, and negative control quantum dots count resulted from scrambled sensing DNA is subtracted from the signal. As shown in FIG. 26, the accelerated hybridization is demonstrated by incubating the nano-droplet (e.g., nanoliter volume or less) array for various amount of time. After 5 minutes of hybridization, hybridization is completed binding efficiency cease to increase with time. Nevertheless, a significant binding efficiency is observed without any incubation, suggesting hybridization occurrence during the drying process.

Lastly, a comprehensive evaluation of the nano-droplet (e.g., nanoliter volume or less) microarray is addressed across many criteria including maximum sensitivity, linear dynamic range, hybridization time, and throughput. Table 4 shows the comparison of maximum sensitivity, linear dynamic range, hybridization time, and throughput of the disclosed nano-droplet (e.g., nanoliter volume or less) microarray and other recent microarray-based techniques for nucleic acid quantification. Compared to other recent microarray-based techniques, nano-droplet (e.g., nanoliter volume or less) microarray disclosed in this patent document shows significant improvements in terms of sensitivity, linear dynamic range, and hybridization time (Table 4). While most other methods focus on improvements in nucleic acid chemistry, surface treatments, and microfluidic design, nano-droplet (e.g., nanoliter volume or less) array relies on physical enrichment of DNA targets and accelerated hybridization kinetics due to its miniature droplet dimension. To summarize, the nano-droplet (e.g., nanoliter volume or less) microarray has achieved a maximum sensitivity of 50 aM (50 zmol), 6 orders or linear dynamic range, 5 minutes of hybridization time, and a throughput similar to current microarray platforms.

TABLE 4

Comparison of maximum sensitivity, linear dynamic range, hybridization time, and throughput of the "Nano-droplet (e.g., nanoliter volume or less) Microarray" and other recent microarray-based methods for nucleic acid quantification.

| Method | Detection method | Maximum Sensitivity | Linear Dynamic Range | Hybridization Time | Throughput (+) |
|---|---|---|---|---|---|
| Nano-droplet (e.g., nanoliter volume or less) Microarray (disclosed technology) | Quantum Dots | 50 aM/ 50 zmol | 6 orders | 5 min | +++ |
| Microconcentration | Fluorescence (Texas Red) | 100 pM/ 2 fmol | 3 orders | 30 min | +++ |
| Oil-encapsulated nano-droplet array | Quantum Dots | 100 fM/ 400 zmol | 2 orders | 30 min | +++ |
| Direct and sensitive miRNA profiling | Fluorescence (Cy3 and Cy5) | 5 fM/ 200 zmol | 4 orders | 20-48 hr | +++ |
| Ternary Surface Monolayers | Electrochemistry (HRP enzyme) | 10 fM/ 40 zmol | 5 orders | 30 min | ++ |
| Ultra-sensitive single-molecule detection | Quantum Dots | 10 fM/ 500 zmol | 3 orders | 1 hr | + |

TABLE 4-continued

Comparison of maximum sensitivity, linear dynamic range, hybridization time, and throughput of the "Nano-droplet (e.g., nanoliter volume or less) Microarray" and other recent microarray-based methods for nucleic acid quantification.

| Method | Detection method | Maximum Sensitivity | Linear Dynamic Range | Hybridization Time | Throughput (+) |
|---|---|---|---|---|---|
| Two-temperature hybridization with LNA probes | Fluorescence (Cy3) | 10 fM/ 1 amol | 4 orders | 16 hr | +++ |
| Paper-based solid-phase assay | Quantum Dots-Cy3 FRET | 300 fmol | 1 orders | 30 min | ++ |
| Duplex-specific nuclease | Electrochemistry | 1 fM | 2 orders | 12 hr | ++ |
| Isotachophoresis | Fluroescence (Cy3) | 100 fM | 3 orders | 30 min | +++ |

Materials and Processes

Nano-Liter Droplet Array Process Flow

Three example nucleic acids tested are listed in Table 3. After surface pretreatment, SiO2 pattern surfaces are crosslinked with DNA probes (see FIG. 22B). A volume of 5 ul or 1 ml solution of target DNA is added onto SiO2 pattern (see FIG. 22C) and allowed to evaporate at controlled temperature. While evaporating, the DNA target solution droplets are realigned onto SiO2 patterns, shrink, and are dried completely (see FIG. 22D) onto SiO2 patterns. Immersing the device with dried DNAs in water or hybridization buffer for 1 second and removing the device quickly (see FIG. 22E), nano-droplets (e.g., nanoliter volume or less) with resuspended DNAs are self-assembled on SiO2 patterns. To avoid evaporation of droplets, oil is immediately added onto the nano-liter droplets, ceasing evaporation (see FIG. 22F). After 5 minutes incubation at 50° C., DNA probes and targets hybridize and form DNA duplexes. Finally, SiO$_2$ patterns are coated with milk protein to prevent non-specific binding and the duplexes are labeled with quantum dots for observation (see FIG. 22G).

Device Fabrication

Embodiments of the device fabrication technique have been described earlier in this patent document. Briefly, 400-micron diameter circular patterns are formed on a mechanical grade silicon wafer by conventional photolithography, and then coated with SiO2 and a protective chromium layer. By deep reactive ion etch (DRIE), superhydrophobic black silicon surface forms around the patterns. Lastly, the chromium protective layer is removed by chromium etchant.

Device Surface Pretreatment

Embodiments of the device surface pretreatment prior to the nano-droplet (e.g., nanoliter volume or less) hybridization array workflow have been described earlier in this patent document. Following device fabrication, SiO$_2$ island surfaces are coated with aminosilane (APTES) and then functionalized with aldehyde. DNA probe and scrambled DNA probe (negative control) are spotted on the SiO$_2$ islands via crosslinking reaction between the amine 3' modification of the DNA probe and the aldehyde functional group on SiO$_2$ island surfaces.

Image Analysis and Quantum Dot Counting

Sample images are taken under 100× oil immersion lens (e.g., Nikon, NA1.45) with an enclosed fluorescent microscope (e.g., Keyence BZ-9000). The samples are excited by mercury lamplight filtered through a single-band bandpass filter (e.g., Samrock, 405/10 nm) and the emission light is filtered by another single-band bandpass filter (e.g., Samrock, 536/40 nm). Raw images taken from the microscope are processed through haze reduction and black balance algorithms. Finally, the quantum dots remaining on the SiO$_2$ islands are counted using object size, connectivity, and intensity filters integrated in an object counter module included in the microscope software (e.g., BZ-II Analyzer). The raw images are captured within a detection area of 145×108 μm$^2$. In principle, each quantum dot signifies a single DNA target hybridized with the probe, yet quantum dot residues might be left on the surface due to incomplete wash. In some embodiments, the real signal in the sensitivity curves and hybridization time-series can be expressed as the difference between the quantum dots counts for the DNA probe and scrambled DNA probe with the same target DNA (e.g., synthetic miR-205 DNA mimics) concentration.

Discussion

Various embodiments of the disclosed technology has established and validated an ultra-sensitive nucleic acid quantification technique and device based on the nano-droplet (e.g., nanoliter volume or less), on-chip concentration array platform. The detection scheme utilized the patterned black-silica surface to induce self-assembly mechanism of nano-droplets (e.g., nanoliter volume or less) formation, allowing precise control of sample volumes and massively parallel processing capability. Coupled with the rapid evaporation feature of the device, the samples can be greatly enriched to enable nucleic acid detection at both 50 aM to 500 fM and 10 fM to 100 pM concentrations resulted in a combined wide linear dynamic range of 6-orders. Moreover, the reduced sample droplet volume facilitates hybridization reaction to within 5 minutes and greatly shortens the time scale required for the quantification process. Combining the features above, the disclosed technology demonstrates a unique nucleic acid detection system with significantly improved sensitivity and speed over existing microarray platforms.

While this patent document contain many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A method performed by a biosensor device for enriching molecules to facilitate ultra-sensitive detection of the molecules, the method comprising:
receiving, by a biosensor device including a microarray of hydrophilic islands having sensing areas and surrounded by a hydrophobic structure, bio-molecular probes over the sensing areas to functionalize the sensing areas of the microarray of hydrophilic islands, wherein the bio-molecular probes are capable of detecting biomarker molecules;
mixing a sample comprising biomarker with hybridization buffer to from a biomarker solution;
receiving, over the functionalized sensing areas of the microarray of hydrophilic islands, droplets of the biomarker solution that includes the biomarker molecules to form droplets of the biomarker molecules that cover the sensing areas of the microarray of hydrophilic islands;
allowing the droplets of the biomarker solution to evaporate over the microarray of hydrophilic islands to enrich the biomarker molecules onto the sensing areas of the microarray of hydrophilic islands;
receiving, over the functionalized sensing areas of the microarray of hydrophilic islands containing the enriched biomarker molecules, a liquid in a controlled time to form an array of self-assembled droplets of nanoliter volume or less to resuspend the enriched biomarker molecules in the droplets over the functionalized sensing areas;
receiving, over the array of self-assembled droplets of the biomarker solutions, a layer of oil to encapsulate the array of self-assembled droplets to form encapsulated reaction chambers for controlling a reaction between the biomarker molecules and the bio-molecular probes; and
detecting a hybridization between the biomarker molecules and the bio-molecular probes.

2. The method of claim 1, wherein the liquid includes one of:
a hybridization buffer containing a labeling material for labeling the biomarker molecules that have reacted with the bio-molecular probes or
water.

3. The method of claim 2, wherein the liquid is the hybridization buffer and the labeling material includes quantum-dots linked reporting DNAs.

4. The method of claim 1, wherein the microarray further comprises a grid of hydrophobic nanostructures separating individual hydrophilic islands.

5. The method of claim 1, wherein the biomarker solution includes miRNA containing RNAse-free deionized water.

6. The method of claim 1, wherein the biomarker molecules include DNAs, RNAs, miRNAs, synthetic miR-205 DNA mimic, or other nucleic acids.

7. The method of claim 1, wherein the hydrophobic structure includes a nanopillar structure made of black silicon.

8. The method of claim 1, wherein the sensing areas of the microarray of hydrophilic islands include a layer of $SiO_2$.

9. The method of claim 1, wherein each of the sensing areas of the microarray of hydrophilic islands is configured to detect a different biomarker molecule.

10. The method of claim 1, wherein the biosensor device is configured to perform parallel operation with a large number of biomarker molecules.

11. The method of claim 1, wherein the biosensor device is able to detect a biomarker molecule with a detection sensitivity of approximately 0.05 femtomolar (fM).

12. The method of claim 1, wherein the controlled time is approximately 1 second.

13. The method of claim 1, wherein after the completion of the hybridization, the method further includes receiving, at the functionalized sensing areas, a cleaning liquid to remove the layer of oil and liquid to expose the hybridized biomarker molecules and the bio-molecular probes.

14. The method of claim 1, wherein allowing the droplets of the biomarker solution to evaporate over the microarray of hydrophilic islands to enrich the biomarker molecules includes allowing the liquid in the biomarker solution to completely dry.

15. The method of claim 1, wherein allowing the droplets of the biomarker solution to evaporate over the microarray of hydrophilic islands to enrich the biomarker molecules includes allowing the biomarker solution to enrich to a predetermined thickness.

16. The method of claim 15, wherein the predetermined thickness is approximately 20 µm.

* * * * *

```
                        SEQUENCE LISTING

<160> NUMBER OF SEQ ID NOS: 6

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aaaaaaaaaa                                                              10

<210> SEQ ID NO 2
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
tgcgacctca gactccggtg gaatgaagga aaaaaaaaaa                             40

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tccttcattc caccggagtc tgaggtcgca                                        30

<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
agcaggagat acgacataat acacgataag tagacacgag                             40

<210> SEQ ID NO 5
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
tgcgacctca gactccggtg gaatgaagga aaaaaaaaaa                             40
```

```
<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 6
uccuucauuc caccggaguc ugaggtcgca                                      30
```